US009173856B2

(12) United States Patent
Strong et al.

(10) Patent No.: US 9,173,856 B2
(45) Date of Patent: *Nov. 3, 2015

(54) THERAPEUTIC REGIMEN AND METHODS FOR TREATING OR AMELIORATING VISUAL DISORDERS ASSOCIATED WITH AN ENDOGENOUS RETINOID DEFICIENCY

(75) Inventors: H. Andrew Strong, North Vancouver (CA); Suzanne Cadden, North Vancouver (CA)

(73) Assignee: QLT INC., Vancouver (CA)

(*) Notice: Subject to any disclaimer, the term of this patent is extended or adjusted under 35 U.S.C. 154(b) by 389 days.

This patent is subject to a terminal disclaimer.

(21) Appl. No.: 13/090,215

(22) Filed: Apr. 19, 2011

(65) Prior Publication Data

US 2011/0257266 A1 Oct. 20, 2011

Related U.S. Application Data

(60) Provisional application No. 61/447,611, filed on Feb. 28, 2011, provisional application No. 61/407,436, filed on Oct. 27, 2010, provisional application No. 61/325,763, filed on Apr. 19, 2010.

(51) Int. Cl.
*A61K 31/215* (2006.01)
*A61K 31/11* (2006.01)
*A61K 9/00* (2006.01)

(52) U.S. Cl.
CPC ............... *A61K 31/11* (2013.01); *A61K 31/215* (2013.01); *A61K 9/0095* (2013.01); *Y10S 514/912* (2013.01)

(58) Field of Classification Search
CPC ........................... Y10S 514/912; A61K 31/215
See application file for complete search history.

(56) References Cited

U.S. PATENT DOCUMENTS

| | | | |
|---|---|---|---|
| 3,196,078 A | 7/1965 | Chatzinoff et al. | |
| 3,517,067 A | 6/1970 | Stern | |
| 5,457,135 A | 10/1995 | Baranowitz et al. | |
| 5,620,970 A | 4/1997 | Han et al. | |
| 5,837,728 A | 11/1998 | Purcell | |
| 5,869,468 A | 2/1999 | Freeman | |
| 6,300,328 B1 | 10/2001 | Klimko | |
| 6,552,009 B2 | 4/2003 | Achkar | |
| 6,696,069 B2 | 2/2004 | Harichian et al. | |
| 7,494,222 B2 | 2/2009 | Jackson et al. | |
| 7,798,646 B2 | 9/2010 | Jackson | |
| 7,951,841 B2 | 5/2011 | Palczewski et al. | |
| 8,324,270 B2 | 12/2012 | Maeda et al. | |
| 8,962,691 B2 | 2/2015 | Palczewski et al. | |
| 2002/0028849 A1 | 3/2002 | Godkin et al. | |
| 2003/0215413 A1 | 11/2003 | Fares et al. | |
| 2003/0228277 A1 | 12/2003 | Gehlsen | |
| 2004/0022766 A1 | 2/2004 | Acland et al. | |
| 2004/0077604 A1 | 4/2004 | Lichtenberger | |
| 2004/0097587 A1 | 5/2004 | Arbiser | |
| 2004/0242704 A1 | 12/2004 | Palczewski | |
| 2005/0042278 A1 | 2/2005 | Ditzinger et al. | |
| 2005/0159662 A1 | 7/2005 | Imanishi | |
| 2006/0167088 A1* | 7/2006 | Widder et al. | 514/513 |
| 2006/0240098 A1 | 10/2006 | Castor | |
| 2006/0281821 A1* | 12/2006 | Palczewski et al. | 514/703 |
| 2007/0071872 A1 | 3/2007 | Goeseels et al. | |
| 2008/0221208 A1* | 9/2008 | Palczewski et al. | 514/529 |
| 2008/0275133 A1 | 11/2008 | Schwartz et al. | |
| 2010/0010084 A1 | 1/2010 | Yu | |
| 2010/0035986 A1 | 2/2010 | Maeda | |
| 2010/0136108 A1 | 6/2010 | Ditzinger et al. | |
| 2011/0034554 A1 | 2/2011 | Washington | |
| 2011/0288170 A1 | 11/2011 | Palczewski et al. | |
| 2012/0041073 A1 | 2/2012 | Palczewski et al. | |
| 2012/0322891 A1 | 12/2012 | Palczewski et al. | |
| 2013/0072443 A1 | 3/2013 | Palczewski et al. | |
| 2013/0072556 A1 | 3/2013 | Palczewski et al. | |
| 2013/0072557 A1 | 3/2013 | Maeda et al. | |
| 2013/0072558 A1 | 3/2013 | Maeda et al. | |
| 2013/0072559 A1 | 3/2013 | Palczewski et al. | |
| 2013/0072560 A1 | 3/2013 | Palczewski et al. | |
| 2013/0072561 A1 | 3/2013 | Maeda et al. | |
| 2013/0072568 A1 | 3/2013 | Palczewski et al. | |
| 2013/0072569 A1 | 3/2013 | Palczewski et al. | |
| 2013/0079403 A1 | 3/2013 | Palczewski et al. | |
| 2013/0196950 A1 | 8/2013 | Palczewski et al. | |

FOREIGN PATENT DOCUMENTS

| | | |
|---|---|---|
| CA | 2601278 | 9/2005 |
| CA | 2714530 A1 | 8/2009 |
| CN | 1169854 | 1/1998 |
| CN | 1455780 | 11/2003 |
| EP | 184942 B1 | 8/1990 |
| EP | 0803248 | 10/1997 |
| EP | 552624 B1 | 6/2000 |
| GB | 1449027 | 9/1976 |
| GB | 1452012 | 10/1976 |
| GB | 1526410 | 9/1978 |

(Continued)

OTHER PUBLICATIONS

The K-Zone, Biophysical data tables: standard man, Jul. 2004 printed Mar. 14, 2009 from http://www.kevinboone.com/biodat_stdman.html, 1 page.*

(Continued)

*Primary Examiner* — Gigi Huang
(74) *Attorney, Agent, or Firm* — Ropes & Gray LLP

(57) ABSTRACT

Disclosed herein are therapeutic regimens for treating or ameliorating a visual disorder associate with an endogenous retinoid deficiency in a subject by administering a therapeutically effective amount of a synthetic retinal derivative or a pharmaceutically acceptable composition comprising a synthetic retinal derivative according to the therapeutic regimen which leads to local recovery of visual functions such as visual fields, visual acuity and retinal sensitivity, among others.

47 Claims, 19 Drawing Sheets

(56) References Cited

FOREIGN PATENT DOCUMENTS

| | | |
|---|---|---|
| JP | 61-275266 | 5/1986 |
| JP | 6340525 | 12/1994 |
| JP | 8198746 | 8/1996 |
| JP | 2003-292414 | 10/2003 |
| RU | 2106843 | 3/1998 |
| WO | WO 99/29315 | 6/1995 |
| WO | WO 96/24344 | 8/1996 |
| WO | WO 97/03655 | 2/1997 |
| WO | WO 99/09969 | 3/1999 |
| WO | WO-99/20265 | 4/1999 |
| WO | WO 00/68364 | 11/2000 |
| WO | WO 01/01960 | 1/2001 |
| WO | WO 02/055540 | 7/2002 |
| WO | WO 02/082904 | 10/2002 |
| WO | WO 03/039521 | 5/2003 |
| WO | WO-03045379 A1 | 6/2003 |
| WO | WO 03/059336 | 7/2003 |
| WO | 2004/082622 | 9/2004 |
| WO | WO 2005/048994 | 6/2005 |
| WO | WO 2005/079774 | 9/2005 |
| WO | 2006/002097 | 1/2006 |
| WO | WO 2006/033734 | 3/2006 |
| WO | WO 2007/056242 | 5/2007 |
| WO | WO 2007/092509 | 8/2007 |
| WO | WO 2009/102418 | 8/2009 |
| WO | 2011/034551 | 3/2011 |
| WO | WO-2011132084 A2 | 10/2011 |

OTHER PUBLICATIONS

Moise et al., "Delivery of Retinoid-Based Therapies To Target Tissues" Biochemistry, 46(15): 4449-4458 (2007).

Morimura, H. et al., "Mutations in the RPE65 gene in patients with autosomal recessive retinitis pigmentosa or Leber congenital amaurosis" Proc Natl Acad Sci USA. 95(6):3088-3093 (1998).

O'Byrne et al., "Retinoid Absorption and Storage Is Impaired in Mice Lacking Lecithin:Retinol Acyltransferase (LRAT)" The Journal of Biological Chemistry, 280(42): 35647-35657 (Oct. 21, 2005).

Owsley et al., "Development of a Questionnaire to Assess Vision Problems under Low Luminance in Age-Related Maculopathy" Investigative Ophthalmology & Visual Science, 47(2): 528-535 (Feb. 2006).

Phelan, J.K. et al., "A Brief Review of Retinitis Pigmentosa and the Identified Retinitis Pigmentosa Genes" Mol Vis. 6:116-124 (2000).

Rao et al., "5-(Trifluoromethyl)bacteriorhodopsin Does Not Translocate Protons" J. Am. Chem. Soc. 108:6077-78 (1986).

Redmond, T.M. et al., "Rpe65 is Necessary for Production of 11-cis-vitamin A in the Visual Retinal Cycle" Nat Genet. 20(4):344-351 (1998).

Reid et al., "Mass Spectral Analysis of Eleven Analogs of Vitamin A1" Lipids, 8(10): 558-565.

Renk, et al., "A Rhodopsin Pigment Containing a Spin-Labeled Retinal" J. Am. Chem. Soc. 109: 6163-6168 (1987).

Roman et al., "Full-field stimulus testing (EST) to quantify visual perception in severely blind candidates for treatment trials" Physiol. Meas. 28: N51-N56 (2007).

Sekiya, et al., "Effect of modification of the chromophore in retinochrome" Biophys. Chem. 56:31-39 (1995).

Sen et al., "Synthesis and Binding Studies of a Photoaffinity Label for Bovine Rhodopsin" J. American Chem. Soc. 104:3214-16 (1982).

Spaeth, Ophthalmic Surgery: Principles of Practice, Ed., W. B. Sanders Co., Philadelphia, Pa., U.S.A., pp. 85-87 (1990).

Steinberg et al., "Isomer Composition and Spectra of the Dark and Light Adapted Forms of Artificial Bacteriorhodopsins" Photochemistry and Photobiology, 54(6) 969-976 (1991).

Tan et al., "Absolute Sense of Twist of the C12-Cl3 Bond of the Retinal Chromophore in Bovine Rhodopsin Based on Exciton-Coupled CD Spectra of 11,12-Dihydroretinal Analogues" Anxeu Cben7 Inr Ed Engl 36(19): 2089-2093 (1997).

Thompson, D.A. et al., "Mutations in the Gene Encoding Lecithin Retinol Acyltransferase Are Associated With Early-Onset Severe Retinal Dystrophy" Nat Gen 28:123-4 (2001).

Travis, G.H. et al., "Diseases Caused by Defects in the Visual Cycle: Retinoids as Potential Therapeutic Agents" Annu Rev Pharmacol Toxicol 47:469-512 (2007).

Tsujikawa M. et al., "Age at Onset Curves of Retinitis Pigmentosa" Arch Ophthalmol 126(3) 337-340 (2008).

Van Hooser et al., "Rapid restoration of visual pigment and function with oral retinoid in a mouse model of childhood blindness" PNAS, 97(15): 8623-8628 (Jul. 18, 2000).

von Lintig, J. et al., "The biochemical and structural basis for trans-to-cis isomerization of retinoids in the chemistry of vision" Trends Biochem Sci (Feb. 24, 2010).

Wada et al., "Retinoids and related compounds. Part 20.1 Synthesis of (11Z)-8,18-ethanoretinal and a conformational study of the rhodopsin chromophore" J. Chem. Soc., Perkin Trans. 1: 1773-1777 (1997).

Wada et al., "Retinoids and related compounds. Part 26.1 Synthesis of (11Z)-8,18-propano- and methano-retinals and conformational study of the rhodopsin chromophore" J. Chem. Soc., Perkin Trans. 1: 2430-2439 (2001).

Wingerath et al., "Analysis of Cyclic and Acyclic Analogs of Retinol, Retinoic Acid, and Retinal by Laser Desorption Ionization-, Matrix-Assisted Laser Desorption Ionization±Mass Spectrometry, and UV/Vis Spectroscopy" Analytical Biochemistry 272: 232-242 (1999).

Yan et al., "Mechanism of activation of sensory rhodopsin I: Evidence for a steric trigger" Proc. Natd. Acad. Sci. USA, 88: 9412-9416 (Nov. 1991).

Yoshizawa et al., "Photochemistry of Iodopsin" Nature, 214: 566-571 (May 6, 1967).

Van Hooser et al., "Recovery of Visual Functions in a Mouse Model of Leber Congenital Amaurosis" The Journal of Biological Chemistry, 277(21): 19173-1918 (May 24, 2002).

Acland GM, et al. Gene therapy restores vision in a canine model of childhood blindness. Nature Genetics 2001; 28:92-95.

Aleman TS, et al, "Impairment of the transient pupillary light reflex in Rpe65(−/−) mice and humans with leber congenital amaurosis," Investigative Ophthalmology & Visual Science, 45(4):1259-1271 (2004).

Crescitelli et al., "Can Isorhodopsin be produced In the living rat?" Vision Res., 13(12):2515-2525 (1973).

Fazzi E, et al. Leber's congenital amaurosis: an update. Eur J Paediatr Neurol 2003; 7:13-22.

Fazzi E, et al. Response to pain in a group of healthy term newborns: behavioral and physiological aspects. Functional Neurology 1996; 11:35-43.

Hamel CP, et al., "Molecular cloning and expression of RPE65, a novel retinal pigment epithelium-specific microsomal protein that is post-transcriptionally regulated in vitro," J Biol Chem, 268(21):15751-15757 (1993).

International Search Report mailed Nov. 3, 2011 for PCT/IB2011/001294.

Jin M, et al. Rpe65 is the retinoid isomerase in bovine retinal pigment epithelium. Cell 2005; 122:449-459.

Koenekoop, R.K. at al.: Oral Synthetic cis-Retinoid Therapy in Subjects with Leber Congenital Amauarosis (LCA) due to Lecithin-Retinol Acyltransferase (LRAT) or Retinal Pigment Epithelial 65 Protein (RPE65) Mutations: Preliminary Results of a Phase 1b Open-Label Trial. Poster presented at Annual Meeting of the Association for Researach in Vision and Opthamology (ARVO), May 2011. http://www.qltinc.com/development/products/documents/QLT091001-LCA-ARVO_2011_poster.pdf. See entire document.

Kozlov et al., "Oxidation of Vitamin A Acetate in Soybean Oil," Khimiko-Farmatsevti-cheskii Zhurnal, 10:24-29 (1971) (English translation).

Lorenz B, et al., "Early-onset severe rod-cone dystrophy in young children with RPE65 mutations," Investigative Ophthalmology & Visual Science, 41(9):2735-2742 (2000).

Maeda A, et al., "Role of photoreceptor-specific retinol dehydrogenase in the retinoid cycle in vivo," J Biol Chem, 280(19):18822-18832 (2005).

Maeda T, et al., "A Critical Role of CaBP4 in the Cone Synapse," Investigative Ophthalmology & Visual Science, 46(11):4320-4327 (2005).

(56) References Cited

OTHER PUBLICATIONS

Maeda T, et al., "Loss of cone photoreceptors caused by chromophore depletion is partially prevented by the artificial chromophore prodrug, 9-cis-retinyl acetate," Human Molecular Genetics 18(12): 2277-2287 (2009). Published on-line Apr. 1, 2009.
Marlhens F, et al. Mutations in RPE65 cause Leber's congenital amaurosis. Nature Genetics 1997; 17:139-141.
Moiseyev G. et al., "RPE65 is the isomerohydrolase in the retinoid visual cycle," Proceedings of the National Academy of Sciences of the United States of America,102(35):12413-12418 (2005).
Myhre et al., "Water-miscible, emulsified, and solid forms of retinol supplements are more toxic than oil-based preparations[1-3]," Am. J. Clin. Nutr., 78(6):1152-9 (2003).
Palczewski K. G protein-coupled receptor rhodopsin. Annual Review of Biochemistry 2006; 75:743-767.
Pang JJ, et al. Retinal degeneration 12 (rd12): a new, spontaneously arising mouse model for human Leber congenital amaurosis (LCA). Molecular Vision 2005; 11:152-162.
Pearlman et al., "Visual Pigments of the Vitamin A-Deficient, Thyroidectomized Rat Following Vitamin $A_2$ Administration," Vision Res., 11(3):177-187 (1971).
Perrault I, et al. Leber congenital amaurosis. Mol Genet Metab 1999; 68:200-208.
QLT Inc. Press release: "QLT Announces Results from Phase 1b Trial of QLT091991 in Subjects with Leber Congenital Amaurosis," May 3, 2011 (May 2, 2011). http://www.qltinc.com/newsCenter/2011/110503.htm. See entire document.
Redmond TM, et al., "Mutation of key residues of RPE65 abolishes its enzymatic role as isomerohydrolase in the visual cycle," Proceedings of the National Academy of Sciences of the United States of America, 102(38):13658-13663 (2005).
Ridge KD et al. Visual rhodopsin sees the light: structure and mechanism of G protein signaling. J Biol Chem 2007; 282(13):9297-9301.
Taha E I. et al. Preparation and in vitro characterization of self-nanoemulsified drug delivery system (SNEDDS) of all-trans-retinol acetate. International Journal of Pharmaceutics. 2004; 285(1-2): 109-119.
Thompson DA, et al., "Genetics and phenotypes of RPE65 mutations in inherited retinal degeneration," Investigative Ophthalmology & Visual Science, 41(13):4293-4299 (2000).
Wrigstad A, et al. Ultrastructural changes of the retina and the retinal pigment epithelium in Briard dogs with hereditary congenital night blindness and partial day blindness. Experimental Eye Research 1992; 55:805-818.
Yanai D, et al., "Visual performance using a retinal prosthesis in three subjects with retinitis pigmentosa," American Journal of Ophthalmology, 143(5):820-827 (2007).
Yoshikami et al., "Visual Pigments of the Vitamin A-Deficient Rat Following Vitamin $A_2$ Administration," Vision Res., 9(6):633-646 (1969).
Gearhart PM, Gearhart C, Thompson DA, Petersen-Jones SM. "Improvement of visual performance with intravitreal administration of 9-cis-retinal in Rpe65-mutant dogs" Arch Ophthalmol 2010; 128(11): 1442-8.
Teelmann, K "Retinoids: Toxicity and Teratogenicity to Date," Pharmac. Ther., vol. 40, pp. 29-43 (1989).
Gerber, LE et al "Changes in Lipid Metabolism During Retinoid Administration" J. Amer. Acad. Derm., vol. 6, pp. 664-674 (1982).
Allen LH "Estimating the Potential for Vit A Toxicity in Women and Young Children" J. Nutr., vol. 132, pp. 2907-2919 (2002).
Silverman, AK "Hypervitaminosis A Syndrome: A Paradigm of Retinoid Side Effects", J. Am. Acad. Derm., vol. 16, pp. 1027-1039 (1987).
Zech LA et al. "Changes in Plasma Cholesterol and Triglyceride Levels After Treatment with Oral Isotretinoin" Arch. Dermatol., vol. 119, pp. 987-993 (1983).
Fan J. et al. "Light Prevents Exogenous 11-cis Retinal from Maintaining Cone Photoreceptors in Chromophore-deficient Mice", Invest. Ophthalmol.Vis Sci. Jan. 12, 2011, 10-6437.
den Hollander, A. I. et al., Prog Ret Eye Res 27:391-419, (2008).

De Marchi et al. "Effects of isotretinoin on the metabolism of triglyceride-rich lipoproteins and on the lipid profile in patients with acne" Arch Dermatol Res, pp. 403-408, 2006.
Colenbrander "Visual Standards Aspects and Ranges of Vision Loss with Emphasis on Population Surveys" Report prepared for the International Council of Ophthalmology at the 29th International Congress of Ophthalmology Sydney, Australia, Apr. 2002, pp. 1-33.
Albeck et al., "Factors affecting the absorption maxima of acidic forms of bacteriorhodopsin: A study with artificial pigments" Biophys. J. 56:1259-65 (1989).
Bainbridge et al., "Effect of Gene Therapy on Visual Function in Leber's Congenital Amaurosis" The New England Journal of Medicine, www.nejm.org (Apr. 28, 2008).
Batten, M.L. et al., "Lecithin-retinol Acyltransferase Is Essential for Accumulation of All-trans-Retinyl Esters in the Eye and in the Liver" J Biol Chem 279:10422-32 (2004).
Batten ML et al. "Pharmacological and rAAV Gene Therapy Rescue of Visual Functions in a Blind Mouse Model of Leber Congenital Amaurosis" PLO-S Medicine, 2:333 (2005).
Beischel, et al., "Azidotetrafluorophenyl Retinal Analogue: Synthesis And Bacteriorhodopsin Pigment Formation" Photochemistry and Photobiology, 60(1): 64-68 (1994).
Berson, E.L., et al., "A Randomized Trial of Vitamin A and Vitamin E Supplementation for Retinitis Pigmentosa" Arch Ophthalmol 111, 761-772 (1993).
Birch et al., "Validity and Reliability of the Children's Visual Function Questionnaire (CVFQ)" J AAPOS, 11(5): 473-479 (Oct. 2007).
Boehm et al., "Photoaffinity Labeling Studies of Bacteriorhodopsin with [15-3H]-3-Diazo-4-keto-all-trans-retinal" J. Am. Chem. Soc., 112: 1719-1182 (1990).
Borhan et al., "Chemoenzymatic Synthesis of 11-cis-Retinal Photoaffinity Analog by Use of Squid Retinochrome" J. Am. Chem. Soc., 119: 5758-5759 (1997).
Borhan, et al., "Efficient Synthesis of 11-cis-Retinoids" Chemistry (Europe) 5:1172-75 (1999).
Caldwel et al., "Synthesis of Retinals with Eight- and Nine-Membered Rings in the Side Chain. Models for Rhodopsin Photobleaching Intermediates" J. Org. Chem., 58: 3533-3537 (1993).
Colmenares et al., "11,12-Difluororhodopsin and Related Odd-Numbered Fluororhodopsins. The Use of JF,F for Following a Cis-trans Isomerization Process" J. Am. Chem. Soc., 121: 5803-5804 (1999).
Crescitelli et al., "The spectral properties and photosensitivities of analogue photopigments regenerated with 10- and 14-substituted retinal analogues" Proc. R. Soc. Lond. B 233: 55-76 (1988).
Crouch et al., "Opsin pigments formed with acyclic retinal analogues Minimum 'ring portion' requirements for opsin pigment formation" FEBS 158:1 (1983).
Crouch, "Yearly Review Studies of Rhodopsin and Bacteriorhodopsin Using Modified Retinals" Photochemistry and Photobiology, 44(6): 803-807 (1986).
Ebrey et al., "Properties of Several Sterically Modified Retinal Analogs and Their Photosensitive Pigments", Biochemistry 14:3933-41 (1975).
Eyring et al., "Assignment and Interpretation of Hydrogen Out-of-Plane Vibrations in the Resonance Raman Spectra of Rhodopsin and Bathorhodopsin" Biochemistry 21:384-93 (1982).
Filipek S. et al., "G Protein-Coupled Receptor Rhodopsin: A Prospectus" Annu Rev Physiol 65:851-79 (2003).
Fujimoto et al., "On the Bioactive Conformation of the Rhodopsin" Chemistry 7:4198-204 (2001).
Fujimoto et al., "Solution and Biologically Relevant Conformations of Enantiomeric 11-cis-Locked Cyclopropyl Retinals" J. Am. Chem. Soc., 124: 7294-7302 (2002).
Gartner et al., "Quantum Yield Of Chapso-Solubilized Rhdopsin And 3-Hydroxy Retinal Containing Bovine Opsin" Photochemistry and Photobiology, 54(6): 1047-1055 (1991).
Gollapalli, "All-trans-retinyl Esters are the Substrates for Isomerization in the Vertebrate Visual Cycle" D.R. et al., Biochemistry. 42(19):5809-5818 (2003).
Gu S.M. et al., "Mutations in RPE65 Cause Autosomal Recessive Childhood-onset Severe Retinal Dystrophy" Nat Gen 17:194-7 (1997).

(56) References Cited

OTHER PUBLICATIONS

Han et al., "The C9 methyl group of retinal interacts with glycine-121 in rhodopsin" Proc. Natl. Acad. Sci. USA, 94: 13442-13447 (Dec. 1997).
Hiraki et al., "Bacteriorhodopsin Analog Regenerated with 13-Desmethyl-13-Iodoretinal" Biophys. J. 83:3460-69 (2002).
Hirano et al., "Constraints of Opsin Structure on the Ligand-binding Site: Studies with Ring-fused Retinals" Photochemistry and Photobiology, 76(6): 606-615 (2002).
Hu et al., "Unbleachable Rhodopsin with an 11-cis-Locked Eight-Membered Ring Retinal: The Visual Transduction Process" Biochemistry, 33: 408-416 (1994).
Imai et al., "Probing for the Threshold Energy for Visual Transduction: Red-Shifted Visual Pigment Analogs from 3-Methoxy-3-Dehydroretinal and Related Compounds" Photochemistry and Photobiology, 70(1) 111-115 (1999).
Imamoto et al., "Structure around C6-C7 Bond of the Chromophore in Bathorhodopsin: Low-Temperature Spectroscopy of 6s-cis-Locked Bicyclic Rhodopsin Analogs" Biochemistry 35:6257-62 (1996).
Imanishi et al., "Noninvasive two-photon imaging reveals retinyl ester storage structures in the eye" The Journal of Cell Biology, 164(3): 373-383 (Feb. 2, 2004).
Jackson, G.R. et al,. "Aging and Dark Adaptation" J. Vision Research 39: 3975-3982 (1999).
Jacobson, S.G., et al., "Night Blindness in Sorsbys Fundus Dystrophy Reversed by Vitamin A" Nat Genet 11, 27-32 (1995).
Jacobson et al., "Defining the Residual Vision in Leber Congenital Amaurosis Caused by RPE65 Mutations" Investigative Ophthalmology & Visual Science, 50(5): 2368-2375 (May 2009).
Jang et al., "Mechanism of Rhodopsin Activation as Examined with Ring-constrained Retinal Analogs and the Crystal Structure of the Ground State Protein" The Journal of Biological Chemistry, 276(28): 26148-26153, (Jul. 13, 2001).
Karnaukhova et al., "Bioactivity of Visual Pigments with Sterically Modified Retinal Analogs" Bioorganic Chemistry 27:372-82 (1999).
Klein et al., "Psychophysical assessment of low visual function in patients with retinal degenerative diseases (RDDs) with the Diagnosys full-field stimulus threshold (D-FST)" Doc Ophthalmol, 119:217-224 (2009).
Koutalos "Regeneration of Bovine and Octopus Opsins in Situ with Natural and Artificial Retinals" Biochemistry 28:2732-39 (1989).
Kuksa et al., "Biochemical and Physiological Properties of Rhodopsin Regenerated with 11-cis-6-Ring- and 7-Ring-retinals" The Journal of Biological Chemistry, 277(44): 42315-42324 (Nov. 1, 2002).
Lamb, T.D. et al,. "Dark Adaptation and the Retinoid Cycle of Vision" J. Prog Retin Eye Res 23, 307-380 (2004).
Lewin et al., "Synthesis and Characterization of trans-, 13-cis-, and 11-cis, 13-cis-12-(Hydroxymethyl)retinols" J. Org. Chem., 49: 649-652 (1984).
Lewis et al., "Steric Barrier to Bathorhodopsin Decay in 5-Demethyl and Mesityl Analogues of Rhodopsin" J. Am. Chem. Soc., 123: 10024-10029 (2001).
Lin et al., "Vibrational Assignment of Torsional Normal Modes of Rhodopsin: Probing Excited-State Isomerization Dynamics along the Reactive C11dC12 Torsion Coordinate" J. Phys. Chem. B, 102: 2787-2806 (1998).
Maeda, T. et al., "Evaluation of 9-cis-Retinyl Acetate Therapy in Rpe65−/− Mice" Investigative Ophthalmology & Visual Science (50)9: 4368-4378 (2009).
Maguire et al., "Safety and Efficacy of Gene Transfer for Leber's Congenital Amaurosis" N Engl J Med, 358: 2240-8 (2008).
Maguire et al., "Safety and Efficacy of Gene Transfer for Leber Congenital Amaurosis" Supplementary Appendix from N Engl J Med, 358: 2240-8 (2008).
Margaron, P., Castaner, L., and Narfstrom, K. "Evaluation of Intravitreal cis-Retinoid Replacement Therapy in a Canine Model Of Leber's Congenital Amaurosis" Invest Ophthalmol Vis Sci; 50:E-Abstract 6280 (2009).
Marlhens, F. et al., "Autosomal recessive retinal dystrophy associated with two novel mutations in the RPE65 gene" Eur J Hum Genet. 6(5):527-531 (1998).
Maxwell et al., "Photodynamic Response In *Rhodotorula glutinis* In The Absence Of Added Sensitizers" Photochemistry and Photobiology, vol. 13, pp. 259-273 (1971).
McBee, J.K. et al., "Confronting Complexity: the Interlink of Phototransduction and Retinoid Metabolism in the Vertebrate Retina" Prog Retin Eye Res 20, 469-529 (2001).
Mizukami et al., "Photoisomerization mechanism of the rhodopsin chromophore: Picosecond photolysis of pigment containing 11-cis-locked eight-membered ring retinal" Proc. Natl. Acad. Sci. USA, 90: 4072-4076 (May 1993).
Maeda et al., "Effects of Long-Term Administration of 9-cis-Retinyl Acetate on Visual Function in Mice", Investigative Ophthalmology & Visual Science, Jan. 2009, vol. 50, No. 1, pp. 322-333.
Accutane Label, NDA 18-662/S-056, pp. 11-55 (2005).
Extended European Search Report for EP 11771664.7 mailed Aug. 19, 2013 (11 pgs).
Koenekoop, RK., "Oral synthetic cis-retinoid therapy in subjects with Leber Congenital Amaurosis (LCA) due to Lecithin:Retinol Acyltransferase (LRAT) or Retinal Pigment Epithelial 65 Protein (RPE65) mutations: Preliminary Results of a Phase Ib Open Label Trial" Invest. Ophthalmol. Vis. Sci. 2011; 52: E-Abstract 3323.
Maeda et al., "QLT91001, a 9-*cis*-Retinal Analog, Is Well-Tolerated by Retinas of Mice with Impaired Visual Cycles," Investigative Ophthalmology & Visual Science, 54(1):455-466, (2013).
Perusek et al., "Vitamin A Derivatives as Treatment Options for Retinal Degenerative Diseases," Nutrients, 5:2646-2666 (2013).
Handbook of Pharmaceutical Excipients, Fifth Ed., Soybean Oil, pp. 722-723 (3 pgs total) (2006).
Revised, Pharmaceutical Additive Handbook (Kaitei Iyakuhin Handobukku), Yakuji Nippo Limited, Feb. 28, 2007, pp. 753-755.
Ablonczy et al., "11-cis-retinyl reduces constitutive opsin phosphorylyzation and improves quantum catch in retinoid-deficient mouse rod photoreceptors", J. Biol. Chem., vol. 277, pp. 40491-40498 (2002).
Acland et al., "Long-term restoration of rod and cone vision by single dose rAAV-mediated gene transfer to the retina in a canine model of childhood blindness", Mol. Ther., vol. 12, No. 6, pp. 1072-1082 (2005).
Aggarwal et al., "2-Halogeno-1,3-dithiane 1,3-dioxide: a diastereoselective carbonyl anion equivalent in reactions with aldehydes", J. Chem. Soc., vol. 1, pp. 11-19 (1997).
Ames et al., "Biomedical studies on vitamin A. XIV. Biopotencies of Geometric Isomers of Vitamin A Acetate in the Rat", J. Am. Chem. Soc., vol. 77. pp. 4134-4136 (1955).
Asato et al., "Flourinated rhodopsin analogues from 10-flouro-and 14-flouroretinal", J. Am. Chem. Soc., vol. 100, No. 18, pp. 5957-5960 (1978).
Baehr et al., "The retinoid cycle and retina disease", Vision Research, vol. 43, pp. 2957-2958 (2003).
BASF, Technical Information: Retinol 50c, 15d, and 10s. May 2005.
Bernstein et al., "Biochemical characterization of the retinoid isomerase system of the eye", J. Biol. Chem., vol. 262, No. 35, pp. 16848-16857 (1987).
Berson et al., "Disease progression in patients with dominant retinitis pigmentosa and rhodopsin mutations", Invest. Opthalmol. Vis. Sci., vol. 43, No. 9, pp. 3027-3036 (2002).
Berson et al., "Retinitis pigmentosa: unfolding its mystery", Proc. Natl. Sci. USA, vol. 93, pp. 4526-4528 (1996).
Berson, "Treatment of retinitis Pigmentosa with vitamin A", Digital J. Opthamol., vol. 4, No. 7 Massachusetts Eye and Ear Infirmary, Harvard Medical School (1998).
Biesalski et al., "Sensitive Analysis of Retinyl Esters by Isocratic Adsorption Chromatography", J. Clin. Chem. Clin. Biochem., vol. 27, No. 2, pp. 65-74 (1989) Abstract only.
Birnbach et al., "Retinoic acid accelerates photoreceptor cell death by apoptosis in Pro23HIS rhodopsin transgenic mice", Invest. Opthalmol. Vis. Sci., vol. 38, No. 4, pp. s311 (1997).
Bittner et al.," test-retest, within-visit variability of goldmann visual fields in retinitis pigmentosa," Invest Ophthalmol Vis Sci; 52:8042-8046 (2011).

(56) References Cited

OTHER PUBLICATIONS

Bridges, "Vitamin A* and the Role of the Pigment Epithelimn during Bleaching and Regeneration of Rhodopsin in the Frog Eye", Exp. Eye Res., vol. 22, pp. 435-455 (1976).
Buczylko et al., "Mechanisms of opsin activation", J. Biol. Chem., vol. 271, No. 34, pp. 20621-20630 (1996).
Capecchi, "Altering the genome by homologous recombination", Science, vol. 244, No. 4910, pp. 1288-1292 (1989).
Carney and Russell, "Correlation of Dark Adaptation Test Results with Serum Vitamin A Levels in Diseased Adults", J. Nutr., vol. 110, pp. 552-557 (1980).
Caruso et al., "Effects of fenretinide (4-HPR) on dark adaptation", XP002475887; STN Database Accession No. 1998:418096 & Archives of Ophthalmology (Chicago), vol. 116, No. 6, pp. 759-763, Coden: Aropaw; ISSN:0003-9950, (1998) Abstract only.
Chan et al., "Delayed dark adaption caused by nilutamide", J. NeuroOphthalmology, vol. 28, No. 2, pp. 158-159 (2008).
Chapple et al., "Looking at protein misfolding neurodegenerative disease through retinitis pigmentosa", ACNR, vol. 3, Issue 1, pp. 12-13 (2003).
Chatzinoff et al., "Eleven-cis vitamin A in the treatment of retinitis Pigmentosa", Arch. Opthalmol., vol. 80, pp. 417-419 (1968).
Chen et al., "Inherent instability of the retinitis pigmentosa P23H mutant opsin", JBC Papers in Press, Manuscript M114.551713, 31 pages, Latest version can be accessed at http://www.jbc.org/cgi/doi/10.1074/jbc.M114.551713, Published Feb. 10, 2014.
Christoforidis, " Volume Of visual field assessed with kinetic perimetry and its application to static perimetry," Clin Ophthalmol, 5:535- 541 (2011).
Cideciyan et al., " Human gene therapy for RPE65 isomerase deficiency activates the retinoid cycle of vision but with slow rod kinetics," PNAS USA., 105:15112-15117 (2008).
Cideciyan et al., "Rod and cone visual cycle consequences of a null mutation in the 11-cis-retinol dehydrogenase gene in man", Vis. Neurosci., vol. 17, No. 5, pp. 667-678 (2000).
Congdon et al., "Responsiveness of dark-adaptation threshold to vitamin A and β-carotene supplementation in pregnant and lactating women in Nepal", Am. J. Clin. Nutr., vol. 72, pp. 1004-1009 (2000).
Corson et al., "Sensitization of bleach rod photoreceptors by 11-cis-locked analogues of retinal", PNAS USA, vol. 87, pp. 6823-6827 (1990).
Crouch and Katz, "The effect of retinal isomers on the ver and erg of vitamin A deprived rats", Vision Res., vol. 20, pp. 109-115 (1980).
Crouch et al., "Cycloheptatrienylidene analog of 11-cis retinal", Invest. Opthalmol. Vis. Sci., vol. 25, pp. 419-418 (1984).
Crouch et al., "Inhibition of rhodopsin regeneration of cyclohexyl derivatives", Vision Research, vol. 22, No. 12, pp. 1451-1456 (1982).
Crouch et al., "Photosensitive pigments formed with rat opsin", Investigative Opthalmology, vol. 15, No. 10, pp. 872-875 (1976).
Dahl et al., "Stability of vitamins in soybean oil fat emulsion under conditions simulating intravenous feeding of neonates and children" Journal of Parenteral Enteral Nutrition, 18:234-239 (1994).
De Grip et al., "10 20-methanorhodopsins (7E, 9E, 13E)-10 20 methanorhodopsin and (7E, 9Z, 13Z)-10 20 methanorhodopsin 11-cis-locked rhodopsin analog pigments with unusual thermal and photostability", Eur. J. Biochem., vol. 191, No. 1, pp. 211-220 (1990).
Delange et al., "An additional methyl group at the 10-position of retinal dramatically slows down the kinetics of the rhodopsin photocascade", Biochemistry, vol. 37, No. 5, pp. 1411-1420 (1998).
Dorwald, *Side Reactions in Organic Synthesis: A Guide to Successful Synthesis Design*, Wiley-VCH Verlag GmbH & Co. KGaA, Weinheim, Preface page IX, (2004).
Drachev et al., "An investigation of the electrochemical cycle of bacteriorhodopsin analogs with the modified ring", Arch. Biochem. Biophys., vol. 270, No. 1, pp. 184-197 (1989).
Driessen et al., "Disruption of the 11-cis-retinol dehydrogenase gene leads to accumulation of cis-retinols and cis-retinyl esters", Mol. Cell Biol., vol. 20, No. 12, pp. 4275-4287 (2000).

European Search Report From related European Patent Application No. EP 04757476, search completed on Apr. 29, 2020.
European Search Report From Related European Patent Application No. EP 11154402, search completed on Sep. 5, 2011.
European Search Report From Related European Patent Application No. EP 11154404, search completed on Sep. 6, 2011.
European Search Report From Related European Patent Application No. EP 11154534, search completed on Sep. 5, 2011.
Fan et al., "Isorhodopsin rather than rhodopsin mediates rod function in RPE65 knock-out mice" PNAS, vol. 100, No. 23, pp. 13662-13667 (2003).
Fukada et al., "Studies on structure and function of rhodopsin by use of cyclopentatrienylidene 11-cis-locked rhodopsin", Biochemistry, vol. 23, No. 24, pp. 5826-5832 (1984).
Futterman et al., "The composition of liver vitamin A ester and the synthesis of vitamin A ester by liver microsomes", J. Biol. Chem., vol. 239, No. 12, pp. 4077-4080 (1964).
Gaffney et al., "Aging and cone dark adaptation", Optom. Vis. Sci., vol. 89, No. 8, pp. 1219-1224 (2012) (Abstract only).
Gao and Hollyfield, "Aging of the human retina" Inv. Opth. Vis. Sci., vol. 33, pp. 1-17 (1992).
Gennaro et al., Remington: the Science and Practice of Pharmacy, $19^{th}$ Edition, Mack Publishing Company, pp. 1528-1529 (1995).
Geroski et al., "Drug delivery for posterior segment eye disease", IOVS, vol. 41, No. 5, pp. 961-964 (2000).
Grant et al., "Treatable forms of retinitis pigmentosa associated with systemic neurological disorders", Int. Opthalmol. Clin., vol. 41, No. 1, (2001) printed from http://www.ncbi.nim.nih.gov/pubmed/11198137 on Jan. 14, 2009 Abstract only.
Grover et al., "Patterns of visual field progression in patients with retinitis pigmentosa," Ophthalmology, 105:1069-1075 (1998).
Haeseleer et al., "Dual-substrate specificity short chain retinol dehydrogenases from the vertebrate retina", J. Biol. Chem., vol. 277, No. 47, pp. 45537-45546 (2002).
Haig et al., "Vitamin A and Rod-Cone Dark Adaption in Cirrhoses of the Liver", Science, vol. 87, No. 2267, pp. 534-536 (1938).
Hartong et al., "Retinitis pigmentosa," Lancet, 368:1795-1809 (2006).
Harvard Health Publications, "The aging eye: preventing and treating eye disease", Harvard Health Publications, 3 pgs. (2011) printed from http://www.health.harvard.edu/special health reports/the Aging Eye on Nov. 5, 2011.
Head, "Natural therapies for ocular disorders, part one: diseases of the retina", Alt. Med. Review, vol. 4, No. 5, pp. 342-359 (1999).
Howard et al., "Comparative distribution, pharmacokinetics and placental permeabilities of all-trans-retinoic acid, 13-cis-retinoic acid, all-trans-4-oxo-retinoic acid, retinyl acetate and 9-cis-retinal in hamsters", Arch. Toxicol., vol. 63, pp. 112-120 (1989).
Huttunen et al., "Prodrugs—from Serendipity to Rational Design", Pharmacological Reviews, vol. 63, No. 3, pp. 750-771 (2011).
Illing et al., "A Rhodopsin mutant linked to autosomal dominant retinitis pigmentosa is prone to aggregate and interacts with ubiquitin proteasome system", J. Biol. Chem., vol. 277, No. 37, pp. 34150-34160 (2002).
International Search Report from related PCT Patent Application No. PCT/US2004/007937 mailed on Dec. 3, 2004, application now published as International Publication No: WO2004/082622, published on Sep. 30, 2004.
International Search Report from related PCT Patent Application No. PCT/US2005/021812 mailed on Dec. 28, 2005, application now published as International Publication No: WO2006/002097, published on Jan. 5, 2006.
International Search Report from related PCT Patent Application No. PCT/US2009/000824 mailed on Nov. 5, 2009, application now published as International Publication No: WO2009/102418, published on Aug. 20, 2009.
Jackson et al., "Aging and scotopic sensitivity", Vis. Res., vol. 38, pp. 3655-3662 (1998).
Jackson et al., "Photoreceptor degeneration and dysfunction in aging and age-related maculopathy", Aging Res. Rev., vol. 1, No. 3, pp. 381396 (2002).

(56) References Cited

OTHER PUBLICATIONS

Jacobson et al., "Identifying photoreceptors in blind eyes caused by RPE65 mutations: Prerequisite for human gene therapy success", PNAS USA, vol. 102, No. 17, pp. 6177-6182 (2005).
Jacobson et al., "Phenotypic Marker for Early Disease Detection in Dominant Late-Onset Retinal Degeneration", IOVS, vol. 42, No. 8, pp. 1882-1890 (2001).
Jacobson et al., "Retinal degenerations with truncation mutations in the cone-rod homeobox (CRX) gene", Invest. Opthalmol. Vis. Sci., vol. 39, No. 12, pp. 2417-2426 (1988).
Jang et al., "Characterization of a dehydrogenase activity responsible for oxidation of 11-cis-retinol in the retinal pigment epithelium of mice with a disrupted RDH5 gene. A model for the human heredity disease fundus albunctatus", J. Biol. Chem., vol. 276, No. 35, pp. 32456-32465 (2001).
Jin et al., "Noncovalent occupancy of the retinal-binding pocket of opsin diminishes bleaching adaption of retinal cones", Neuron, No. 11, pp. 513-522 (1993).
Kefalov et al., "Role of noncovalent binding of 11-cis-retinal to opsin in dark adaption of rod and cone photoreceptors", Neuron, vol. 29, pp. 749-755 (2001).
Kemp et al., "Visual Function and Rhodopsin Levels in Humans with Vitamin a Deficiency", Exp. Eye Res., vol. 46, pp. 185-197 (1988).
Kirillova et al., "Cyclopentene and cyclohexene retinal analogues react differently with bacteriorhodopsin", Chemical Abstracts, vol. 120, pp. 557, (1994) Abstract No. 120:187138 Abstract only.
Koenekoop et al., "Oral 9-cis retinoid for childhood blindness due to Leber congenital amaurosis caused by RPE65 or LRAT mutations: an open-label phase 1b trial", Lancet, 8 pages, Published Online http://dx.doi.org/10.1016/S0140-6736(14)60153-7, Published Jul. 14, 2014.
Kubo et al., "Effect of vitamin a palmitate on vitamin A-deficient rabbits", XP002475885; STN Database Accession No. 2000:172779 & Nippon Ganka Gakkai Zasshi, vol. 103, No. 10, pp. 729-733 Coden:NGZAA6; ISSN: 0029-0203,1999 Abstract only.
Kuksa et al., 'Retinoid cycle in the vertebrate retina: experimental approaches and mechanisms of isomerization, Vision Research, vol. 43, pp. 2959-2981 (2003).
Kupfer et al., "Information for doctors who follow patients with retinitis pigmentosa", National Eye Institute (1993), printed from http://www.nei.nih.gov/news/clinicalalerts/alert-rp.asp on Jan. 15, 2009, 2 pages.
Kuse et al., "Change in retinal rod function in age-related macular degeneration," Japanese Review of Clinical Ophthalmology, vol. 10, No. 100, pp. 59 (English Abstract only) (2006).
Lamb and Pugh, "Phototransduction, Dark Adaptation, and Rhodopsin Regeneration", IOVS, vol. 47, No. 12, pp. 5138-5152 (2006).
Lang, "Ocular drug delivery conventional ocular formulations", Adv. Drug Del. Rev., vol. 16, No. 1, pp. 39-43 (1995).
Lawson et al., "Retinal analog restoration of photophobic responses in a blind chlamydomonas-reinhardtii mutant evidence for an archaebacterial like chromophore in a eukaryotic rhodopsin", Biophysical Journal, vol. 60, No. 6, pp. 1490-1498 (1991).
Li et al., "Delivery of 9-cis retinal to photoreceptors from bovine serum albumin", Photochem. Photobiol., vol. 69, No. 4, pp. 500-504 (1999).
Li et al., "Effect of vitamin a supplementation on rhodopsin mutants threonine-17→methionine and proline-347→serine in transgenic mice and in cell cultures", Proc. Natl. Acad. Sci. USA, vol. 95, pp. 11933-11938 (1998).
Littink et al., "A homozygous frameshift mutation in LRAT causes retinitis punctata albescens," Ophthalmology, 119:1899-1906 (2012).
Liu et al., "The nature of restrictions in the binding site of rhodopsin. A model study", J. Am. Chem. Soc., vol. 106, No. 26, pp. 8298-8300 (1984).
Maeda et al., "Evaluation of the role of the retinal g protein-coupled receptor (RGR) in the vertebrate retina in vivo", Journal of Neurochemistry, vol. 85, pp. 944-956 (2003).

Maeda et al., "Improvement in Rod and Cone Function in Mouse Model of *Fundus albipunctatus* after Pharmacologic Treatment with 9-*cis*-Retinal", IOVS, vol. 47, No. 10, pp. 4540-4546 (2006).
Marmor et al., "Abipunctate retinopathy with cone dysfunction and no abnormality in the RDH5 or RLBP1 genes", Retina, vol. 23, No. 4, pp. 543-546 (2003).
Massoud et al., "Plasma vitamin A and beta-carotene in retinitis pigmentosa", Brit. J. Opthal., vol. 59, pp. 200-204 (1975).
Mata et al.,"Substrate specificity of retinyl ester hydrolase activity in retinal pigment epithelium", Journal of Lipid Research, vol. 39, pp. 604-612 (1998).
Matsukawa et al., "Role of purpurin as a retinal-binding protein in goldfish retina during the early stage of optic nerve regeneration: Its priming action on neurite outgrowth", J. Neurosci., vol. 24, No. 38, pp. 8346-8353 (2004).
Maugard et al., "Enzymatic synthesis of derivatives of vitamin A in organic media", J. Mol. Cat. B, vol. 8, pp. 275-280 (2000).
Maugard et al., "Synthesis of water-soluble retinol derivatives by enzymatic method", Biotechnol. Prog. vol. 18, pp. 424-428 (2002).
Mayo Clinic, "Retinal detachment", 8 pgs. (2010) printed from http://www.mayoclinic.com/health/retinal-detachment/DS00254/Method=print&Dsection=all.
McBee et al., "Isomerization of 11-cis-retinoids to all-trans-retinoids in vitro and in vivo", J. Biol. Chem., vol. 276, No. 51, pp. 48483-48493 (2001).
MedlinePlus, "Diabetic retinopathy", 5 pgs. (2011) printed from http://www.nim.nih.gov/medlineplus/ency/article/00212.htm.
Mendes et al., "Pharmacological manipulation of rhodopsin retinitis pigmentosa", Advances in Experimental Medicine and Biology, Chapter 36, pp. 317-323, DOI 10.1007/978-1-4419-1399-9_36, Springer Science+Business Media, LLC (2010).
Nakamura et al., "A high association with cone dystrophy in fundus albipunctatus caused by mutations of the RDH5 gene", Invest. Opthalmol. Vis. Sci., vol. 41, No. 12, pp. 3925-3932 (2000).
Newton et al., "Structure-Activity Relationships of Retinoids in Hamster Tracheal Organ Culture", Cancer Res., vol. 40, pp. 3413-3425 (1980).
Nishiguchi et al., "A novel mutation (I143NT) in guanylate cyclase-activating protein 1 (GCAP1) associated with autosomal dominant cone degeneration", Invest. Opthalmol. Vis. Sci., vol. 45, No. 11, pp. 3863-3870 (2004).
Noell, "Suitability of retinol, retinal and retinyl palmitate for the regeneration of bleached rhodopsin in the isolated frog retina", XP002486105, STN Database Accession No. 1985:164043 & Vision Research, vol. 24, No. 11, pp. 1615-1622, CODEN:VISRAM; ISSN:0042-6989, (1984) Abstract only.
Noorwez et al., "Pharmacological chaperone-mediated in vivo folding and stabilization of the P23H-opsin mutant associated with autosomal dominant retinitis Pigmentosa", J. Biol. Chem., vol. 278, No. 16, pp. 14442-14450 (2003).
Noorwez et al., "Retinoids assist the cellular folding of the autosomal dominant retinitis Pigmentosa opsin mutant P23H", J. Biol. Chem., vol. 279, No. 16, pp. 16278-16284 (2004).
Norum and Blomhoff, "McCollum Award Lecture, 1992: Vitamin A absorption, transport, cellular uptake, and storage", Am. J. Clin. Nutr., vol. 56, pp. 735-744 (1992).
Ohgane et al., "Retinobenzaldehydes as proper-trafficking inducers of folding-defective p23H rhodopsin mutant responsible for retinitis pigmentosa", Bioorg. Med. Chem., vol. 18, pp. 7022-7028 (2010).
Owsley et al., "Delays in rod-mediated dark adaption in early agerelated maculopathy", Ophthalmology, vol. 108, pp. 1196-1202 (2001).
Owsley et al., "Effect of short-term, high-dose retinol on dark adaption in aging and early age-related maculopathy", Invest. Ophthalmol. Vis. Sci., vol. 47, No. 4, pp. 1310-1318 (2006).
Paik et al., "9-cis-retinoids: biosynthesis of 9-cis-retinoic acid", Biochemistry, vol. 39, No. 27, pp. 8073-8084 (Jul. 2000).
Park et al., " Toward a clinical protocol for assessing rod, cone, and melanopsin contributions to the human pupil response," Invest Ophthalmol Vis Sci, 52:6624-6635 (2011).
Parry et al., "Visual pigment reconstitution in intact goldfish retina using synthetic synthetic retinaldehyde isomers", Vision research, vol. 40, No. 17, pp. 2241-2247 (2000).

(56) References Cited

OTHER PUBLICATIONS

Price et al., "Mislocalization and degradation of human P23H-Rhodopsin-GFP in a knockin mouse model of retinitis pigmentosa", Inv. Opth. Vis. Sci., vol. 52, No. 13, pp. 9728-9736 (2011).
Radomska et al., "The use of some ingredients for microemulsion preparation containing retinol and its esters", XP002475886, STN Database Accession No. 2000:139945 & International Journal of Pharmaceutics, vol. 196, No. 2, pp. 131-134 Coden:IJPHDEI; ISSN; 0378-5173, (2000) Abstract only.
Rao et al., "Isomers of 3, 7, 11-trimethyldodeca-2, 4, 6, 8, 10-pentaenal (A linear analog of retinal) and lower homologues in their interaction with bovine opsin and bacterioopsin", Photochemistry and Photobiology, vol. 41, No. 2, pp. 171-174 (1985).
Rao et al., "Regioselective photo isomerisation of retinolacetate" Tetrahedron Letters, vol. 31, No. 24, pp. 3441-3444 (1990).
Rezabek et al., "Effects of dietary retinyl acetate on the promotion of hepatic enzyme-altered foci by polybrominated biphenyls in initiated rats", Food Chem. Toxicol., vol. 27, No. 8, pp. 539-544 (1989) Abstract only.
Robinson et al., "Opsins with mutations at the site of chromophore attachment constitutively activate transducin but are not phosphorylated by rhodopsin kinase", Proc. Natl. Acad. Sci. USA, vol. 91, No. 12, pp. 5411-5415 (1994).
Rotenstreich et al., "Treatment of a retinal dystrophy, fundus albipunctatus, with oral 9-cis-b-carotene", Br. J. Opthalmol., vol. 94, pp. 616-621 (2010).
Rotenstreich et al.,"Treatment with 9-cis β-carotene-rich powder in patients with retinitis pigmentosa: a randomized crossover trial," Jama Ophthalmol., 131:985-992 (2013).
Russell, "The vitamin A spectrum: from deficiency to toxicity", Am. J. Clin. Nutr., vol. 71, pp. 878-884 (2000).
Sakami et al., "Probing mechanisms of photoreceptor degeneration in a new mouse model of the common form of autosomal dominant retinitis pigmentosa due to P23H opsin mutations", JBC Papers in Press, Manuscript M110.209759, 29 pages, Latest version can be accessed at http://www.jbc.org/cgi/doi/10.1074/jbc.M110.209759, Published Jan. 11, 2011.
Saliba et al., "The cellular fate mutant rhodopsin: quality control, degradation and aggresome formation", J. Cell Science, vol. 115, pp. 2907-2918 (2002).
Sandberg et al., "Clinical expression correlates with location of rhodopsin mutation in dominant retinitis Pigmentosa", Invest. Opthalmol. Vis. Sci., vol. 36, No. 9, pp. 1934-1942 (1995).
Schatz et al., "Fundus albipunctatus associated with compound heterozygous mutations in RPE65," Ophthalmology, 118:888-894 (2011).
Semenova et al., "Stabilization of all-trans-retinol by cyclodextrins: a comparative study using HPLC and fluorescence spectroscopy", XP002475883; STN Database Accession No. 2003:494986 & Journal of Inclusion Phenomena and Macrocyclic Chemistry, vol. Date (2002), vol. 44, No. 1-4, pp. 155-158 CODEN:JIPCF5; ISSN:1388-3127, (2003) Abstract only.
Semenova et al., "Systems for delivery of vitamin a to the retina in retinitis pigmentosa", XP002475884; STN Database Accession No. 2002:438129 & New Insights Into Retinal Degenerative Diseases, [Proceedings of The International Symposium on Retinal Degeneration], 9TH, Durango, CO, United States, (2000), Meeting Date (2000), pp. 105110; Editor (Anderson & Lavail), (2001) Abstract only.
Semple-Rowland et al., "A null mutation in the photoreceptor guanylate cyclase gene causes the retinal degeneration chicken phenotype", Proc. Natl. Acad. Sci. USA, vol. 95, No. 3, pp. 1271-1276 (1998).
Sibulesky et al., "Safety of <7500 RE (<25000 IU) vitamin A daily in adults with retinitis Pigmentosa", Am. J. Clin. Nutr., vol. 69, pp. 656-663 (1999).
Sokal et al., "GCAP1 (Y99C) mutant is constitutively active in autosomal dominant cone dystrophy", Mol. Cell. vol. 2, No. 1, pp. 129-133 (1998).

Soriatane® (acitretin) capsule US Label (2009) and Principal Display Panels (24 pages).
Stecher et al., "Preferential release of *11-cis-retinol* from retinal pigment epithelial cells in the presence of cellular retinaldehyde-binding protein" the Journal of Biological Chemistry, vol. 274, No. 13, pp. 8577-8585 (1999).
Supplementary European Search Report From Related European Patent Application No. EP 05773576, mailed on Aug. 4, 2008.
Targretin® (bexarotene) capsule US Label (2006) (14 pages).
Tarkhov et al., "Study of a structure-property relationship for retinal derivatives taking into account their conformational flexibility", Chemical Abstracts, vol. 128, No. 18, pp. 270 (1998) Abstract No. 128:214600 Abstract only.
Teller et al., "Advances in determination of a high-resolution three-dimensional structure of rhodopsin, a model of G-protein-coupled receptors (GPCRs)", Biochemistry vol. 40, No. 26, pp. 7761-7772 (2001).
The Eye Digest, "Aging eye in the US", 2 pgs. (2011) printed from http://web.archive.org/web/20060810014820/http://www.agingeye.net/mainnews/usaging.php.
Thompson et al., "Genetic defects in vitamin a metabolism of the retinal pigment epithelium", Genetics in Ophthalmology, vol. 37, pp. 141-154 (2003).
Thomson Scientific, London, GB; AN 1995-063773, XP002475888 & JP 06340525 A (Lion Corp); Dec. 13, 1994 Abstract only.
Thomson Scientific, London, GB; AN 1996-408307, XP002475889 & JP 08198746 A (Lion Corp); Aug. 6, 1996 Abstract only.
Thomson Scientific, London, GB; AN 1998-518867, XP002475890 & RU 2106843 C1 (Krasy Med Acad); Mar. 20, 1998 Abstract only.
Toctino™ (alitretinoin) capsule Canadian Product Monograph (2011) (34 pages).
Vesanoid® (tretinoin) capsule US Label (2004) (14 pages).
Vitamin Converter, known vitamin A conversion, 3 pgs., printed from http;//www.robert-forbes.com/resources/vitaminconverter.html on Apr. 19, 2012.
Weiser and Somorjai, "Bioactivity of cis and dicis isomers of vitamin A esters", Internatl. J. Vit. Nutr., vol. 62, pp. 201-208 (1992).
Witkovsky et al., "Formation, conversion, and utilization of isorhodopsin, rhodopsin, and porphyropsin by rod photoreceptors in the xenopus retina", J. Gen. Physiol., vol. 72, pp. 821-836 (1978).
Woodward et al., "The inflow and outflow of anti-glaucoma drugs", Trends Pharm. Sci., vol. 25, Issue 5, pp. 238-241 (2004).
www.wrongdiagnosis.com, "Symptom: night blindness", pp. 1-17 (Jun. 3, 2008).
Yamamoto et al., "Mutations in the gene encoding 11-cis retinol dehydrogenase cause delayed dark adaptation and fundus Albipunctatus", Nat. Genet., vol. 22, No. 2, pp. 188-191 (1999).
Yamamoto et al.,"Important role of the proline residue in the signal sequence that directs the secretion of human lysozyme in saccharomyces cerevisiae", *Biochemistry* , vol. 28, pp. 2728-2732 (1989).
Zankel et al., "Bovine rhodopsin with 11-cis-locked retinal chromophore neither activates rhodopsin kinase nor undergoes conformational change upon irradiation", J. American Chemical Soc., vol. 112, No. 13, pp. 5387-5388 (1990).
Zhang et al., "Structure, alternative splicing, and expression of the human RGS9 gene", Gene, vol. 240, pp. 23-24 (1999).
Zhu et al., "A naturally occurring mutation of the opsin gene (T4R) in dogs affects glycosylation and stability of the G protein-coupled receptor", J. Biol. Chem., vol. 279, No. 51, pp. 53828-53839 (2004).
Imanishi et al., "Retinosomes: New insights into intracellular managing of hydrophobic substances in lipid bodies," The Journal of Cell Biology, 166:447-453 (2004).
Lorenz et al., "A comprehensive clinical and biochemical functional study of a novel RPE65 hypomorphic mutation," Invest Ophthalmol Vis Sci, 49:5235-5242 (2008).
Hisatomi et al., "Critical role of photoreceptor apoptosis in functional damage after retinal detachment", Curr. Eye Res., vol. 24, No. 3, 161172 (2002) Abstract only, 1 pg., printed from http://www.ncbi,nim.nih.gov/pubmed/12221523.
V.G. Belikov, Farmatsevticheskaya khimiya, [Pharmaceutical Chemistry], M., Vysshaya shkola, 1993, pp. 43-47 (Russian language and the English translation).

* cited by examiner

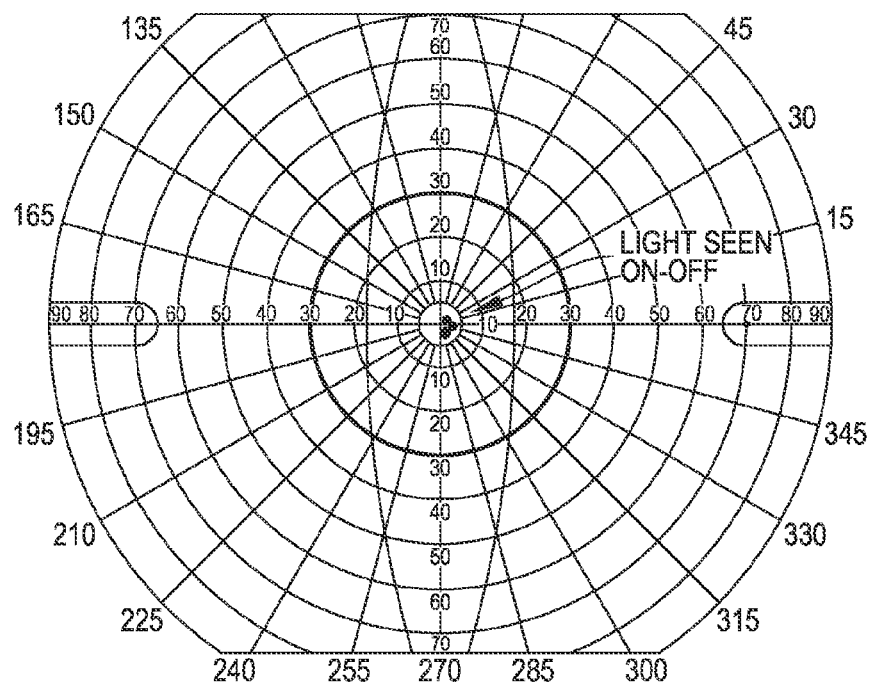
SUBJECT 3: SCREENING OS
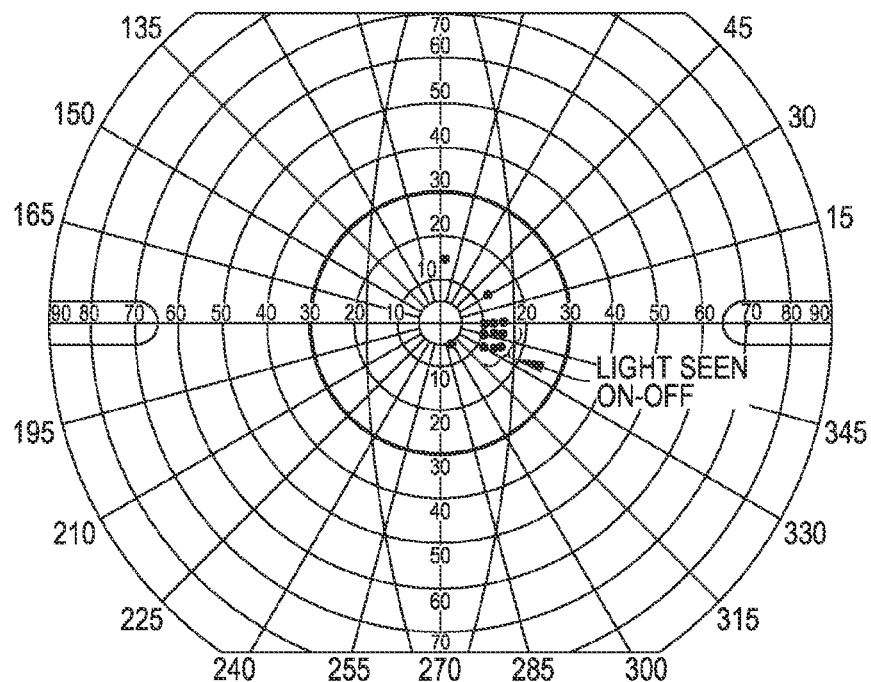
SCREENING OD
FIG. 3A

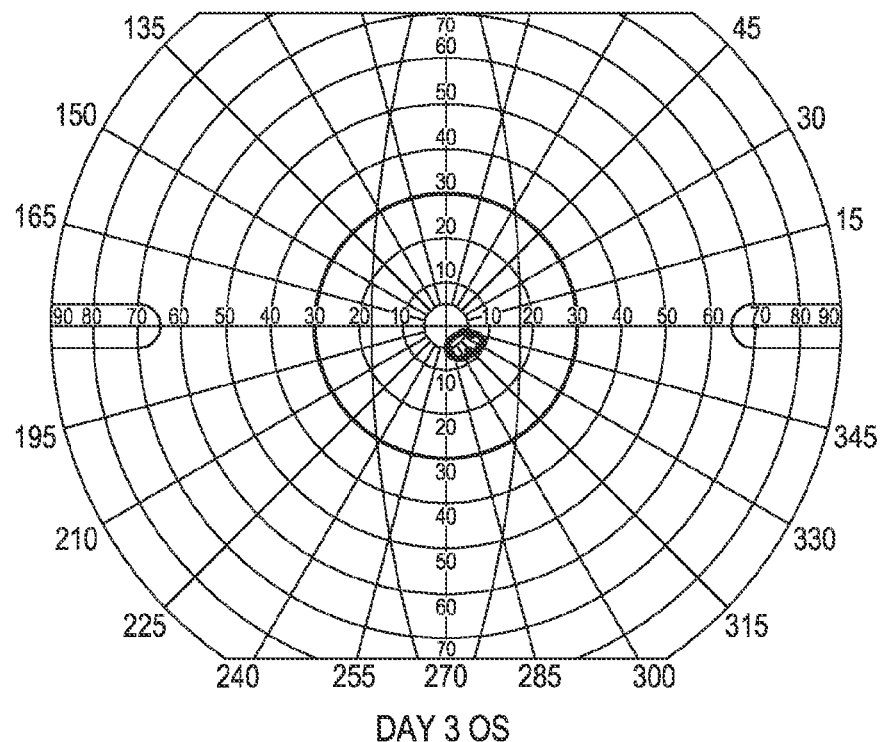
DAY 3 OS
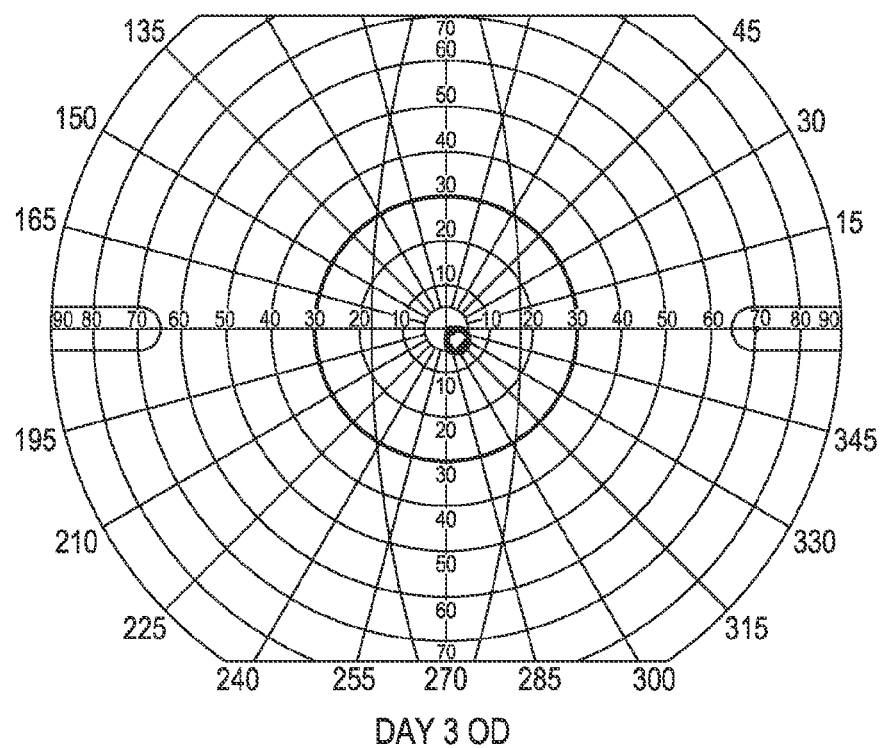
DAY 3 OD
FIG. 3B

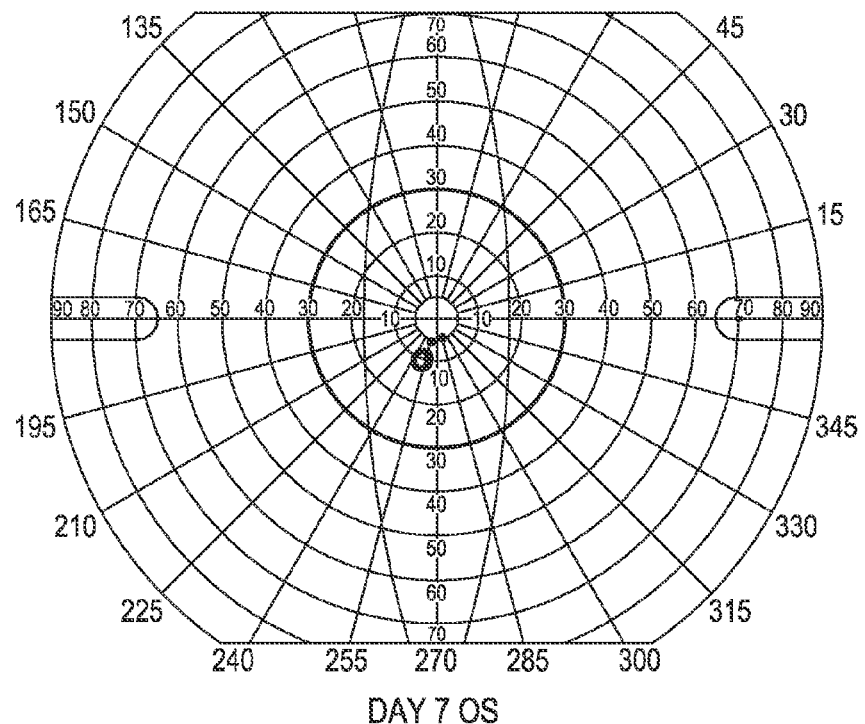
DAY 7 OS
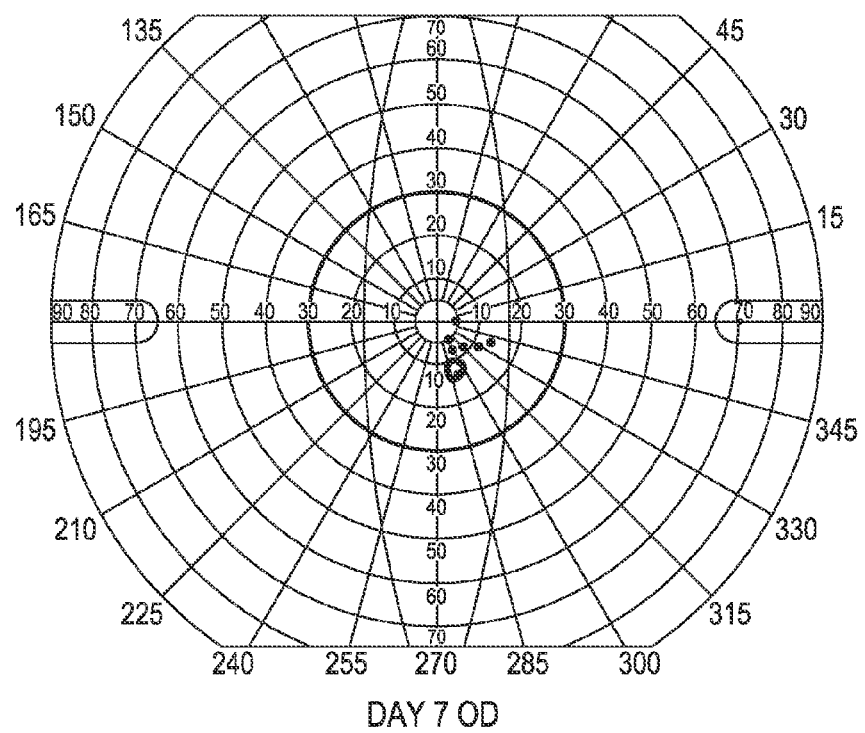
DAY 7 OD
FIG. 3C

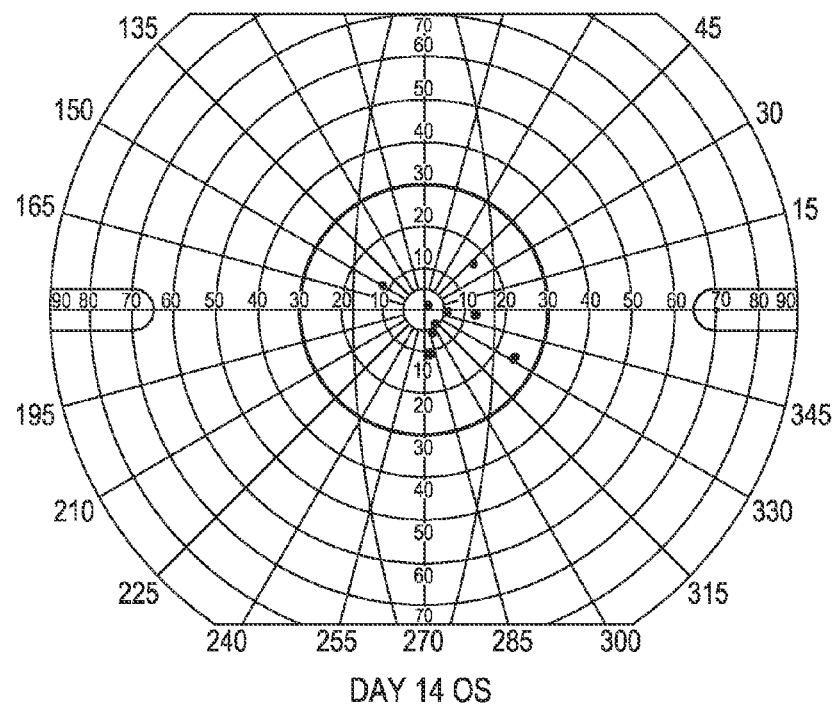
DAY 14 OS
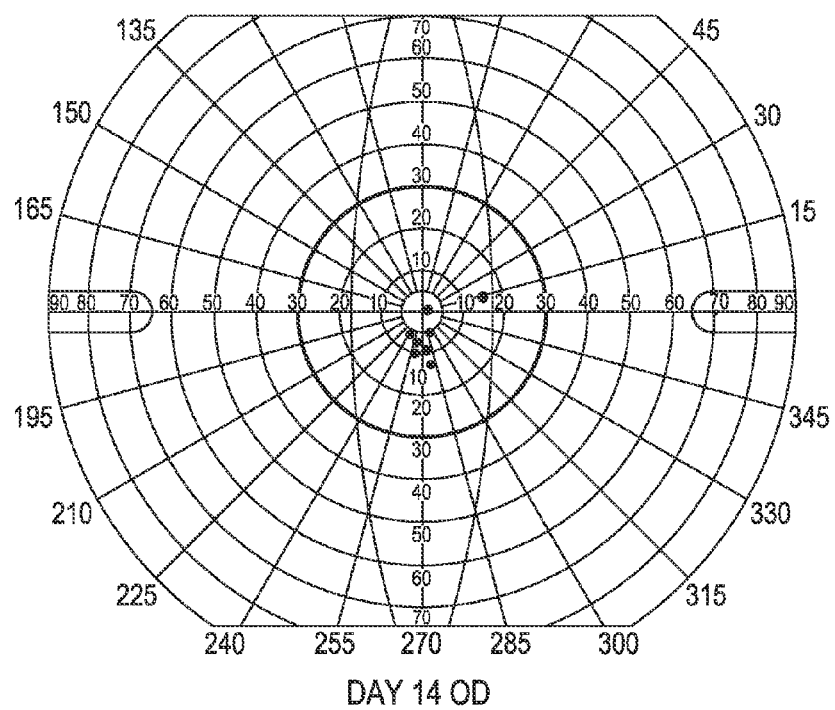
DAY 14 OD
FIG. 3D

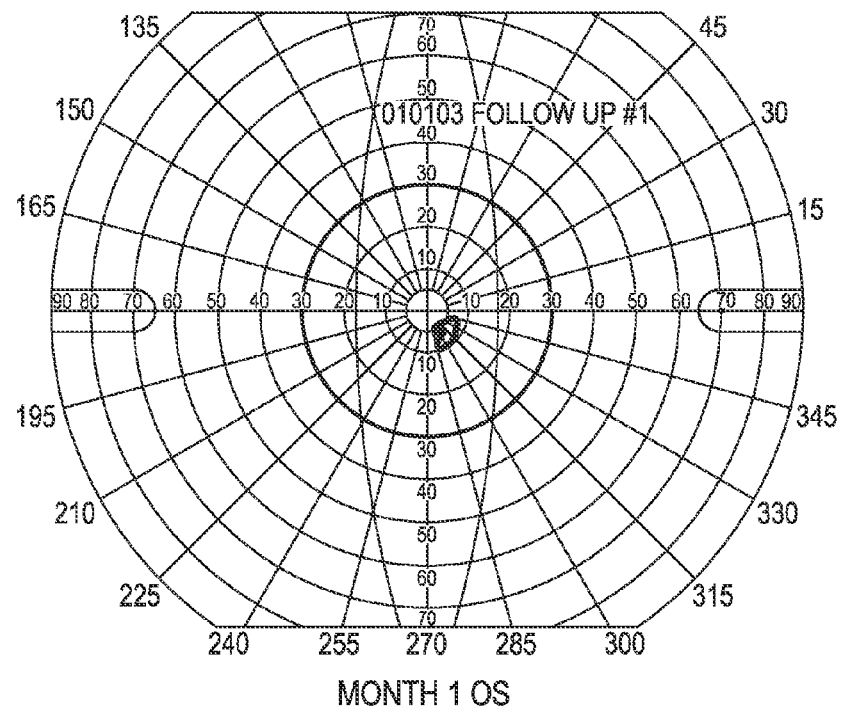
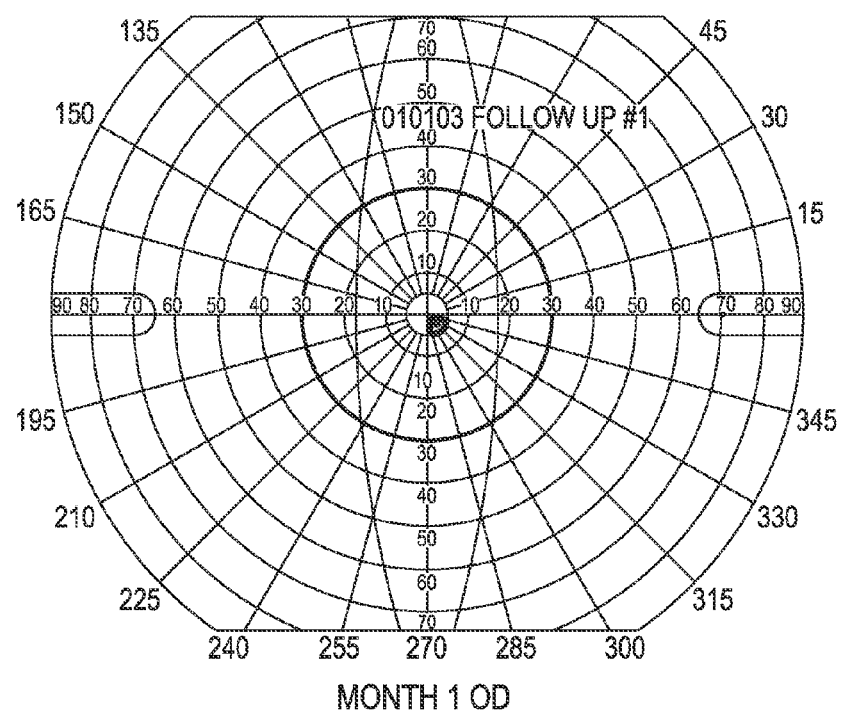
FIG. 3E

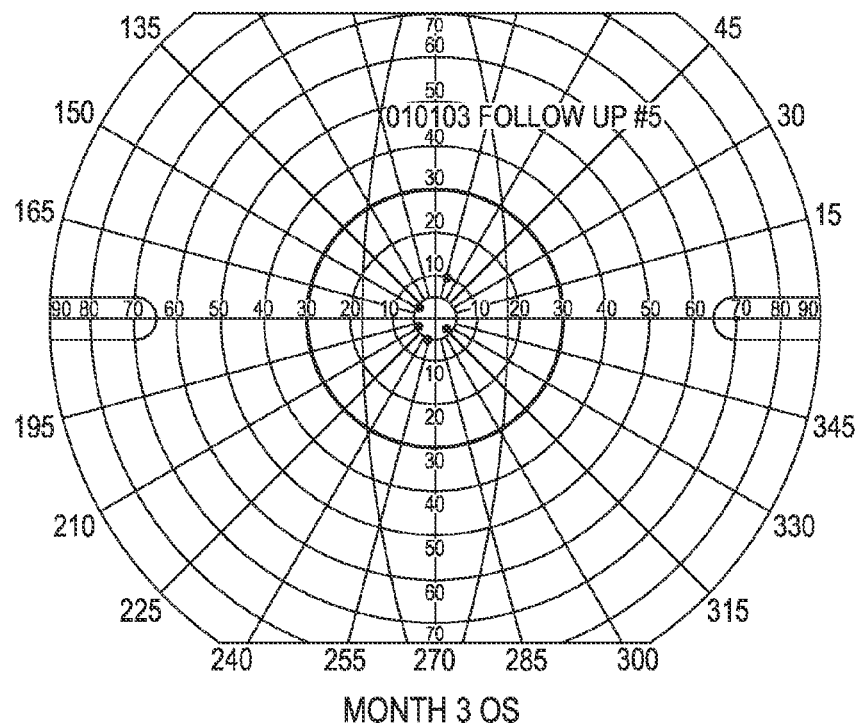
MONTH 3 OS
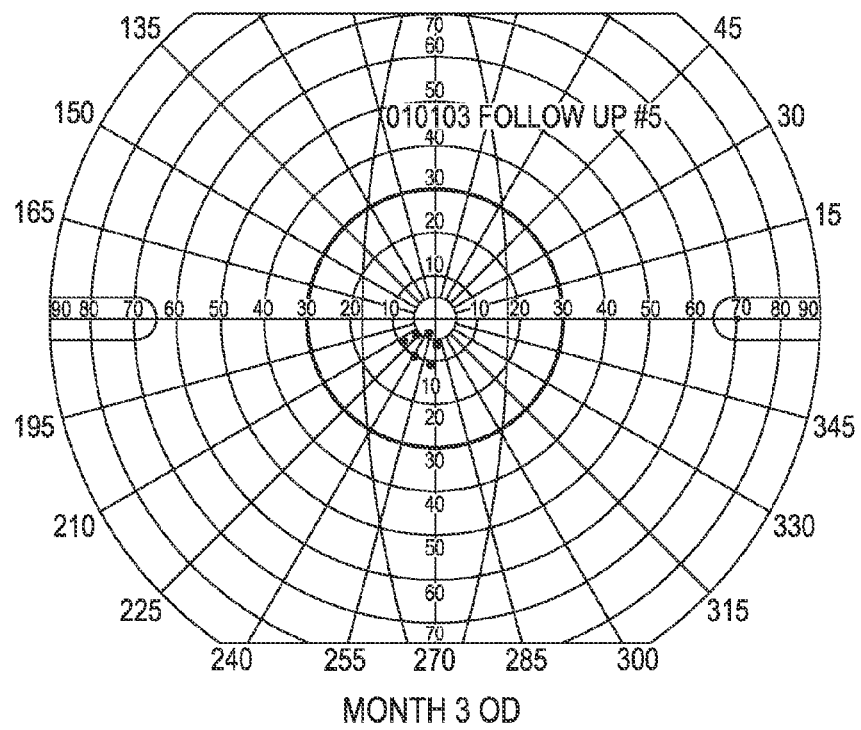
MONTH 3 OD
FIG. 3F

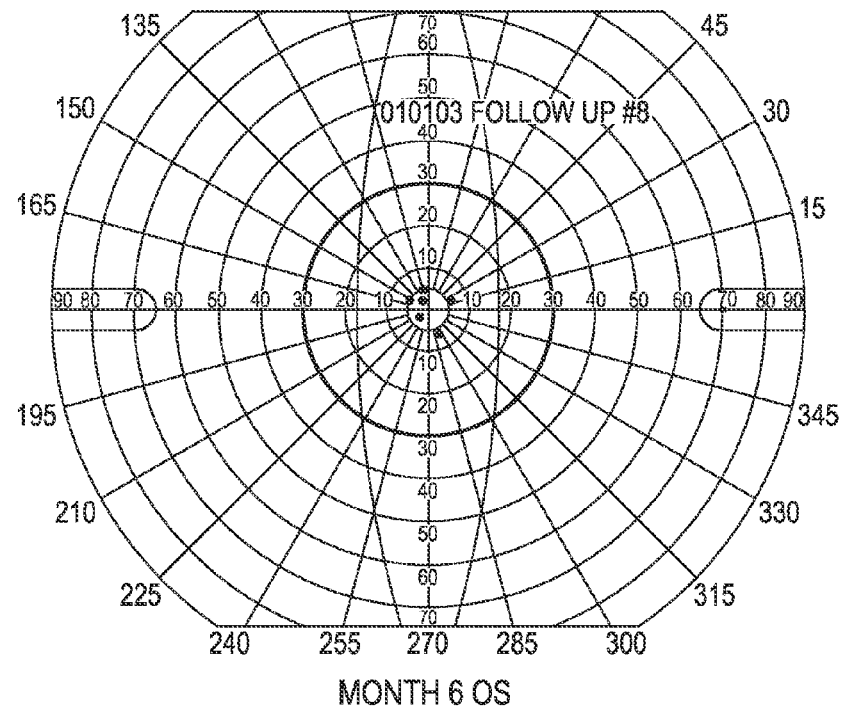
MONTH 6 OS
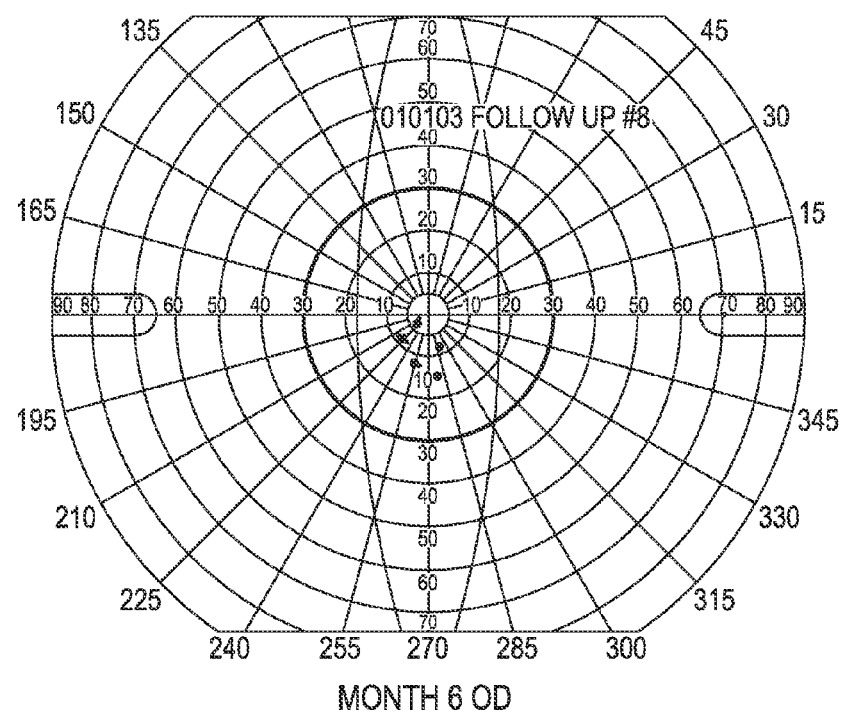
MONTH 6 OD
FIG. 3G

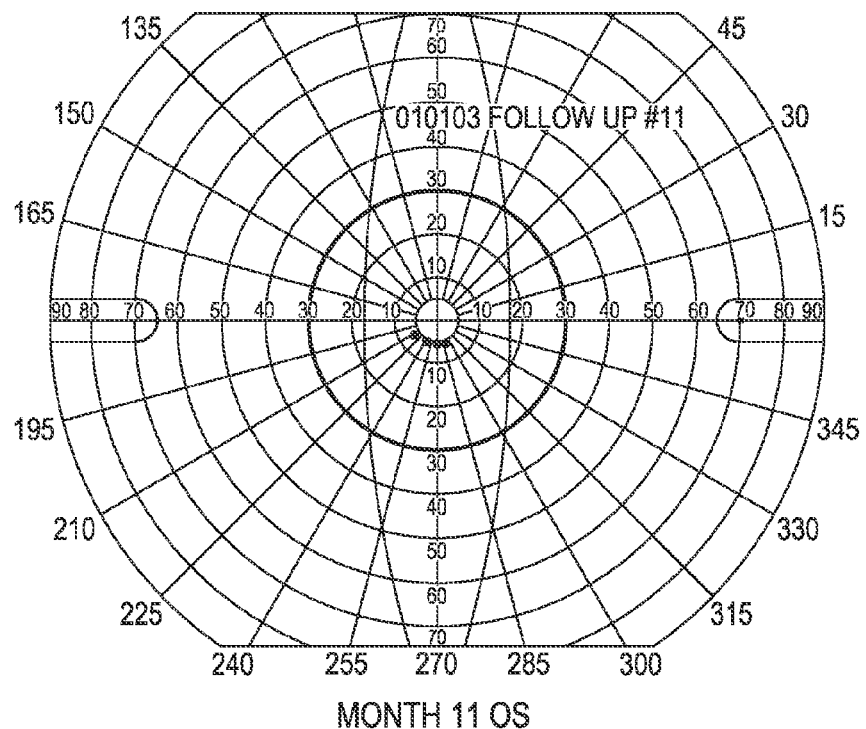
MONTH 11 OS
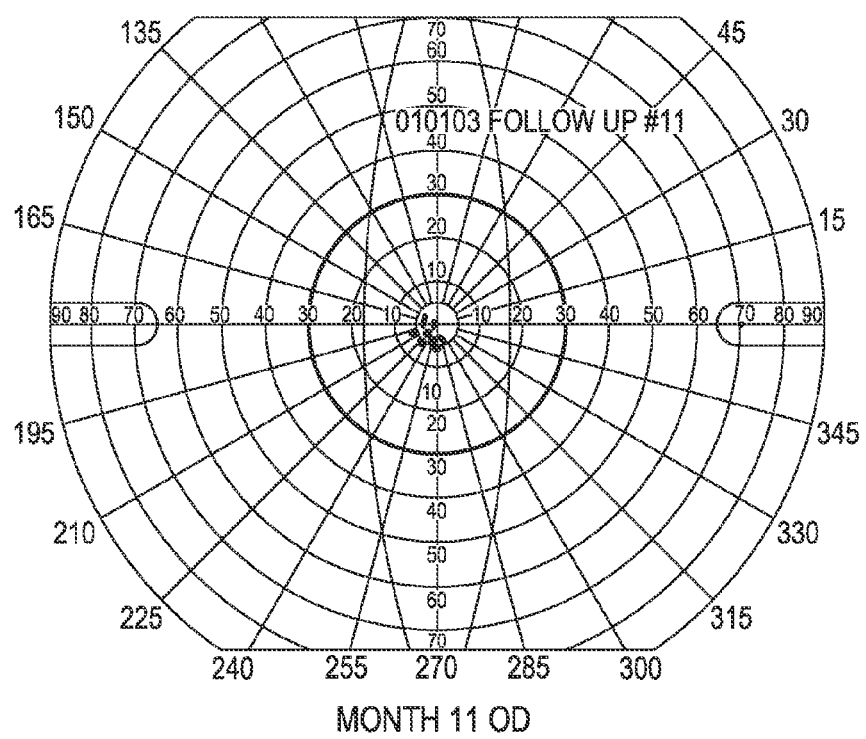
MONTH 11 OD
FIG. 3H

| Subject | Type | Age | Sex | Race | Dose (mg/m²) | Baseline VA (letters) | Best Change from Baseline | Visit |
|---|---|---|---|---|---|---|---|---|
| 1 LCA | *LRAT* | 10 | Female | White | 40 | OD 36 | OD 51 (+15) | Day 8 |
| | HOMOZYGOUS C.217_218DELAT, P.MET73ASPFSX47 | | | | | OS 26 | OS 51 (+25) | Month 4 |
| 2 LCA | *LRAT* | 12 | Male | White | 40 | OD 9 | OD 18 (+9) | Month 6.5 |
| | HOMOZYGOUS C.217_218DELAT, P.MET73ASPFSX47 | | | | | OS 7 | OS 25 (+18) | Day 9 |
| 3 LCA | *LRAT* | 38 | Female | White | 40 | OD 0 | OD 5 (+5) | Month 6 |
| | HOMOZYGOUS C.217_218DELAT, P.MET73ASPFSX47 | | | | | OS 0 | OD 3 (+3) | Month 2.5 |
| 4 LCA | *RPE65* | 31 | Male | Indian | 40 | OD 0 | OD 1 (+1) | Month 2.5 |
| | p.W331X (TGG>TAG) c.992G>A | | | | | OS 15 | OS 21 (+6) | Day 14 |
| 5 LCA | *RPE65* | 13 | Female | Asian | 40 | OD 31 | OD 67 (+36) | Month 4 |
| | Leu67Arg CTG>CGG heterozygous - EPP=3 | | | | | OS 34 | OS 63 (+29) | Day 14 |
| 6 LCA | *RPE65* | 6 | Female | Asian | 40 | OD 64 | OD 70 (+6) | Day 14 |
| | Leu67Arg CTG>CGG heterozygous - EPP=3 | | | | | OS 61 | OS 68 (+7) | |
| 7 LCA | *RPE65* | 21 | Female | Syrian | 40 | OD 60 | OS 60 (0) | Day 14 |
| | -/- V19DEL2BP NT 57+58 | | | | | OS 52 | OS 55 (+3) | Day 9 |
| 8 LCA | *RPE65* | 15 | Female | Brazilian | 10 | OD 28 | OD 32 (+4) | Day 9 |
| | EXON 4 272>A R91Q GA/CT EXON 10 1022T>C L341S TC/AG | | | | | OS 25 | OS 27 (+2) | |
| 9 LCA | *RPE65* | 14 | Female | Hispanic | 10 | OD 37 | OD 51 (+14) | Day 14 |
| | EXON 4 272G, EXON 10 1022T | | | | | OS 47 | OD 46 (-1) | |
| 10 RP | *LRAT* | 28 | Male | Indian | 40 | OD 71 | OD 82 (+11.5) | Day 9 |
| | HOMOZYGOUS EXON 2 C.525T>A; P.SER175ARG | | | | | OS 60 | OS 74 (+14.5) | Month 1.5 |
| 11 RP | *LRAT* | 41 | Male | White | 40 | OD 0 | No change | Day 14 |
| | HOMOZYGOUS EXON 2 C.181T>A3 P.TYR61ASP | | | | | OS 1.5 | OD 26 (+24.5) | |

*FIG. 6*

| Triglycerides | Baseline | Day 3 | %chg | Day 7 | %chg | Day 9 | %chg | Day 14 | %chg |
|---|---|---|---|---|---|---|---|---|---|
| 10 mg/m2 (n=2) | 0.3 ± 0.0 | 0.5 ± 0.3 | 57.1% | 0.6 ± 0.2 | 66.1% | 0.4 | 17.6% | - | - |
| 40 mg/m2 (n=9) | 1.0 ± 0.5 | 1.5 ± 0.7 | 55.8% | 2.0 ± 0.8 | 113.4% | 1.6 ± 0.6 | 82.2% | 1.2 ± 0.5 | 12.0% |
| Total (n=11) | 0.9 ± 0.5 | 1.3 ± 0.8 | 56.0% | 1.7 ± 1.0 | 103.9% | 1.5 ± 0.8 | 73.0% | 1.2 ± 0.5 | 12.0% |

| HDL | Baseline | Day 3 | %chg | Day 7 | %chg | Day 9 | %chg | Day 14 | %chg |
|---|---|---|---|---|---|---|---|---|---|
| 10 mg/m2 (n=2) | 1.3 ± 0.1 | 1.2 ± 0.2 | -6.3% | 1.2 ± 0.2 | -2.5% | 1.3 | -2.9% | - | - |
| 40 mg/m2 (n=9) | 1.1 ± 0.2 | 0.9 ± 0.2 | -16.2% | 0.8 ± 0.1 | -20.1% | 1.0 ± 0.1 | -5.6% | 1.1 ± 0.2 | 5.8% |
| Total (n=11) | 1.1 ± 0.2 | 1.0 ± 0.2 | -13.7% | 0.9 ± 0.2 | -16.6% | 1.0 ± 0.2 | -5.0% | 1.1 ± 0.2 | 5.8% |

| Cholesterol | Baseline | Day 3 | %chg | Day 7 | %chg | Day 9 | %chg | Day 14 | %chg |
|---|---|---|---|---|---|---|---|---|---|
| 10 mg/m2 (n=2) | 4.3 ± 0.2 | 4.3 ± 0.2 | -1.2% | 4.5 ± 0.3 | 3.4% | 4.5 | 2.8% | - | - |
| 40 mg/m2 (n=9) | 4.0 ± 0.7 | 3.8 ± 0.6 | -1.3% | 4.3 ± 0.6 | 11.6% | 4.5 ± 0.8 | 23.2% | 4.7 ± 0.6 | 18.1% |
| Total (n=11) | 4.1 ± 0.7 | 3.9 ± 0.6 | -1.3% | 4.3 ± 0.6 | 9.9% | 4.5 ± 0.7 | 20.3% | 4.7 ± 0.6 | 18.1% |

| LDL | Baseline | Day 3 | %chg | Day 7 | %chg | Day 9 | %chg | Day 14 | %chg |
|---|---|---|---|---|---|---|---|---|---|
| 10 mg/m2 (n=2) | 2.9 ± 0.1 | 2.8 ± 0.3 | -2.4% | 3.0 ± 0.3 | 2.2% | 2.9 | 4.6% | - | - |
| 40 mg/m2 (n=9) | 2.5 ± 0.7 | 2.3 ± 0.4 | -0.1% | 2.6 ± 0.7 | 10.3% | 3.0 ± 0.7 | 31.3% | 3.0 ± 0.6 | 26.0% |
| Total (n=11) | 2.6 ± 0.6 | 2.4 ± 0.5 | -0.6% | 2.7 ± 0.6 | 8.7% | 3.0 ± 0.6 | 26.0% | 3.0 ± 0.6 | 26.0% |

*FIG. 10*

THERAPEUTIC REGIMEN AND METHODS FOR TREATING OR AMELIORATING VISUAL DISORDERS ASSOCIATED WITH AN ENDOGENOUS RETINOID DEFICIENCY

CROSS-REFERENCE TO RELATED APPLICATIONS

This application claims the benefit of U.S. Provisional Patent Application No. 61/325,763, filed Apr. 19, 2010, U.S. Provisional Patent Application No. 61/407,436 filed Oct. 27, 2010, and U.S. Provisional Patent Application 61/447,611 filed Feb. 28, 2011, the disclosures of which are incorporated herein by reference for all purposes.

FIELD OF THE INVENTION

This invention is directed to therapeutic regimens and methods for treating visual disorders associated with an endogenous retinoid deficiency in a subject by administering a synthetic retinal derivative to the subject, wherein the therapeutic regimens and methods result in improvements in the subject's visual function.

BACKGROUND OF THE INVENTION

Retinal deficiencies disrupt or interfere with the production, conversion and/or regeneration of 11-cis-retinal, which is a key Vitamin A derivative in the retinoid or visual cycle. 11-Cis-retinal is an endogenous retinoid produced in and by the retinal pigment epithelium (RPE) from the isomerization and oxidation of the all-trans-retinol (Vitamin A derived from the diet). 11-Cis-retinal functions as a chromophore and covalently binds to the protein opsin to form rhodopsin. Vision is initiated when a light photon is captured by 11-cis-retinal, resulting in the isomerization to all-trans-retinal and disassociation from opsin. Vision is sustained by the cycling of all-trans-retinal back into 11-cis-retinal, which occurs by a complex series of biochemical reactions involving multiple enzymes and proteins in the retinoid or visual cycle.

Endogenous retinoid deficiencies, such as those caused by mutations in the genes encoding the enzymes and proteins utilized in the visual cycle or those caused by the aging process, impair the synthesis of 11-cis-retinal, the result of which leads to visual disorders due to the shortage or depletion of 11-cis-retinal.

For example, Leber congenital amaurosis (LCA), a cause of inherited childhood blindness that affects children from birth or shortly thereafter, is associated with an inherited gene mutation in the RPE65 gene which encodes the protein retinal pigment epithelial protein 65 (RPE65) and/or an inherited gene mutation in the LRAT gene which encodes the enzyme lecithin:retinol acetyltransferase (LRAT). RPE65 and LRAT are both critical for the visual cycle. Patients with LCA lack the ability to generate 11-cis-retinal in adequate quantities and therefore suffer from severe vision loss at birth, nystagmus, poor pupillary responses and severely diminished electroretinograms (ERGs).

Mutations in the LRAT or RPE65 genes are also associated with autosomal recessive retinitis pigmentosa (arRP), which is a subset of hereditary retinitis pigmentosa (RP) which is characterized by degeneration of rod and cone photoreceptors. Patients with arRP may lose vision either in childhood or in mid-life. The classic pattern of vision loss includes difficulties with dark adaptation and night blindness in adolescence and loss of mid-peripheral visual field in young adulthood. arRP typically presents itself as primary rod degeneration with secondary degeneration of cones and is thus described as a rod-cone dystrophy, with rods being more affected than cones. This sequence of the photoreceptor cells involvement explains why arRP patients initially exhibit night blindness, and only in later life become visually impaired in diurnal conditions (Hamel C., Orphanet Journal of Rare Diseases I:40 (2006)). arRP is the diagnosis given to patients with photoreceptor degeneration who have good central vision within the first decade of life, although arRP onset can also occur much later at either the beginning of mid-life or after mid-life ("late onset arRP"). As the disease progresses, patients lose far peripheral vision, eventually develop tunnel vision, and finally lose central vision by the age of 60 years.

Retinitis Punctata Albesciens is another form of Retinitis Pigmentosa that exhibits a shortage of 11-cis-retinal in the rods. Aging also leads to the decrease in night vision and loss of contrast sensitivity due to a shorting of 11-cis retinal. Excess unbound opsin is believed to randomly excite the visual transduction system. This can create noise in the system, and thus more light and more contrast is necessary to see well.

Congenital Stationary Night Blindness (CSNB) and Fundus Albipunctatus are a group of diseases that are manifested as night blindness, but there is not a progressive loss of vision as in the Retinitis Pigmentosa. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown recently that this is also a progressive disease although much slower than Retinitis Pigmentosa. It is caused by a gene defect that leads to a delay in the cycling of 11-cis-retinal.

Endogenous retinoid deficiencies can also be associated with the aging process, even in the absence of inherited gene mutations of the genes encoding the enzymes and proteins utilized in the visual cycle. Age-related visual disorders include, for example, loss of night vision, nyctalopia and contrast sensitivity due to a shortage of 11-cis-retinal. This is consistent with the finding that a dramatic slowing of rod-mediated dark adaptation after light exposure associated with human aging is related to a delayed regeneration of rhodopsin (Jackson, G. R. et al., J. Vision Research 39, 3975-3982 (1999)). In addition, excess unbound opsin (due to 11-cis-retinal shortage) is believed to randomly excite the visual transduction system. This can create noise in the system, and thus necessitates more light and/or more contrast in order to see well.

The use of synthetic retinal derivatives and compositions thereof in methods of restoring or stabilizing photoreceptor function in a vertebrate visual system and in methods of treating age-related retinal dysfunction is disclosed in International Published Patent Application Nos. WO 2004/082622, WO 2006/002097, and WO 2011/034551, and Published U.S. Application Nos. 2004/0242704 and 2010/0035986. A study to evaluate the effects of daily and intermittent dosing of 9-cis-retinyl acetate, a synthetic retinal derivative, in RPE65−/− mice is disclosed in Maeda, T. et al., Investigative Ophthalmology & Visual Science (2009), Vol. 50, No. 9, pp. 4368-4378).

Animal models have shown that synthetic retinoids which are highly-light sensitive compounds are photoisomerized or "bleached" by light from the retina within just a few hours unless the eyes are covered. These studies were conducted with the animals kept in the dark during and following treatment with synthetic retinoids until the evaluation period in order to minimize photoisomerization/bleaching of the synthetic retinoid. Batten M L et al. "Pharmacological and rAAV Gene Therapy Rescue of Visual Functions in a Blind Mouse Model of Leber Congenital Amaurosis" PLo-S Medicine vol. 2, p. 333 (2005); Margaron, P., Castaner, L., and Narfstrom, K. "Evaluation of Intravitreal cis-Retinoid Replacement Therapy in a Canine Model Of Leber's Congenital Amaurosis" Invest Ophthalmol Vis Sci 2009; 50:E-Abstract 6280; Gearhart P M, Gearhart C, Thompson D A, Petersen-Jones S M. "Improvement of visual performance with intravitreal administration of 9-cis-retinal in Rpe65-mutant dogs" Arch Ophthalmol 2010; 128(11): 1442-8.

Frequent administration of any retinoid to compensate for the bleaching effect implicates the well known toxicity of the retinoid class of the compounds. See, Teelmann, K "Retinoids: Toxicity and Teratogenicity to Date," Pharmac. Ther., Vol. 40, pp 29-43 (1989); Gerber, L E et al "Changes in Lipid Metabolism During Retinoid Administration" J. Amer. Acad. Derm., Vol. 6, pp 664-74 (1982); Allen L H "Estimating the Potential for Vit A Toxicity in Women and Young Children" J. Nutr., Vol. 132, pp. 2907-19 (2002); Silverman, A K "Hypervitaminosis A Syndrome: A Paradigm of Retinoid Side Effects", J. Am. Acad. Derm., Vol. 16, pp 1027-39 (1987); Zech L A et al. "Changes in Plasma Cholesterol and Triglyceride Levels After Treatment with Oral Isotretinoin" Arch. Dermatol., Vol. 119, pp 987-93 (1983). Toxicity caused by chronic administration of retinoids can cause changes in lipid metabolism, damage to the liver, nausea, vomiting, blurred vision, damage to bones, interference with bone development and several other serious undesirable effects.

In the context of treating the loss or impairment of vision due to retinoid deficiency, which is a chronic condition requiring lifetime treatments, these toxic effects can be very important. These side effects are of particular concern in young patients, whose susceptibility to side effects related to their physical development is well documented.

This combination of a need for repeated administration in response to bleaching, and the undesirable serious side effects of repeated administration, poses a problem for the use of synthetic retinoids to treat the loss of vision caused by retinoid deficiency. A recent study evaluated the usefulness of retinoids as a treatment for these disorders and concluded that retinoids and similar compounds are simply not good clinical candidates for the treatment of retinoid deficiency disorders. See, Fan J. et al. "Light Prevents Exogenous 11-cis Retinal from Maintaining Cone Photoreceptors in Chromophore-deficient Mice", Invest. Ophthalmol. Vis Sci. Jan. 12, 2011, 10-6437.

It has now been discovered that by use of certain dosing regimens of synthetic retinal derivatives, it is possible to produce meaningful improvement or recovery of vision that is long lasting, while chronic toxic effects can be greatly reduced or even eliminated. This was completely unexpected, and indeed is completely contrary to the expectation of the art.

SUMMARY OF THE INVENTION

The present invention is directed to therapeutic regimens and methods for treating or ameliorating visual disorders associated with an endogenous retinoid deficiency in a subject, wherein the method and therapeutic regimen comprises the following sequential steps:

a) Administering to the subject a first dose of a first therapeutically effective amount of a synthetic retinal derivative or a first therapeutic effective amount of a pharmaceutically acceptable composition comprising a synthetic retinal derivative that provides for replacement of endogenously produced 11-cis-retinal;

b) commencing a resting period of at least one month during which a synthetic retinal derivative is not administered to the subject;

c) administering to the subject a second therapeutically effective amount of the synthetic retinal derivative;

d) repeating steps a through c as needed.

The therapeutic regimen described above is characterized in that the subject's visual function is meaningfully improved. This improvement is of a duration that is clinically useful and is not associated with toxic effects that would prevent or limit its long term use.

This invention is also directed to kits comprising a therapeutic effective amount of a synthetic retinal derivative or a therapeutic effective amount of a pharmaceutically acceptable composition comprising a synthetic retinal derivative and instructions for administering the synthetic retinal derivative or the pharmaceutically acceptable composition to a subject according to the therapeutic regimen disclosed herein. Preferably, the kits are for use in the treatment or amelioration of a visual disorder associated with endogenous retinoid deficiency in a subject.

The therapeutic regimens and methods of the invention maximize the efficacy of synthetic retinal derivatives or pharmaceutically acceptable compositions comprising synthetic retinal derivatives when administered to a subject while minimizing and/or managing the toxicity typically associated with retinoic acid derivatives.

Specific embodiments of these aspects of the invention are described in more detail below.

BRIEF DESCRIPTION OF THE DRAWINGS

FIG. 3. Eight Goldmann visual fields (GVFs) for subject #3 (A-H). At screening a non-detectable visual field was found using the V4e target (3A), which improved to a small central island on day 3 (3B). This central island was reliably detected through one month post dosing (3E).

FIG. 6. Demographics and baseline visual acuities (VA) for eleven subjects with either Leber Congenital Amaurosis (LCA) or Retinitis Pigmentosa (RP) due to mutations in either LRAT or RPE65 genes as listed. Best VA change from baseline for each eye is reported with the associated assessment date after treatment.

FIG. 10. Average levels of Triglycerides, HDL, Cholesterol and LDL were assessed through the 7 days of dosing with 10 mg/m2 or 40 mg/m2 of the composition of Example 1, and the following 7 days after treatment was complete. Elevations in triglyceride levels were observed, which were transient and returning to baseline after treatment was completed. A transient decrease in HDL levels was also observed. Effects on lipid metabolism were more pronounced in the 40 mg/m2 treatment group.

DETAILED DESCRIPTION OF THE INVENTION

Figure 1:
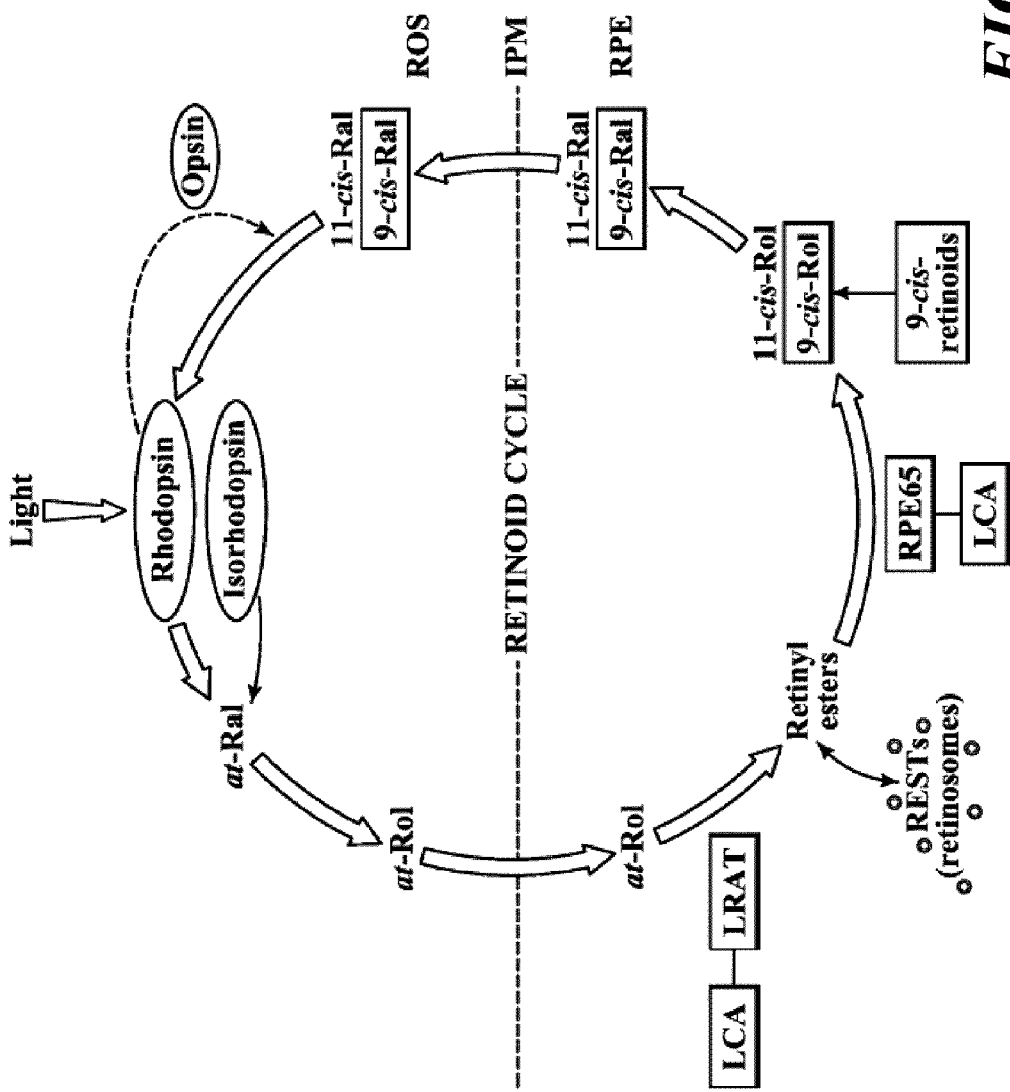
FIG. 1. Schematic drawing of the retinoid cycle.

In one aspect, the present invention is directed to therapeutic regimens for treating or ameliorating visual disorders in a subject, particularly loss of visual functions, by the administration of a synthetic retinal derivative or a pharmaceutically acceptable composition comprising the synthetic retinal derivative, which comprise first establishing a baseline of the subject's visual functions prior to administration, then administering a therapeutically effective amount of the synthetic retinal derivative or the pharmaceutically acceptable composition thereof to the subject for an initial dosing period, during which the subject's visual function improves as compared to the subject's baseline of visual function prior to administration, followed by a resting period during which no synthetic retinal derivative or pharmaceutically acceptable composition thereof is administered and the subject's visual functions continue to improve or the improvements in the subject's visual functions obtained during the first dosing period are sustained, followed by a subsequent administration of the synthetic retinal derivative or a pharmaceutically acceptable composition thereof after the resting period. The resting period and subsequent administration of the synthetic retinal derivative or the pharmaceutically acceptable composition can be repeated as needed to maintain the improvement in the subject's visual function achieved during the first dosing period or during the resting period. Optionally, a determination may be made during the initial resting period as to whether a subsequent therapeutic effective amount of the synthetic retinal derivative or the pharmaceutically acceptable composition thereof is to be administered based on the subject's visual function evaluated during the resting period.

In one embodiment, the baseline of the subject's visual function is established prior to the administration of the first therapeutic effective dose of the synthetic retinal derivative or a pharmaceutically acceptable composition thereof by evaluating one or more of the subject's visual field, visual acuity, ability to perform life tasks, retinal sensitivity, dynamic pupillary response, nystagmus, cortical visual function, color vision or dark adaptation. In a further embodiment, the baseline of the subject's visual function is established by evaluating the subject's field of vision. In another embodiment, the baseline of the subject's visual function is established by evaluating the subject's visual acuity. In another embodiment, the baseline is established by evaluating the subject's retinal sensitivity. In another embodiment, the baseline is established by evaluating the subject's visual field, visual acuity and retinal sensitivity.

In another embodiment, establishing the subject's baseline of visual function comprises establishing a baseline of the subject's visual field, the subject's visual acuity, the subject's retinal sensitivity, the subject's dynamic pupillary response, the subject's nystagmus, the subject's cortical visual function, the subject's ability to perform life tasks, the subject's color vision and/or the subject's dark adaptation. Preferably, establishing the subject's baseline of visual function comprises establishing the baseline of the subject's visual field, the subject's visual acuity, the subject's ability to perform life tasks, and the subject's retinal sensitivity by established tests.

In one embodiment, the subject's visual function rapidly improves during the first dosing period from the baseline of the subject's visual function established prior to administration of the first therapeutic effective amount of the synthetic retinal derivative or the pharmaceutically acceptable composition thereof to the subject. For purposes of this invention, "rapidly" improves refers to a clinically meaningful improvement in a subject's visual functions as compared to the baseline of the subject's visual functions in a period shorter than the first dosing period. Preferably, in one embodiment, the subject's visual functions are significantly improved within three days, within two days, or within one day of the commencement of the first dosing period. In another embodiment, the subject's visual functions improve during the first dosing period as compared to baseline, and continue to improve after the completion of the first dosing period and into the first rest interval. In a further embodiment, the improvement in the subject's visual function in the first dosing period comprises expanding the subject's visual field as compared to the visual field baseline, improving the subject's visual acuity as compared to the visual acuity baseline, and/or improving the subject's retinal sensitivity as compared to the baseline retinal sensitivity.

In one embodiment, the improvement in the subject's visual function during the first dosing period comprises an expansion of the subject's visual field as compared to the baseline.

In another embodiment, the improvement in the subject's visual function in the initial resting period comprises an expansion of the subject's visual field as compared to the expansion of the subject's visual field during the first dosing period.

In another embodiment, the improvement in the subject's visual function during the first dosing period and/or the resting period comprises an expansion of the subject's visual field temporally and/or nasally. In one embodiment of the invention, the expansion of the subject's visual field during the first dosing period is by at least 5 degrees or at least 10 degrees nasally, and at least 20 degrees, or at least 30 degrees or at least 40 degrees temporally.

In another embodiment, the improvement in the subject's visual function in the first dosing period comprises an improvement in the subject's visual acuity as compared to the baseline.

In another embodiment, the improvement in the subject's visual function in the resting period comprises an improvement in the subject's visual acuity as compared to the improvement in the subject's visual acuity during the first dosing period.

In another embodiment, the improvement in the subject's visual function in the first dosing period comprises an improvement in the subject's retinal sensitivity as compared to the baseline.

In another embodiment, the improvement in the subject's visual function in the resting period comprises an improvement in the subject's retinal sensitivity as compared to the improvement in the subject's retinal sensitivity during the first dosing period.

In another embodiment, the improvement in the subject's visual function in the resting period comprises an improvement in the subject's ability to perform life tasks, as compared to the improvement in the subject's retinal sensitivity during the first dosing period. In one embodiment, the resting period can be of any length of time from about one month or longer. In other embodiments of the invention, the resting period is from about 1 month to about 1 year. The length of the resting period will be dependent upon the therapeutic effective amount of synthetic retinal derivative or the therapeutic effective amount of a pharmaceutically acceptable composition comprising a retinal derivative to be administered therein. The first resting period can be for about 1 to 3 months. In one embodiment of this invention, the resting period is from one month to nine months in duration. In other embodiments, the resting period is from one to six months, or from three to six months.

In other embodiments of the invention, the resting period is not a fixed period. Instead, good clinical judgment may indicate that it is preferable to wait until the visual improvement that the treatment has produced in the subject has begun to reverse or has reversed to a significant degree before administering another dose of synthetic retinoid derivative. When later doses are administered in this way, the clinician will evaluate the subject's vision as needed and, in the exercise of good clinical judgment in light of the subject's overall health and vision, will determine when an additional dose of synthetic retinoid derivative is warranted. In any event, the additional doses of synthetic retinoid derivative will not be administered at intervals short enough to cause chronic retinoid toxicity.

In another embodiment, there is provided a method for the prophylaxis or treatment of a subject having or at risk for developing a diminished visual capacity. The method generally includes determining whether the subject has a deficient endogenous retinoid level or is at risk for development thereof, as compared with a standard subject, and administering an effective amount of a synthetic retinal derivative or a pharmaceutical composition thereof.

A therapeutically effective amount of the synthetic retinoid derivative is typically in the range of from about 49 milligrams per square meter of body surface area (mg/m$^2$) to about 840 mg/m$^2$. This amount can be administered in a single dose, or as a divided dose over a period as long as two weeks. The size of the dose, and the time over which the divided dose is administered, will be determined in the exercise of routine good clinical judgment in light of the subject's overall health, the degree of vision loss or impairment, age, and other factors.

In some embodiments, the therapeutically effective amount of the synthetic retinal derivative is in the range of from about 70 to 525 mg/m$^2$. In other embodiments, the therapeutically effective amount of the synthetic retinoid derivative is in the range of from about 70 to 490 mg/m$^2$. In other embodiments, the therapeutically effective amount of the synthetic retinoid derivative is in the range of from about 70 to 420 mg/m$^2$. Yet in other embodiments, the therapeutically effective amount of the synthetic retinoid derivative is in the range of from about 49 to 280 mg/m$^2$. In some embodiments, the therapeutically effective amount of the synthetic retinoid derivative is in the range of from about 280 to 490 mg/m$^2$. In yet other embodiments, the therapeutically effective amount of the synthetic retinoid derivative is in the range of from about 70 to 280 mg/m$^2$.

The above therapeutically effective amount can also be administered in a divided dose, for example over five days to fourteen days. In some embodiments, the above therapeutically effective amount can be administered in a divided dose over seven to ten days. The divided dose is typically administered in equal daily amounts over the dosing period.

The therapeutically effective amount can be adjusted during the course of treatment. In some embodiments, the amount of later doses is reduced from the amount of the initial dose. In other embodiments, the amount of the later doses is the same as the amount of the initial dose, while in other embodiments, the amount of the later dose may be increased from the amount of the initial dose. The size of the later doses, and the time over which the divided dose is administered, will be determined in the exercise of routine good clinical judgment in light of the subject's overall health, the degree of vision loss or impairment, the degree of improvement in the subject's visual function, age, and other factors.

In one embodiment, the subject's loss of vision is due to a LRAT or RPE65 gene mutation. In one preferred embodiment of the invention, the subject has a LRAT gene mutation. In another preferred embodiment of the invention, the subject has a RPE65 gene mutation. In another preferred embodiment of the invention, the subject has a LRAT gene mutation and a RPE65 gene mutation.

In one embodiment, the subject has Leber congenital amaurosis (LCA), autosomal recessive retinitis pigmentosa (arRP), age-related retinal dysfunction, nyctalopia, retinitis punctata albesciens, congenital stationary night blindness or fundus albipunctatus. In one preferred embodiment of the invention, the subject has LCA. In another preferred embodiment of the invention, the subject has arRP. In another preferred embodiment of the invention, the subject has age-related retinal dysfunction characterized by one or more of the following conditions: an impairment in rod-mediated dark adaptation after light exposure, an impairment in night vision, an impairment in contrast sensitivity, an impairment in visual field, an impairment in visual acuity and age-related macular degeneration (AMD).

In one embodiment, the subject is an adult.

In another embodiment, the subject is a pediatric patient, for example, an infant, a child or an adolescent.

In another embodiment, the patient is younger than 15 years old. Preferably, the subject has LCA and is younger than 15 years old.

In another embodiment, the subject is younger than 1 year. Preferably, the subject has LCA and is younger than 1 year old.

In another embodiment, the subject is 15 years old or older. Preferably, the subject has arRP and is at least 15 years old, preferably between 30 and 40 years old.

In another embodiment, the subject is 5 years old or older.

In one embodiment, the first and any subsequent therapeutic effective amount is administered orally to the subject.

In another embodiment, the first and any subsequent therapeutic effective amount is administered locally to the eyes of the subject.

In another embodiment, the first and any subsequent therapeutic effective amount is administered topically to the eyes of the subject.

In another embodiment the first and any subsequent therapeutic effective amount is administered intraocularly.

In another embodiment, the first and any subsequent therapeutic effective amount is administered subcutaneously.

The synthetic retinal derivative can be delivered by any pharmacologic vehicle in which it is stably delivered to the subject and effectively released upon administration. The pharmaceutical vehicle art is well familiar with the chemistry of retinoids and the formulations of pharmacologic vehicles for them. These known delivery vehicles include those which have physical properties, chemical properties and release rates that are suited to delivery synthetic retinal derivatives. Liquid delivery vehicles, such as vegetable oils (including soybean, olive, and rapeseed or canola oils) can be used.

In one embodiment, the synthetic retinal derivative is selected from 11-cis-retinyl acetate, 11-cis-retinyl succinate, 11-cis-retinyl citrate, 11-cis-retinyl ketoglutarate, 11-cis-retinyl fumarate, 11-cis-retinyl malate or 11-cis-retinyl oxaloacetate. Preferably the synthetic retinal derivation is 11-cis retinyl acetate.

Preferably, the 9-cis-retinyl ester is 9-cis-retinyl acetate or 9-cis-retinyl succinate.

Another embodiment of this aspect is wherein the pharmaceutically acceptable composition further comprises a lipid vehicle.

Another embodiment of this aspect is wherein the pharmaceutically acceptable composition comprises a 9-cis-retinyl ester and soybean oil.

Another embodiment of this aspect is wherein the 9-cis-retinyl ester is 9-cis-retinyl acetate.

Another embodiment of this aspect is wherein the subject has a LRAT or RPE65 mutation.

Another embodiment of this aspect is wherein the subject has Leber congenital amaurosis, retinitis pigmentosa, age-related retinal dysfunction, nyctalopia, retinitis punctata albesciens, congenital stationary night blindness or fundus albipunctatus.

Another embodiment is wherein the age-related retinal dysfunction is manifested by one or more of the following clinical conditions: an impairment in rod-mediated dark adaptation after light exposure, an impairment in night vision, an impairment in contrast sensitivity, an impairment in visual field, an impairment in visual acuity and age-related macular degeneration (AMD).

Another embodiment of this aspect is wherein the synthetic retinal derivative or the pharmaceutically acceptable composition comprising the synthetic retinal derivative is administered orally to the subject.

Another embodiment of this aspect is wherein the synthetic retinal derivative or the pharmaceutically acceptable composition comprising the synthetic retinal derivative is administered locally to the eyes of the subject.

Another embodiment of this aspect is wherein the synthetic retinal derivative or the pharmaceutically acceptable composition comprising the synthetic retinal derivative is administered topically to the eyes of the subject.

Another embodiment of this aspect is wherein the synthetic retinal derivative or the pharmaceutically acceptable composition comprising the synthetic retinal derivative is administered intraocularly.

Another embodiment of this aspect is wherein the synthetic retinal derivative or the pharmaceutically acceptable composition comprising the synthetic retinal derivative is administered subcutaneously.

In one embodiment of the invention, the therapeutic regimen of the invention is an administration regimen for treating a visual disorder associate with endogenous retinoid deficiency in a subject.

Another aspect of the invention is the use of a synthetic retinal derivative in the preparation of a medicament for administration to a subject having an endogenous retinoid deficiency. Preferably, the medicament is administered to the subject by a therapeutic regimen disclosed herein.

Another aspect of the invention is directed to kits comprising a therapeutic effective amount of a synthetic retinal derivative or a therapeutic effective amount of a pharmaceutically acceptable composition comprising a synthetic retinal derivative and instructions for using the synthetic retinal derivative or a therapeutic effective amount of a pharmaceutically acceptable composition comprising a synthetic retinal derivative in a therapeutic regimen or method of the invention for the treatment or amelioration of a visual disorder associated with endogenous retinoid deficiency in a subject.

These and other embodiments of the invention are disclosed in more detail herein.

Unless defined otherwise in the specification, the following terms and phrases shall have the following meanings:

As used herein, "visual disorders" refers broadly to disorders in the photoreceptors, tissue or structures of the eye. Visual disorders include, but are not limited to, retinal degeneration, retinal dystrophy, loss of photoreceptor function, photoreceptor cell death and structural abnormalities. For purposes of this invention, the phrase "visual disorders" refers to visual disorders associated with an endogenous retinoid deficiency. Visual disorders of the invention are typically characterized by impaired or less than normal (including complete loss of) visual functions in the subject, which include, for example, poor visual acuity, low or lack of retinal sensitivity, narrow or undetectable visual fields, and the like.

"Therapeutically effective amount" refers to that amount of a compound which, when administered to a subject, preferably a human, is sufficient to cause a clinically meaningful therapeutic effect.

The term "therapeutic effect" as used herein refers to the improvement or restoration of the vision of a patient, in one or both eyes of the patient.

The loss of vision in patients with retinoid deficiency is typically severe, but can be present in degree and forms that vary from patient to patient. Patients can lose their peripheral vision, they can lose their ability to see in low to moderate light, their overall acuity can decline, or other vision loss can occur. This loss can be progressive (especially in adult onset case(s) of retinoid deficiency, such as retinitis pigmentosa) eventually leading to very little vision or to complete blindness. When not progressive (such as in Congenital Stationary Night Blindness) loss of vision can be severe, if not nearly complete, from the outset.

The type and extent of loss can be roughly correlated to the degree of retinoid deficiency, affected cell type (e.g. rods or cones), and/or localization of the retinoid deficiency in the retina. Where the deficiency effect is strongest at the periphery of the retina, peripheral vision losses can be seen earliest and most profoundly. When the deficiency effect is more generalized throughout the retina, an overall loss of acuity is more commonly observed. When the deficiency is great or of long standing, the vision loss (in whatever form) can be more severe and more difficult to successfully treat. All of these variations in the nature, degree, and progression of vision loss in retinoid deficiency patients are well-known to clinicians.

Because the nature and degree of vision loss caused by the retinoid deficiency disorder varies from patient to patient, the nature and degree of meaningful improvement or recovery of vision will also vary from patient to patient. For example, regaining the ability to see in moderate light can be a meaningful improvement that is manifested in some patients. For other patients a meaningful improvement will be to achieve restored peripheral vision, or a general improvement in acuity. Ideally, progressive loss of vision can be arrested and reversed by this invention. However, in cases where diagnosis and treatment occur early, treatment according to this invention may simply limit or slow the progression of vision loss.

Clinically meaningful improvements can be documented by any of several known clinical measures discussed in this application, including acuity, field of vision, light sensitivity, the ability to perform life tasks or a combination of some or all of these. These measures and others are all well known to the clinicians and are routinely used in clinical practice. Clinicians are easily able to identify and observe these changes as part of routine clinical evaluations of retinoid deficiency patients. Consequently, clinicians are also easily able to observe the identify improvements in vision that are meaningful in the context of a given patient.

The term "subject" refers to a human patient. The term "patient" refers to a human having an endogenous retinal deficiency and/or a human who has been diagnosed as having an endogenous retinal deficiency.

Visual Disorders Associated with Endogenous Retinoid Deficiency

The therapeutic regimens and methods of the invention are for the treatment and amelioration of visual disorders associated with an endogenous retinoid deficiency in a subject, preferably loss of visual functions due to endogenous retinoid deficiencies. Such deficiencies are characterized by an absent, deficient or depleted level of one or more endogenous retinoids, such as 11-cis-retinal. Thus, "endogenous retinoid deficiency" refers to prolonged lower levels of endogenous retinoids as compared to the levels found in a healthy eye of a subject of the same species. While a healthy eye of a subject may experience transient shortage of 11-cis-retinal, which leads to a brief period of blindness followed by vision recovery, a subject with endogenous retinoid deficiency is deficient in its ability to reliably or rapidly regenerate the endogenous level of 11-cis-retinal, which leads to prolonged and/or pronounced 11-cis retinal deficits.

Endogenous retinoid deficiency can be caused by one or more defects in the visual cycle which includes enzymatic deficiencies and impaired transport processes between the photoreceptors and retinal pigment epithelial cells (RPE). FIG. 1 schematically shows a vertebrate, preferably the human, visual cycle (or retinoid cycle), which operates between the RPE and the outer segments of photoreceptors. 11-cis-retinal is regenerated through a series of enzymatic reactions and transport processes to and from the RPE after which it binds to opsin to form rhodopsin in the photoreceptor. Rhodopsin is then activated by light to form meta-rhodopsin which activates the phototransduction cascade while the bound cis-retinoid is isomerized to all-trans-retinal (von Lintig, J. et al., Trends Biochem Sci Feb. 24 (2010)).

Mutations in more than a dozen genes encoding retinal proteins have been identified that participate in several biochemical pathways in the visual cycle. For example, mutations in genes that encode lecithin:retinoid acetyl transferase (the LRAT gene) and retinal pigment epithelium protein 65 kDa (the RPE65 gene) disrupt the retinoid cycle, resulting in a deficiency of 11-cis-retinal, an excess of free opsin, an excess of retinoid waste (e.g., degradation) products and/or intermediates in the recycling of all-trans-retinal, or the like.

Endogenous retinoid levels in a subject's eyes and deficiencies of such levels may be determined in accordance with the methods disclosed in, for example, U.S. Published Patent Application No. 2005/0159662 (the disclosure of which is incorporated by reference herein in its entirety). Other methods of determining endogenous retinoid levels in a vertebrate eye and a deficiency of such retinoids include, for example, analysis by high pressure liquid chromatography (HPLC) of retinoids in a blood sample from a subject. For example, a blood sample can be obtained from a subject and retinoid types and levels in the sample can be separated and analyzed by normal phase high pressure liquid chromatography (HPLC) (e.g., with a HP 1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. A deficiency in retinoids can be determined, for example, by comparison of the profile of retinoids in the sample with a sample from a control subject (e.g., a normal subject).

Various conditions can cause a subject to be predisposed to or develop endogenous retinoid deficiency. For example, a subject that has an RPE65 gene mutation or an LRAT gene mutation is genetically predisposed to endogenous retinoid deficiency and visual impairment that ultimately lead to complete vision loss and severe retinal dystrophy. In particular, RPE65 and LRAT gene mutations are found in both LCA and arRP patients. Even in the absence of any genetic defects in the visual cycle, an aging subject may nonetheless develop endogenous retinoid deficiency.

Examples of visual disorders associated with endogenous retinoid deficiency are discussed in detail below.

A. Leber Congenital Amaurosis (LCA)

One condition associated with endogenous retinoid deficiency is Leber Congenital Amaurosis (LCA). LCA is an inherited childhood disease with early onset vision loss and retinal dystrophy. Mutations in the RPE65 gene in patients with autosomal recessive retinitis pigmentosa (arRP) or Leber congenital amaurosis have been reported to cause 0.5% and 6% of LCA cases, respectively (den Hollander, A. I. et al., Prog Ret Eye Res 27:391-419, (2008) and den Hollander, A. I. et al., Proc Natl Acad Sci USA 95:3088-93 (1998)). These forms are characterized by a significant deficiency of 11-cis-retinal, the visual chromophore that binds rod and cone opsins to form the visual pigments (rhodopsin and cone-pigments) (Redmond, T. M. et al., Nat Gen 20:344-51 (1998) and Batten, M. L. et al., J Biol Chem 279:10422-32 (2004)). Chronic deficiency of 11-cis-retinal eventually results in photoreceptor degeneration (Travis, G. H. et al., Annu Rev Pharmacol Toxicol 47:469-512 (2007)). The interval between the loss of visual function and retinal degeneration creates an opportunity for vision rescue.

In subjects having LCA due to an RPE65 gene mutation, retinyl esters build up in the retinal pigment epithelium (RPE) (Thompson, D. A. et al., Nat Gen 28:123-4 (2001) and Gu S. M. et al., Nat Gen 17:194-7 (1997)), which eventually results in retinal degeneration.

Subjects having LCA due to an LRAT gene mutation are unable to make esters and subsequently secrete any excess retinoids, which are associated with early-onset severe retinal dystrophy and retinal degeneration (Morimura H et al. Proc Natl Acad Sci USA 95:3088-93 (1998)).

B. Retinitis Pigmentosa and Night Blindness (Nyctalopia)

Another condition associated with endogenous retinoid deficiency is night blindness caused by, for example, retinitis pigmentosa (RP) or congenital stationary night blindness (CSNB).

RP is a condition caused by defects in many different genes. To date, 19 known and 17 uncharacterized gene mutations have been identified, causing great heterogeneity in the disease (Phelan, J. K. et al., Mol Vis. 6:116-124 (2000)). The age of onset for RP, as well as the severity of the disease, is a function of the mode of inheritance. RP may be inherited by autosomal dominant, autosomal recessive, or X-linked traits. Autsomal recessive RP (arRP) can occur in 20% of all RP cases. In recent years, mutations in the LRAT and RPE65 genes have been discovered in patients with arRP. These specific mutations are linked to defects in retinoid metabolism of the visual cycle and may result in photoreceptor degeneration (Morimura, H. et al., Proc Natl Acad Sci USA. 95(6):3088-3093 (1998)).

As noted herein, the protein encoded by the RPE65 gene has a biochemical association with retinol binding protein and 11-cis-retinol dehydrogenase and is essential for 11-cis-retinal production (Gollapalli, D. R. et al., Biochemistry. 42(19):5809-5818 (2003) and Redmond, T. M. et al., Nat Genet. 20(4):344-351 (1998)). Preclinical and clinical information show that loss of the function of the RPE65 protein blocks retinoid processing after esterification of vitamin A to membrane lipids and results in loss of vision.

Early stages of typical RP are characterized by night blindness and loss of mid-peripheral visual field, reflecting primary rod impairment. As the disease progresses, patients lose far peripheral and central vision, eventually leading to blindness. Prominent clinical findings include bone spicule-shaped pigment in the retina and attenuated/abnormal electroretinogram (ERG) responses. It is speculated that the absence of RPE65 products would cause a massive, early degeneration of photoreceptors while substitution of amino acids would lead to a slower pace of degeneration (Marlhens, F. et al., Eur J Hum Genet. 6(5):527-531 (1998)).

CSNB and fundus albipunctatus are a group of diseases that are manifested as night blindness, but there is not a progressive loss of vision as in the RP. Some forms of CSNB are due to a delay in the recycling of 11-cis-retinal. Until recently, fundus albipunctatus was thought to be a special case of CSNB where the retinal appearance is abnormal with hundreds of small white dots appearing in the retina. It has been recently been shown that fundus albipunctatus is also a progressive disease, although much slower than RP. Fundus albipunctatus is caused by a gene defect that leads to a delay in the cycling of 11-cis-retinal.

C. Age-Related Visual Disorders

Another condition associated with endogenous retinoid deficiency is age-related decrease in retinal photoreceptor function. As discussed herein, it has been recognized that inadequate availability and/or processing of vitamin A to the visual chromophore, 11-cis-retinal, can adversely affect vertebrate rhodopsin regeneration and visual transduction (McBee, J. K. et al., Prog Retin Eye Res 20, 469-529 (2001); Lamb, T. D. et al., Prog Retin Eye Res 23, 307-380 (2004); and Travis, G. H. et al., Annu Rev Pharmacol Toxicol (2006)). In aging, rhodopsin regeneration after light exposure is more delayed in humans and mice deprived of vitamin A due to either dietary deficiency or inadequate intestinal absorption (Lamb, T. D. et al., J. Prog Retin Eye Res 23, 307-380 (2004)). Moreover, treatment with vitamin A and its derivatives may have beneficial effects in aging and retinal diseases such as Sorbsby's fundus dystrophy and retinitis pigmentosa (Jacobson, S. G., et al., Nat Genet 11, 27-32 (1995); and Berson, E. L., et al., Arch Ophthalmol 111, 761-772 (1993)).

Age-related visual disorders include a slowing of rod-mediated dark adaptation after light exposure, a decrease in night vision (nyctalopia), and/or a decrease in contrast sensitivity. Age-related visual disorders may also include wet or dry forms of age-related macular degeneration (AMD).

AMD is one of the specific visual disorders associated with the posterior portion of the eyeball and is the leading cause of blindness among older people. AMD results in damage to the macula, a small circular area in the center of the retina. Because the macula is the area which enables one to discern small details and to read or drive, its deterioration may bring about diminished visual acuity and even blindness. People with AMD suffer deterioration of central vision but usually retain peripheral sight. In AMD, vision loss occurs when complications late in the disease either cause new blood vessels to grow under the retina or the retina atrophies.

D. Subject Populations

While any subject having a visual disorder associated with an endogenous retinoid deficiency (as defined herein) may be treated by the therapeutic regimens and methods of the invention, there is a physiological window of opportunity wherein the therapeutic regimen or method is the most effective in restoring visual function to the subject. Preferably, the window of opportunity for the therapeutic regimens of the invention to be the most effective in a subject is defined as the interval between loss of visual function and retinal degeneration, particularly with respect to photoreceptor cell degeneration. Subjects in certain age groups may particularly benefit from the therapeutic regimens of the invention. More specifically, subjects with a lesser degree of retinal/photoreceptor degeneration tend to have a better or faster response to the therapeutic regimen of the invention and/or may have a longer resting period before a subsequent dosing period is needed.

For example, in certain embodiments, younger subjects with a lost of visual function due to LCA or RP may retain a higher percentage of dormant photoreceptors. Such dormant photoreceptors are capable of responding to the therapeutic regimens of the invention. In particular, in treating lost of visual function in a subject arising from inherited childhood blindness such as LCA or early onset RP, such as arRP, younger subjects may expect a greater recovery of visual functions because their retinal degeneration is less advanced. Thus, in one embodiment of the invention, the subject is a human juvenile, i.e., younger than 15 years, old upon commencement of the therapeutic regimen. In other embodiments of the invention, the subject is a human newborn or a human infant younger than 1 year old, younger than 18 months, younger than 24 months or younger than 36 months old when the therapeutic regimen is commenced. In other embodiments, the subject is a human of 5 years old or older when the therapeutic regimen is commenced. In further embodiments, the human subject is 10 years old or older when the therapeutic regimen is commenced.

In some instances, RP may appear in a human subject during the second decade or even later. The average age of diagnosis for arRP in a human is about 36 years old (Tsujikawa M. et al., Arch Ophthalmol 126(3) 337-340 (2008)). Thus, in other embodiments, the human subject is 15 years old or older when the therapeutic regimen is commenced. In more specific embodiments, the human subject is 20 years old or older, 30 years old or older, 40 years or older, 50 years or older, 60 years or older or 70 years or older when the therapeutic regimen is commenced.

In further embodiments, the human subject is an aging subject suffering from age-related retinal disorders. As used herein, an aging human subject is typically at least 45, or at least 50, or at least 60, or at least 65 years old when the therapeutic regimen is commenced.

Preferably, for any of these subjects, the therapeutic regimens and methods of the invention should commence as soon as a diagnosis of a visual disorder as defined herein is ascertained, such that any degeneration of the retina, in particular the photoreceptors, has not reached a point where the therapeutic regimens of the invention would be ineffective in treating or ameliorating the visual disorder in the subject.

Synthetic Retinal Derivatives of the Invention

The present invention provides methods of restoring or stabilizing photoreceptor function in a subject's visual system. Synthetic retinal derivatives can be administered to restore or stabilize photoreceptor function, and/or to ameliorate the effects of a deficiency in retinoid levels. Photoreceptor function can be restored or stabilized, for example, by providing a synthetic retinoid that can act as an 11-cis-retinoid replacement and/or an opsin agonist. The synthetic retinoid also can ameliorate the effects of a retinoid deficiency on a subject's visual system. A synthetic retinoid can be administered prophylactically or therapeutically to a subject.

The synthetic retinal derivatives are retinoids derived from 11-cis-retinal or 9-cis-retinal. In certain embodiments, the synthetic retinal derivative is a synthetic 9- or 11-cis retinoid. In other embodiments, the synthetic retinoid is a derivative of 11-cis-retinal or 9-cis-retinal, with the proviso that the synthetic retinoid is not 9-cis-retinal. In some embodiments, a synthetic retinal derivative can, for example, be a retinoid replacement, supplementing the levels of endogenous retinoid.

Without intending to be bound by any particular theory, the synthetic retinal derivatives used in the therapeutic regimens of the invention provide replacements for endogenously produced 11-cis-retinal, thereby restoring the key biochemical component of the visual cycle. A synthetic retinal derivative suitable for the therapeutic regimens of the invention can be a derivative of 9-cis-retinal or 11-cis-retinal. Like 11-cis-retinal, 9-cis-retinal can bind to opsin to form photoactive isorhodopsin which, when bleached, undergoes conformational changes via the same photoproducts as 11-cis-retinal regenerated rhodopsin (Yoshizawa, T. et al., Nature 214, 566-571 (1967) and Filipek S. et al., Annu Rev Physiol 65:851-79 (2003)). 9-cis-retinal and its derivatives are generally more thermodynamically stable than their 11-cis retinal counterparts.

The synthetic retinal derivative can be converted directly or indirectly into a retinal or a synthetic retinal analog. Thus, in some aspects, the compounds according to the present invention can be described as pro-drugs, which upon metabolic transformation are converted into 9-cis-retinal, 11-cis-retinal or a synthetic retinal analog thereof. Metabolic transformation can occur, for example, by acid hydrolysis, esterase activity, acetyltransferase activity, dehydrogenase activity, or the like. For example, without wishing to be bound by theory, it is thought that a synthetic 9-cis-retinal derivative (e.g., 9-cis-retinyl acetate), is converted to 9-cis-retinol in the alimentary pathway, transported to the retina through the bloodstream and converted to 9-cis-retinal in the RPE.

Synthetic retinal derivatives suitable for the methods of the present disclosure can be those described in International Published Patent Application Nos. WO 2004/082622 and WO 2006/002097, and Published U.S. Application Nos. 2004/0242704 and US 2010/0035986, which applications are incorporated herein by reference in their entireties.

The synthetic retinal derivative can bind to opsin and function as an opsin agonist. As used herein, the term "agonist" refers to a synthetic retinal derivative that binds to opsin and facilitates the ability of the opsin/synthetic retinal derivative complex to respond to light. As an opsin agonist, a synthetic retinal derivative can create a pharmacological bypass of a blocked retinoid cycle, thus sparing the requirement for endogenous retinoid (e.g., 11-cis-retinal).

Synthetic retinal derivative include 11-cis-retinal derivatives or 9-cis-retinal derivatives such as, for example, the following: acyclic retinals; retinals with modified polyene chain length, such as trienoic or tetraenoic retinals; retinals with substituted polyene chains, such as alkyl, halogen or heteroatom-substituted polyene chains; retinals with modified polyene chains, such as trans- or cis-locked polyene chains, or with, for example, allene, alkane, alkene or alkyne modifications; and retinals with ring modifications, such as heterocyclic, heteroaromatic or substituted cycloalkane or cycloalkene rings.

In certain embodiments, the synthetic retinal derivative can be a retinal of the following formula I:

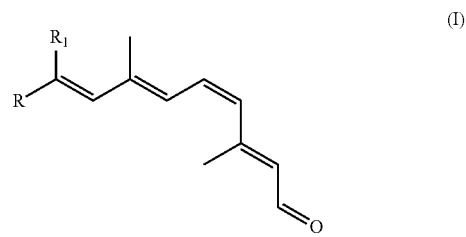

(I)

R and R1 can be independently selected from linear, iso-, sec-, tert- and other branched alkyl groups as well as substituted alkyl groups, substituted branched alkyl, hydroxyl, hydroalkyl, amine, amide, or the like. R and R1 can independently be lower alkyl, which means straight or branched alkyl with 1-6 carbon atom(s) such as methyl, ethyl, propyl, isopropyl, butyl, isobutyl, tert-butyl, pentyl, hexyl, or the like. Suitable substituted alkyls and substituted branch alkyls include, for example, alkyls, branched alkyls and cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

In certain additional embodiments, R or R1 can be a cyclo-alkyl such as, for example, hexane, cyclohexene, benzene as well as substituted cyclo-alkyl. Suitable substituted cyclo alkyl include, for example, cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

The synthetic retinal derivative also can be a derivative of an 11-cis-retinal or 9-cis-retinal that has a modified polyene chain length of the following formula II:

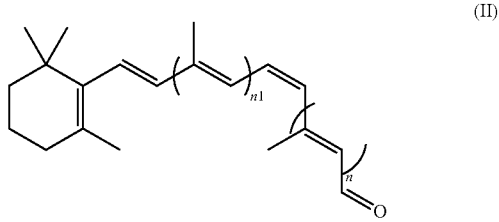

(II)

The polyene chain length can be extended by 1, 2, or 3 alkyl, alkene or alkylene groups. According to formula II, each n and n1 can be independently selected from 1, 2, or 3 alkyl, alkene or alkylene groups, with the proviso that the sum of the n and n1 is at least 1.

The synthetic retinal derivative also can be a derivative of an 11-cis-retinal or 9-cis-retinal that has a substituted polyene chain of the following formula III:

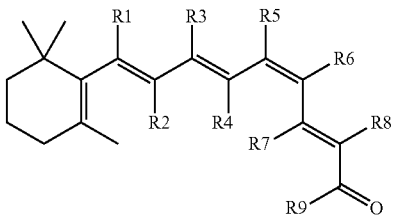
(III)

Each of $R_1$ to $R_9$ can be independently selected from hydrogen, alkyl, branched alkyl, cyclo-alkyl, halogen, a heteratom, or the like. Suitable alkyls include, for example, methyl, ethyl, propyl, substituted alkyl (e.g., alkane with hydroxyl, hydroalkyl, amine, amide) or the like. Suitable branched alkyl can be, for example, isopropyl, isobutyl, substituted branched alkyl, or the like. Suitable cyclo-alkyls can include, for example, cyclohexane, cycloheptane, and other cyclic alkanes as well as substituted cyclic alkanes such as substituted cyclohexane or substituted cycloheptane. Suitable halogens include, for example, bromine, chlorine, fluorine, or the like. Suitable heteroatoms include, for example, sulfur, silicon, and fluoro- or bromo-substitutions. Suitable substituted alkyls, substituted branch alkyls and substituted cyclo-alkyls include, for example, alkyls, branched alkyls and cyclo-alkyls substituted with oxygen, hydroxyl, nitrogen, amide, amine, halogen, a heteroatom or other groups. In exemplary embodiments, the synthetic retinoid is 9-ethyl-11-cis-retinal, 7-methyl-11-cis-retinal, 13-desmethyl-11-cis-retinal, 11-cis-10-F-retinal, 11-cis-10-Cl-retinal, 11-cis-10-methyl-retinal, 11-cis-10-ethyl-retinal, 9-cis-10-F-retinal, 9-cis-10-Cl-retinal, 9-cis-10-methyl-retinal, 9-cis-10-ethyl-retinal, 11-cis-12-F-retinal, 11-cis-12-Cl-retinal, 11-cis-12-methyl-retinal, 11-cis-10-ethyl-retinal, 9-cis-12-F-retinal, 9-cis-12-Cl-retinal, 9-cis-12-methyl-retinal, 11-cis-14-F-retinal, 11-cis-14-methyl-retinal, 11-cis-14-ethyl-retinal, 9-cis-14-F-retinal, 9-cis-14-methyl-retinal, 9-cis-14-ethyl-retinal, or the like.

The synthetic retinal derivaitve further can be derivative of an 11-cis-retinal or 9-cis-retinal that has a modified ring structure. Suitable examples include, for example, derivatives containing ring modifications, aromatic analogs and heteroaromatic analogs of the following formulae IV, V and VI, respectively:

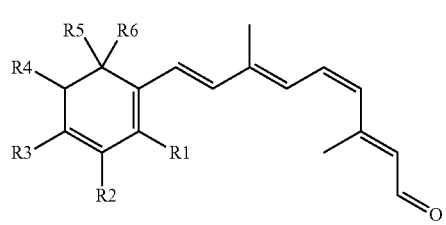
(IV)

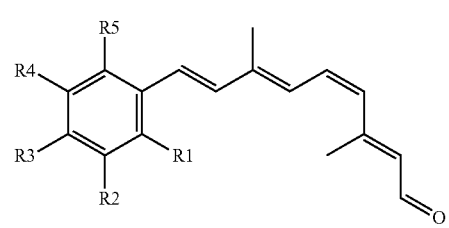
(V)

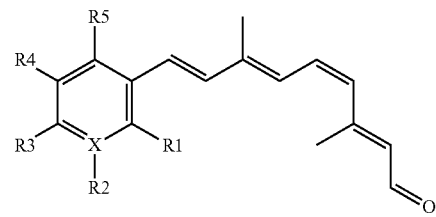
(VI)

Each of R1 to R5 or R6, as applicable, can be independently selected from hydrogen, alkyl, substituted alkyl, hydroxyl, hydroalkyl, amine, amide, halogen, a heteratom, or the like. Suitable alkyls include, for example, methyl, ethyl, propyl, isopropyl, butyl, isobutyl or the like. Suitable halogens include, for example, bromine, chlorine, fluorine, or the like. Suitable heteroatoms include, for example, sulfur, silicon, or nitrogen. In addition, X can be a heteroatoms, such as, for example, sulfur, silicon, or nitrogen.

The synthetic retinal derivative can further be a derivative of an 11-cis-retinal or 9-cis-retinal that has a modified polyene chain. Suitable derivatives include, for example, those with a trans/cis locked configuration, 6s-locked analogs, as well as modified allene, alkene, alkyne or alkylene groups in the polyene chain. In one example, the derivative is an 11-cis-locked analog of the following formula VII:

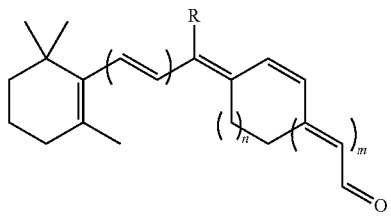
(VII)

R can be, for example, hydrogen, methyl or other lower alkane or branched alkane. n can be 0 to 4. m plus 1 equals 1, 2 or 3.

In a specific embodiment, the synthetic retinal derivative is a 11-cis-locked analog of the following formula VIII:

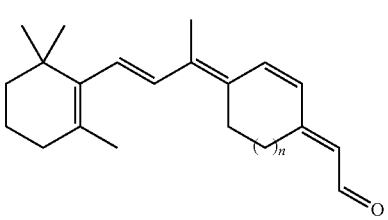
(VIII)

n can be 1 to 4.

In certain exemplary embodiments, the synthetic retinoid is 9,11,13-tri-cis-7-ring retinal, 11,13-di-cis-7-ring retinal, 11-cis-7-ring retinal or 9,11-di-cis-7-ring retinal.

In another example, the synthetic retinal derivative is a 6s-locked analog of formula IX. R1 and R2 can be independently selected from hydrogen, methyl and other lower alkyl and substituted lower alkyl. R3 can be independently selected from an alkene group at either of the indicated positions.

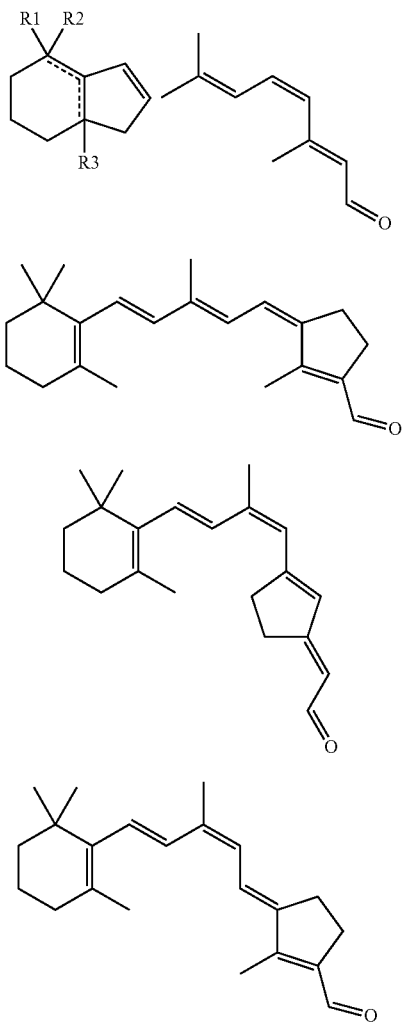

(IX)

(X)

(XI)

(XII)

In other embodiments, the synthetic retinoid can be a 9-cis-ring-fused derivative, such as, for example, those shown in formulae X-XII.

In yet another embodiment, the synthetic retinoid is of the following formula XIII.

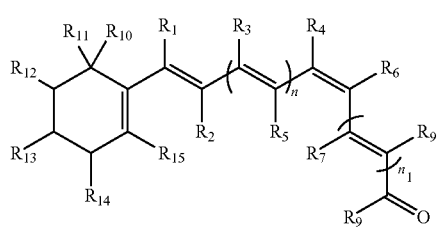

(XIII)

Each of $R_1$ to $R_{15}$ can be independently selected from hydrogen, alkyl, branched alkyl, halogen, hydroxyl, hydroalkyl, amine, amide, a heteratom, or the like. Suitable alkyls include, for example, methyl, ethyl, propyl, substituted alkyl (e.g., alkyl with hydroxyl, hydroalkyl, amine, amide), or the like. Suitable branched alkyl can be, for example, isopropyl, isobutyl, substituted branched alkyl, or the like. Suitable halogens include, for example, bromine, chlorine, fluorine, or the like. Suitable heteroatoms include, for example, sulfur, silicon, and fluoro- or bromo-substitutions. Suitable substituted alkyls and substituted branch alkyls include, for example, alkyls and branched alkyls substituted with oxygen, hydroxyl, nitrogen, amide, amine, halogen, heteroatom or other groups. Each of n and $n_1$ can be independently selected from 1, 2, or 3 alkyl, alkene or alkylene groups, with the proviso that the sum of the n and $n_1$ is at least 1. In addition, $R_{11}$-$R_{12}$ and/or $R_{13}$-$R_{14}$ can comprise an alkene group in the cyclic carbon ring. In certain embodiments, $R_5$ and $R_7$ together can form a cyclo-alkyl, such as a five, six, seven or eight member cyclo-alkyl or substituted cyclo-alkyl, such as, for example, those shown in formulae VII, VIII, X, XI and XII.

In additional embodiments, the synthetic retinal derivative also can be 9-cis-retinal. Alternatively, 11-cis-retinal can be used.

In additional embodiments, the synthetic retinal derivatives are derivatives of 9-cis-retinal or 11-cis-retinal in which the aldehydic group in the polyene chain is converted to an ester, ether, alcohol, hemi-acetal, acetal or oxime. Such synthetic retinal derivatives include 9-cis-retinyl esters, 9-cis-retinyl ethers, 9-cis-retinol, 9-cis-retinal oximes, 9-cis-retinyl acetals, 9-cis-retinyl hemiacetals, 11-cis-retinyl esters, 11-cis-retinyl ethers, 11-cis-retinol, 11-cis-retinyl oximes, 11-cis-retinyl acetals and 11-cis-retinyl hemiacetals, as further described herein.

In one aspect, the synthetic retinal derivative is a retinyl ester. In some embodiments, the retinyl ester is a 9-cis-retinyl ester or an 11-cis-retinyl ester. The ester substituent can be, for example, a carboxylic acid, such as a mono- or polycarboxylic acid. As used herein, a "polycarboxylic acid" is a di-, tri- or higher order carboxylic acid. In some embodiments, the carboxylic acid is a C1-C22, C2-C22, C3-C22, C1-C10, C2-C10, C3-C10, C4-C10, C4-C8, C4-C6 or C4 monocarboxylic acid, or polycarboxylic acid.

Suitable carboxylic acid groups include, for example, acetic acid, propionic acid, butyric acid, valeric acid, caproic acid, caprylic acid, pelargonic acid, capric acid, lauric acid, oleic acid, stearic acid, palmitic acid, myristic acid or linoleic acid. The carboxylic acid also can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

In an exemplary embodiment, the retinyl ester is a 9-cis-retinyl ester or an 11-cis-retinyl ester including a C3-C10 polycarboxylic acid substituent. (In this context, the terms "substituent" or "group" refer to a radical covalently linked to the terminal oxygen in the polyene chain.). In another exemplary embodiment, the retinyl ester is a 9-cis-retinyl ester or an 11-cis-retinyl ester including a C2-C22 or C3-C22 polycarboxylic acid substituent. The polycarboxylic acid substituent can be, for example, succinate, citrate, ketoglutarate, fumarate, malate or oxaloacetate. In another exemplary embodiment, the retinyl ester is a 9-cis-retinyl ester or an 11-cis-retinyl ester including a C3-C22 di-carboxylic acid (di-acid) substituent. In some embodiments, the polycarboxylic acid is not 9-cis-retinyl tartarate or 11-cis-retinyl tartarate. In some embodiments, the retinyl ester is not a naturally occurring retinyl ester normally found in the eye. In some embodiments, the retinyl ester is an isolated retinyl ester. As used herein, "isolated" refers to a molecule that exists apart from its native environment and is therefore not a product of nature. An isolated molecule may exist in a purified form or may exist in a non-native environment.

In one aspect, the retinal derivative can be a 9-cis-retinyl ester or ether of the following formula XIV:

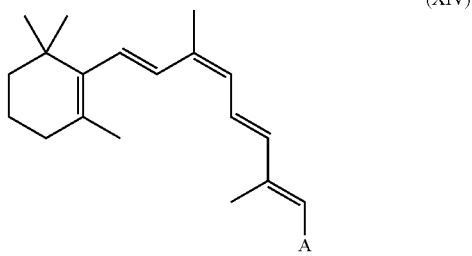

(XIV)

In some embodiments, A is CH2OR, where R can be an aldehyde group, to form a retinyl ester. A suitable aldehyde group is a C1 to C24 straight chain or branched aldehyde group. In additional embodiments, the aldehyde groups is a C1 to C14 straight chain or branched aldehyde group. In other embodiments, the aldehyde group is a C1 to C12 straight chain or branched aldehyde group, such as, for example, acetaldehyde, propionaldehyde, butyraldehyde, valeraldehyde, hexanal, heptanal, octanal, nonanal, decanal, undecanal, dodecanal. In other embodiments, R can be a C1 to C10 straight chain or branched aldehyde group, a C1 to C8 straight chain or branched aldehyde group or a C1 to C6 straight chain or branched aldehyde group. (As used herein, the term "group" refers to a radical covalently linked to the oxygen.) In some embodiments, the retinyl ester is not a naturally occurring retinal ester normally found in the eye.

In additional embodiments, R can be an aldehyde group of a dicarboxylic acid or other carboxylic acid (e.g., a hydroxyl acid) to form a retinyl ester (some of which are also referred to as retinoyl esters), such as oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

R can also be an alkane group, to form a retinyl alkane ether. Suitable alkane groups include, for example, C1 to C24 straight chain or branched alkyls, such as, for example, methane, ethane, butane, isobutane, pentane, isopentane, hexane, heptane, octane or the like. In some embodiments, the alkane group can be a linear, iso-, sec-, tert- or other branched lower alkyl ranging from C1 to C6. In other embodiments, the alkane group can be a linear, iso-, sec-, tert- or other branched medium chain length alkyl ranging from C8 to C14. In additional embodiments, the alkane group can be a linear, iso-, sec-, tert- or other branched long chain length alkyl ranging from C16 to C24.

R further can be an alcohol group, to form a retinyl alcohol ether. Suitable alcohol groups can be linear, iso-, sec-, tert- or other branched lower alcohols ranging from C1 to C6, linear, iso-, sec-, tert- or other branched medium chain length alcohols ranging from C8 to C14, or linear, iso-, sec-, tert- or other branched long chain length alkyl ranging from C16 to C24. In some embodiments, the alcohol group can be, for example, methanol, ethanol, butanol, isobutanol, pentanol, hexanol, heptanol, octanol, or the like.

R can also be a carboxylic acid, to form a retinyl carboxylic acid ether. Suitable alcohol groups can be linear, iso-, sec-, tert- or other branched lower carboxylic acids ranging from C1 to C6, linear, iso-, sec-, tert- or other branched medium chain length carboxylic acids ranging from C8 to C14, or linear, iso-, sec-, tert- or other branched long chain length carboxylic acids ranging from C16 to C24. Suitable carboxylic acid groups include, for example, acetic acid, propionic acid, butyric acid, valeric acid, caproic acid, caprylic acid, pelargonic acid, capric acid, lauric acid, oleic acid, stearic acid, palmitic acid, myristic acid, linoleic acid, succinic acid, fumaric acid or the like.

In another embodiments, the retinyl derivative is a retinyl hemiacetal, where A is CH(OH)OR. R can be any of the R groups set forth above in Formula XIV. R is typically a lower alkane, such as a methyl or ethyl group, or a C1 to C7 saturated and unsaturated, cyclic or acyclic alkane, with or without hetero atoms, as described herein.

In yet other embodiments, the retinyl derivative is a retinyl acetal, where A is CH (ORa)ORb. Each of Ra and Rb can be independently selected from any of the R groups set forth above in Formula XIV. Ra and Rb are typically a C1 to C7 saturated and unsaturated, cyclic or acyclic alkane, with or without hetero atoms, as described herein.

In yet a further embodiments, the retinyl derivative is a retinyl oxime, where A is CH:NOH, or CH:NOR. R can be any of the R groups set forth above in Formula XIV. R is typically a hydrogen, or an alkane.

Examples of suitable synthetic retinal derivatives include, for example, 9-cis-retinyl acetate, 9-cis-retinyl formate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, 9-cis-retinal oxime, 9-cis-retinal O-methyl oximes, 9-cis-retinal O-ethyl oximes, and 9-cis-retinal methyl acetals and hemi acetals, 9-cis-retinyl methyl ether, 9-cis-retinyl ethyl ether, and 9-cis-retinyl phenyl ether In a related aspect, the retinal derivative can be an 11-cis-retinyl ester or ether of the following formula XV:

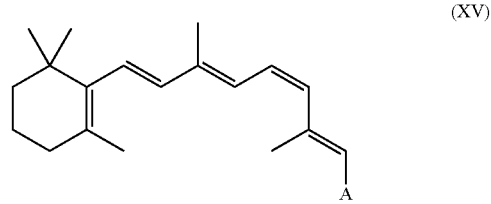

(XV)

A can be any of the groups set forth above in Formula XIV.

Examples of suitable synthetic retinal derivatives include, for example, 11-cis-retinyl acetate, 11-cis-retinyl formate, 11-cis-retinyl succinate, 11-cis-retinyl, 11-cis-retinyl citrate, 11-cis-retinyl ketoglutarate, 11-cis-retinyl fumarate, 11-cis-retinyl malate, 11-cis-retinal oxime,11-cis-retinal O-methyl oxime, 11-cis-retinal O-ethyl oximes and 11-cis-retinal methyl acetals and hemi acetals, 11-cis-retinyl methyl ether, 11-cis-retinyl ethyl ether.

In additional aspects, the synthetic retinal derivatives can be, for example, a derivative of a 9-cis-retinyl ester, a 9-cis-retinyl ether, an 11-cis-retinyl ester or an 11-cis-retinyl ethers such as, for example, an acyclic retinyl ester or ethers, a retinyl ester or ether with a modified polyene chain length, such as a trienoic or tetraenoic retinyl ester or ether; a retinyl ester or ether with a substituted polyene chain, such as alkyl, halogen or heteratom-substituted polyene chains; a retinyl ester or ether with a modified polyene chain, such as a trans- or cis-locked polyene chain, or with, for example, allene or alkyne modifications; and a retinyl ester or ether with a ring modification(s), such as heterocyclic, heteroaromatic or substituted cycloalkane or cycloalkene rings.

In other embodiments, the synthetic retinal derivative can be a retinyl ester or ether of the following formula XVI:

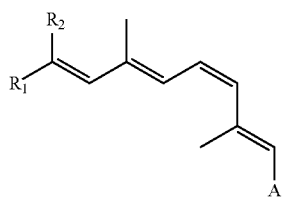

(XVI)

A can be any of the groups set forth above for formula (XIV). R1 and R2 can be independently selected from linear, iso-, sec-, tert- and other branched alkyl groups as well as substituted alkyl groups, substituted branched alkyl, hydroxyl, hydroalkyl, amine, amide, or the like. R1 and R2 can independently be lower alkyl, which means straight or branched alkyl with 1-6 carbon atom(s) such as methyl, ethyl, propyl, isopropyl, butyl, isobutyl, tert-butyl, pentyl, hexyl, or the like. Suitable substituted alkyls and substituted branch alkyls include, for example, alkyls, branched alkyls and cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

In certain additional embodiments, R1 or R2 can be a cyclo-alkyl such as, for example, hexane, cyclohexene, benzene as well as a substituted cyclo-alkyl. Suitable substituted cyclo-alkyls include, for example, cyclo-alkyls substituted with oxygen, hydroxyl, nitrogen, amide, amine, halogen, heteroatom and/or other groups. Suitable heteroatoms include, for example, sulfur, silicon, and fluoro- or bromo-substitutions.

The synthetic retinal derivative also can have a modified polyene chain length, such as the following formula XVII:

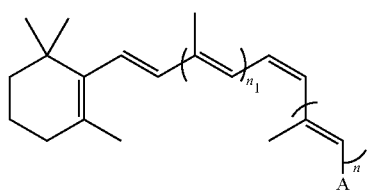

(XVII)

A can be any of the groups set forth above for formula (XIV). The polyene chain length can be extended by 1, 2, or 3 alkyl, alkene or alkylene groups. According to formula (XVI), each n and n1 can be independently selected from 1, 2, or 3 alkyl, alkene or alkylene groups, with the proviso that the sum of the n and n1 is at least 1.

The synthetic retinal derivative also can have a substituted polyene chain of the following formula XVIII:

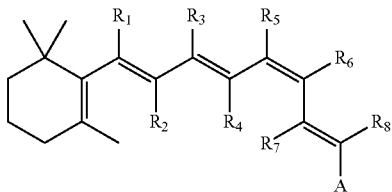

(XVIII)

A can be any of the groups set forth above for formula (XIV). Each of R1 to R8 can be independently selected from hydrogen, alkyl, branched alkyl, cyclo-alkyl, halogen, a heteratom, or the like. Suitable alkyls include, for example, methyl, ethyl, propyl, substituted alkyl (e.g., alkyl with hydroxyl, hydroalkyl, amine, amide) or the like. Suitable branched alkyls can be, for example, isopropyl, isobutyl, substituted branched alkyl, or the like. Suitable cyclo-alkyls can include, for example, cyclohexane, cycloheptane, and other cyclic alkanes as well as substituted cyclic alkanes such as substituted cyclohexane or substituted cycloheptane. Suitable halogens include, for example, bromine, chlorine, fluorine, or the like. Suitable heteroatoms include, for example, sulfur, silicon, and fluoro- or bromo-substitutions. Suitable substituted alkyls, substituted branch alkyls and substituted cyclo-alkyls include, for example, alkyls, branched alkyls and cyclo-alkyls substituted with oxygen, hydroxyl, nitrogen, amide, amine, halogen, heteroatom or other groups. In exemplary embodiments, the synthetic retinal derivative is selected from the following: a 9-ethyl-11-cis-retinyl ester, ether, oxime, acetal or hemiacetal; a 7-methyl-11-cis-retinyl ester, ether, oxime, acetal or hemiacetal; a 13-desmethyl-11-cis-retinyl ester, ether, oxime, acetal or hemiacetal; an 11-cis-10-F-retinyl ester, ether, oxime, acetal or hemiacetal; an 11-cis-10-Cl-retinyl ester, ether, oxime, acetal or hemiacetal; an 11-cis-10-methyl-retinyl ester, ether, oxime, acetal or hemiacetal; an 11-cis-10-ethyl-retinyl ester, ether, oxime, acetal or hemiacetal; a 9-cis-10-F-retinyl ester, ether, oxime, acetal or hemiacetal; a 9-cis-10-Cl-retinyl ester, ether, oxime, acetal or hemiacetal; a 9-cis-10-methyl-retinyl ester, ether, oxime, acetal or hemiacetal; a 9-cis-10-ethyl-retinyl ester, ether, oxime, acetal or hemiacetal; an 11-cis-12-F-retinyl ester, ether, oxime, acetal or hemiacetal; an 11-cis-12-Cl-retinyl ester, ether, oxime, acetal or hemiacetal; an 11-cis-12-methyl-retinyl ester, ether, oxime, acetal or hemiacetal; an 11-cis-10-ethyl-retinyl ester, ether, oxime, acetal or hemiacetal; a 9-cis-12-F-retinyl ester, ether, oxime, acetal or hemiacetal; a 9-cis-12-Cl-retinyl ester, ether, oxime, acetal or hemiacetal; a 9-cis-12-methyl-retinyl ester, ether, oxime, acetal or hemiacetal; an 11-cis-14-F-retinyl ester, ether, oxime, acetal or hemiacetal; an 11-cis-14-methyl-retinyl ester, ether, oxime, acetal or hemiacetal; an 11-cis-14-ethyl-retinyl ester, ether, oxime, acetal or hemiacetal; a 9-cis-14-F-retinyl ester, ether, oxime, acetal or hemiacetal; a 9-cis-14-methyl-retinyl ester, ether, oxime, acetal or hemiacetal; a 9-cis-14-ethyl-retinyl ester, ether, oxime, acetal or hemiacetal; or the like.

The synthetic retinal derivative further can have a modified ring structure. Suitable examples include, for example, derivatives containing ring modifications, aromatic analogs and heteroaromatic analogs of the following formulae XIX, XX and XXI, respectively:

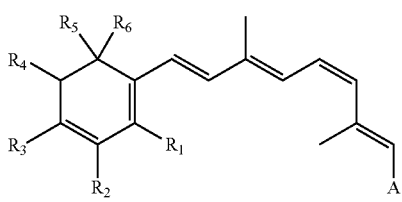
(XIX)

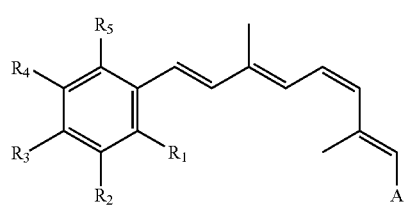
(XX)

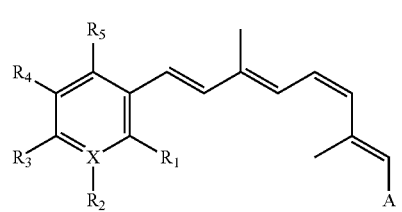
(XXI)

A can be any of the groups set forth above for formula (XIV). Each of R1 to R6, as applicable, can be independently selected from hydrogen, alkyl, substituted alkyl, hydroxyl, hydroalkyl, amine, amide, halogen, a heteratom, or the like. Suitable alkyls include, for example, methyl, ethyl, propyl, isopropyl, butyl, isobutyl or the like. Suitable halogens include, for example, bromine, chlorine, fluorine, or the like. Suitable heteroatoms include, for example, sulfur, silicon, or nitrogen. In formulae VII, X can be, for example, sulfur, silicon, nitrogen, fluoro- or bromo-substitutions.

The synthetic retinal derivative also can have a modified polyene chain. Suitable derivatives include, for example, those with a trans/cis locked configuration, 6s-locked analogs, as well as modified allene, alkene, alkyne or alkylene groups in the polyene chain. In one example, the derivative is an 11-cis-locked analog of the following formula XXII:

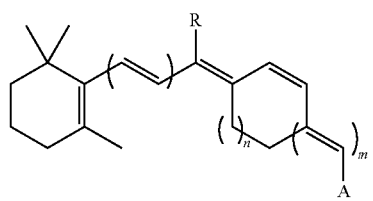
(XXII)

A can be any of the groups set forth above for formula (XIV). R3 can be, for example, hydrogen, methyl or other lower alkane or branch alkane. n can be 0 to 4; m plus 1 equals 1, 2 or 3.

In a specific embodiment, the synthetic retinal derivative is an 11-cis-locked analog of the following formula XXIII:

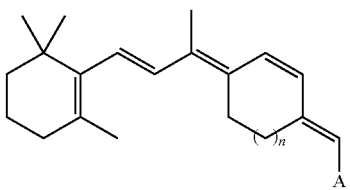
(XXIII)

n can be 1 to 4. A can be any of the groups set forth above for formula (XIV).

In certain exemplary embodiments, the synthetic retinal derivative is a 9,11,13-tri-cis-7-ring retinyl ester or ether, an 11,13-di-cis-7-ring retinyl ester or ether, an 11-cis-7-ring retinyl ester or ether or a 9,11-di-cis-7-ring retinyl ester or ether.

In another example, the synthetic retinal derivative is a 6s-locked analog of formula XXIV. A can be any of the groups set forth above for formula (XIV). $R_1$ and $R_2$ can be independently selected from hydrogen, methyl and other lower alkyl and substituted lower alkyl. $R_3$ can be independently selected from an alkene group at either of the indicated positions.

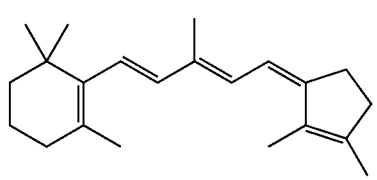
(XXV)

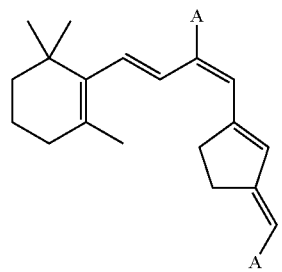
(XXVI)

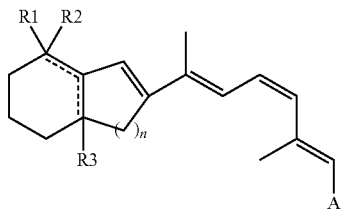
(XXIV)

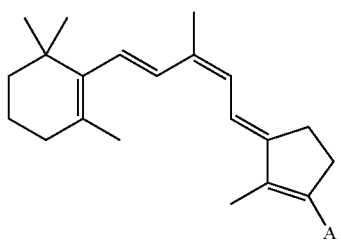
(XXVII)

In other embodiments, the synthetic retinal derivative can be a 9-cis-ring-fused derivative, such as, for example, those shown in formulae XXV-XXVII. A can be any of the groups set forth above for formula (XIV).

In yet another embodiment, the synthetic retinal derivative is of the following formula XXVIII or XXIXI.

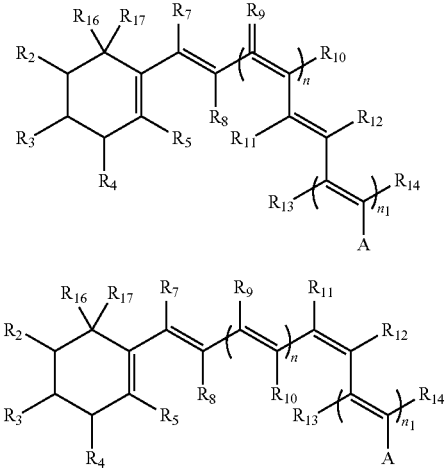

(XXVIII)

(XXIX)

A can be any of the groups set forth above for formula (XIV). Each of R2 to R5, R7 to R14, R16 and R17 can be absent or independently selected from hydrogen, alkyl, branched alkyl, halogen, hydroxyl, hydroalkyl, amine, amide, a heteroatom, or the like. Suitable alkyls include, for example, methyl, ethyl, propyl, substituted alkyl (e.g., alkyl with hydroxyl, hydroalkyl, amine, amide), or the like. Suitable branched alkyl can be, for example, isopropyl, isobutyl, substituted branched alkyl, or the like. Suitable halogens include, for example, bromine, chlorine, fluorine, or the like. Suitable heteroatoms include, for example, sulfur, silicon, and fluoro- or bromo-substitutions. Suitable substituted alkyls and substituted branch alkyls include, for example, alkyls and branched alkyls substituted with oxygen, hydroxyl, nitrogen, amide, amine, halogen, heteroatom or other groups. Each of n and n1 can be independently selected from 1, 2, or 3 alkyl, alkene or alkylene groups, with the proviso that the sum of the n and n1 is at least 1. In addition, R3-R4 and/or R2-R1 can comprise an alkene group in the cyclic carbon ring, in which case. In certain embodiments, R10 and R13 together can form a cyclo-alkyl, such as a five, six, seven or eight member cyclo-alkyl or substituted cyclo-alkyl, such as, for example, those shown in Formulae XXII, XXIII, XXVI, XXVI and XXVII.

In another embodiment of the invention, synthetic retinal derivatives are 9-cis-retinyl esters of the following formula (XXX):

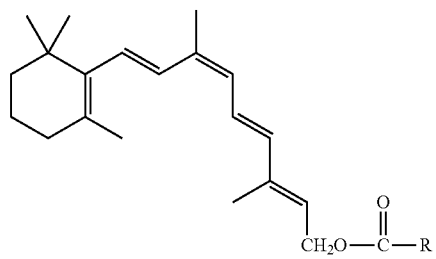

(XXX)

wherein R is an alkyl group or an alkenyl group.

In this embodiment, "alkyl" refers to a straight or branched hydrocarbon chain radical consisting solely of carbon and hydrogen atoms, containing no unsaturation, having up to twenty two carbon atoms. In certain embodiments, an alkyl may comprise twelve to seventeen carbon atoms (also referred to as "C12-17 alkyl"). In certain embodiments, an alkyl may comprise twelve to fifteen carbon atoms (also referred to as "C12-15 alkyl"). In certain embodiments, an alkyl may comprise one to eight carbon atoms (also referred to as "C1-8 alkyl"). In other embodiments, an alkyl may comprise one to six carbon atoms (also referred to as "C1-6 alkyl"). In further embodiments, an alkyl may comprise one to four carbon atoms (also referred to as "C1-4 alkyl"). The alkyl is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one or more of the following substituents: halo (including —F, —Br, —Cl and —I), cyano (—CN), nitro (—NO2), oxo (=O), and hydroxyl (—OH).

"Alkenyl" refers to a straight or branched hydrocarbon chain radical consisting solely of carbon and hydrogen atoms, containing at least one unsaturation (i.e., C=C), having from two to up to twenty carbon atoms. In various embodiments, R is C12-17 alkenyl, C1-8 alkenyl, C1-6 alkenyl or C1-4 alkenyl. Unless stated otherwise specifically in the specification, an alkyl group may be optionally substituted by one or more of the following substituents: halo (including —F, —Br, —Cl and —I), cyano (—CN), nitro (—NO2), oxo (=O), and hydroxyl (—OH).

In certain embodiments, the 9-cis-retinyl esters are artificial retinoids that act as precursors (i.e., pre-drugs) of a pro-drug form of 9-cis-retinal. More specifically, the 9-cis-retinyl esters can be converted by the liver to a metabolic pro-drug form, namely fatty acid 9-cis-retinyl esters, which are stored in the liver in hepatic lipid droplets. Fatty acid 9-cis-retinyl esters and retinol are mobilized from the liver and enter the circulation where they travel to the eye and RPE. There, they are converted to 9-cis-retinal which ultimately combines with photoreceptor opsins to form active visual pigments.

A preferred 9-cis-retinyl ester is 9-cis-retinyl acetate (i.e., R is methyl). Also referred to as "9-cis-R-Ac", 9-cis-retinyl acetate is a pharmaceutical pre-drug, which is metabolized by the liver to fatty acid 9-cis-retinyl esters, such as 9-cis-retinyl palmitate. Fatty acid 9-cis-retinyl esters and retinol are then converted to 9-cis-retinal in the eye and RPE as replacement of deficient chromophores such as 11-cis-retinal.

9-cis-R-Ac can be prepared by initially converting all-trans-retinyl acetate (Sigma-Aldrich) to a mixture of 9-cis-retinyl acetate and all-trans-retinyl acetate in the presence of a palladium catalyst (e.g., palladium salts, palladium oxides). The mixture of 9-cis-retinyl acetate and all-trans-retinyl acetate are then hydrolyzed to produce a mixture of 9-cis-retinol and all-trans-retinol. The pure 9-cis-retinol can be isolated by selective recrystallization and further esterified to pure 9-cis-R-Ac. A detailed description of the processes for preparing and purifying 9-cis-R-Ac can be found, for example, in GB Patent No. 1452012.

In other embodiments, the retinyl esters are pro-drugs (rather than precursors of pro-drugs) and can be directly converted to 9-cis-retinal in the eye and RPE. The pro-drug forms of the 9-cis-retinyl esters are typically fatty acid 9-cis-retinyl esters, in which R is a C11-21 alkyl. As used herein, "fatty acid" refers to a carboxylic acid having a long aliphatic chain, which can be saturated (alkyl) or unsaturated (alkenyl). Typically, the aliphatic chain contains at least 11 carbons and can be as long as 21 carbons. Exemplary fatty acids include, without limitation, lauric acid, palmitic acid, palmitoleic acid, oleic acid, linoleic acid, and linolenic acid.

Thus, in one embodiment, R is a C15 alkyl, and the 9-cis-retinyl ester of Formula (XXX) is 9-cis-retinyl palmitate.

In a further embodiment, R is a C17 alkyl, and the 9-cis-retinyl ester of Formula (XXX) is 9-cis-retinyl stearate.

In other embodiment, R is a C17 alkenyl, and the 9-cis-retinyl ester of Formula (XXX) is 9-cis-retinyl oleate.

The 9-cis-retinyl esters described herein can be prepared from 9-cis-retinol using appropriate esterifying agents in a manner similar to the preparation of 9-cis-R—Ac, the methods of which are within the knowledge of one skilled in the art.

Methods of making synthetic retinals and derivatives are disclosed in, for example, the following references: Anal. Biochem. 272:232-42 (1999); Angew. Chem. 36:2089-93 (1997); Biochemistry 14:3933-41 (1975); Biochemistry 21:384-93 (1982); Biochemistry 28:2732-39 (1989); Biochemistry 33:408-16 (1994); Biochemistry 35:6257-62 (1996); Bioorganic Chemistry 27:372-82 (1999); Biophys. Chem. 56:31-39 (1995); Biophys. J. 56:1259-65 (1989); Biophys. J. 83:3460-69 (2002); Chemistry 7:4198-204 (2001); Chemistry (Europe) 5:1172-75 (1999); FEBS 158:1 (1983); J. American Chem. Soc. 104:3214-16 (1982); J. Am. Chem. Soc. 108:6077-78 (1986); J. Am. Chem. Soc. 109:6163 (1987); J. Am. Chem. Soc. 112:7779-82 (1990); J. Am. Chem. Soc. 119:5758-59 (1997); J. Am. Chem. Soc. 121:5803-04 (1999); J. American Chem. Soc. 123:10024-29 (2001); J. American Chem. Soc. 124:7294-302 (2002); J. Biol. Chem. 276:26148-53 (2001); J. Biol. Chem. 277:42315-24 (2004); J. Chem. Soc.—Perkin T. 1:1773-77 (1997); J. Chem. Soc.—Perkin T. 1:2430-39 (2001); J. Org. Chem. 49:649-52 (1984); J. Org. Chem. 58:3533-37 (1993); J. Physical Chemistry B 102:2787-806 (1998); Lipids 8:558-65; Photochem. Photobiol. 13:259-83 (1986); Photochem. Photobiol. 44:803-07 (1986); Photochem. Photobiol. 54:969-76 (1991); Photochem. Photobiol. 60:64-68 (1994); Photochem. Photobiol. 65:1047-55 (1991); Photochem. Photobiol. 70:111-15 (2002); Photochem. Photobiol. 76:606-615 (2002); Proc. Natl Acad. Sci. USA 88:9412-16 (1991); Proc. Natl Acad. Sci. USA 90:4072-76 (1993); Proc. Natl Acad. Sci. USA 94:13442-47 (1997); and Proc. R. Soc. Lond. Series B, Biol. Sci. 233(1270): 55-76 1988) (the disclosures of which are incorporated by reference herein).

Retinyl esters can be formed by methods known in the art such as, for example, by acid-catalyzed esterification of a retinol with a carboxylic acid, by reaction of an acyl halide with a retinol, by transesterification of a retinyl ester with a carboxylic acid, by reaction of a primary halide with a carboxylate salt of a retinoic acid, or the like. In an exemplary embodiment, retinyl esters can be formed by acid-catalyzed esterification of a retinol with a carboxylic acid, such as, acetic acid, propionic acid, butyric acid, valeric acid, caproic acid, caprylic acid, pelargonic acid, capric acid, lauric acid, oleic acid, stearatic acid, palmitic acid, myristic acid, linoleic acid, succinic acid, fumaric acid or the like. In another exemplary embodiment, retinyl esters can be formed by reaction of an acyl halide with a retinol (see, e.g., Van Hooser et al., Proc. Natl. Acad. Sci. USA, 97:8623-28 (2000)). Suitable acyl halides include, for example, acetyl chloride, palmitoyl chloride, or the like.

Retinyl ethers can be formed by methods known in the art, such as for example, reaction of a retinol with a primary alkyl halide.

In certain embodiments, trans-retinoids can be isomerized to cis-retinoids by exposure to UV light. For example, all-trans-retinal, all-trans-retinol, all-trans-retinyl ester or all-trans-retinoic acid can be isomerized to 9-cis-retinal, 9-cis-retinol, 9-cis-retinyl ester or 9-cis-retinoic acid, respectively. trans-Retinoids can be isomerized to 9-cis-retinoids by, for example, exposure to a UV light having a wavelength of about 365 nm, and substantially free of shorter wavelengths that cause degradation of cis-retinoids, as further described herein.

Retinyl acetals and hemiacetals can be prepared, for example, by treatment of 9-cis- and 11-cis-retinals with alcohols in the presence of acid catalysts. Water formed during reaction is removed, for example by Al2O3 of a molecular sieve.

Retinyl oximes can be prepared, for example, by reaction of a retinal with hydroxylamine, O-methyl- or O-ethylhydroxyl amine, or the like.

Retinyl esters can be formed by methods known in the art such as, for example, by acid-catalyzed esterification of a retinol with a carboxylic acid, by reaction of an acyl halide with a retinol, by transesterification of a retinyl ester with a carboxylic acid, by reaction of a primary halide with a carboxylate salt of a retinoic acid, by acid-catalyzed reaction of an anhydride with a retinol, or the like. In an example, retinyl esters can be formed by acid-catalyzed esterification of a retinol with a carboxylic acid, such as, acetic acid, propionic acid, butyric acid, valeric acid, caproic acid, caprylic acid, pelargonic acid, capric acid, lauric acid, oleic acid, stearatic acid, palmitic acid, myristic acid, linoleic acid, succinic acid, fumaric acid or the like. In another example, retinyl esters can be formed by reaction of an acyl halide with a retinol (Van Hooser et al., Proc. Natl. Acad. Sci. USA, 97:8623-28 (2000)). Suitable acyl halides include, for example, acetyl chloride, palmitoyl chloride, or the like.

In another embodiment of the invention, the synthetic retinal derivative is a retinyl ester. Retinyl ethers can be formed by methods known in the art, such as for example, reaction of a retinol with a primary alkyl halide.

In another embodiment of the invention, trans-retinoids can be isomerized to cis-retinoids by exposure to UV light. For example, all-trans-retinal, all-trans-retinol, all-trans-retinyl ester or all-trans-retinoic acid can be isomerized to 9-cis-retinal, 9-cis-retinol, 9-cis-retinyl ester or 9-cis-retinoic acid, respectively, by exposure to a UV light having a wavelength of about 365 nm, and substantially free of shorter wavelengths that cause degradation of cis-retinoids, as further described herein.

In another embodiment of the invention, the synthetic retinal derivative is a retinyl acetal or hemiacetal, which can be prepared, for example, by treatment of 9-cis- and 11-cis-retinals with alcohols in the presence of acid catalysts. Water formed during reaction is removed, for example by Al2O3 of a molecular sieve.

In another embodiment of the invention, the synthetic retinal derivatives is a retinyl oxime, which can be prepared, for example, by reaction of a retinal with hydroxylamine, O-methyl- or O-ethylhydroxyl amine, or the like.

The synthetic retinal derivative of the invention can be substantially pure in that it contains less than about 5% or less than about 1%, or less than about 0.1%, of other retinoids. One or more synthetic retinal derivatives may be used in the therapeutic regimens of the invention.

Pharmaceutically Acceptable Compositions of the Invention

Synthetic retinal derivatives of the invention can be formulated, for example, as pharmaceutically acceptable compositions for local administration to the eye and/or for systemic administration such as intravenous, intramuscular, subcutaneous, enteral, parenteral or oral administration.

Synthetic retinal derivatives of the invention can be formulated for administration using pharmaceutically acceptable vehicles as well as techniques routinely used in the art. A vehicle can be selected according to the solubility of the synthetic retinal derivative. Suitable pharmaceutically acceptable compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, butylated hydroxyanisole (BHA) and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

Synthetic retinal derivatives used in the therapeutic regimens of the invention can be delivered to the eye by any suitable means, including, for example, oral, intravenous, intramuscular or local administration. Modes of local administration can include, for example, eye drops, intraocular injection or periocular injection, or delivery via a controlled release drug delivery formulation and/or device. Periocular injection typically involves injection of the synthetic retinal derivative into the conjunctiva or to the tenon (the fibrous tissue overlying the eye). Intraocular injection typically involves injection of the synthetic retinal derivative into the vitreous. The administration can be non-invasive, such as by eye drops or in oral dosage form.

In certain embodiments, the synthetic retinal derivative is formulated into a formulation suitable for oral or local delivery to the eyes. Most of the synthetic retinal derivatives are oily substances and lipophilic and are therefore easily miscible with one or more lipid vehicles.

Certain synthetic retinal derivatives of the invention (e.g., 9-cis-retinyl esters) are light- and oxygen-sensitive. It is therefore desirable to maintain the stability and maximize the efficacy and shelf-life of the formulation. A suitable lipid vehicle may be selected based on its ability to stabilize the 9-cis-retinyl esters suspended or solubilized therein. As used herein, "lipid" or "lipid vehicle" refers to one or a blend of fatty acid esters. In various embodiments, the lipid vehicle comprises one or more triglycerides, which are formed when a single glycerol is esterified by three fatty acids. Triglycerides include both vegetable oils and animal fats. In various embodiments, the lipid vehicle comprises more than 50 w/w % polyunsaturated fatty acids, the polyunsaturated fatty acids including an omega-6 fatty acid and an omega-3 fatty acid in a ratio (by weight) of less than 15.

In a preferred embodiment, the synthetic retinal derivative is formulated into an oral formulation comprising a 9-cis-retinyl ester and a lipid vehicle. In a further embodiment, the 9-cis-retinyl ester is 9-cis-retinyl acetate, and the lipid vehicle is soy bean oil. The description of additional lipid vehicles can be found in, for example, International Patent Application No. PCT/US2009/059126 in the name of QLT Inc., the relevant disclosure of which is incorporated herein in its entirety.

The present invention also provides kits that contain a synthetic retinal derivative of the invention or a pharmaceutically acceptable composition of the invention. The kit also includes instructions for the use of the synthetic retinal derivative or the pharmaceutically acceptable composition in the therapeutic regimens and methods of the invention. Preferably, a commercial package will contain one or more unit doses of the synthetic retinal derivative or the pharmaceutically acceptable composition for use in a therapeutic regimen or method of the invention. For example, such a unit dose may be an amount sufficient for the preparation of an intraocular injection. Alternatively, such a unit dose may be an amount sufficient to effect treatment or amelioration of a visual disorder when administered to a human subject. It will be evident to those of ordinary skill in the art that for those synthetic retinal derivatives of the invention or pharmaceutically acceptable compositions of the invention which are light and/or air sensitive may require special packaging and/or formulation. For example, packaging may be used for the kit which is opaque to light, and/or sealed from contact with ambient air, and/or formulated with suitable coatings or excipients.

Dosage, Dosage Frequency and Modes of Administration

The synthetic retinal derivatives and pharmaceutically acceptable pharmaceutical compositions comprising the synthetic retinal derivatives used in the therapeutic regimens of the invention may be in the form of an oral dose. In one embodiment, a pharmaceutically acceptable composition of the invention comprising a synthetic retinal derivative and a lipid vehicle is administered orally to the subject in the therapeutic regimen of the invention. In another embodiment of the invention, the orally-administered pharmaceutically acceptable composition of the invention comprises a 9-cis-retinyl ester and soybean oil. In another embodiment of the invention, the orally-administered pharmaceutically acceptable composition comprises 9-cis-retinyl acetate or 9-cis-retinyl succinate and soybean oil (USP grade).

Oral administration of the synthetic retinal derivatives of the invention has several potential advantages, including exposure of all photoreceptors in both eyes of the subject undergoing the therapeutic regimen of the invention to therapy, lack of surgical intervention, and cessation of administration at any time. In a preferred embodiment, treatment may begin in subjects diagnosed with LCA just after birth and continue throughout the subject's life. In other embodiments, therapeutic regimens of the invention may be used in combination with vector-mediated gene transfer therapy for replacement of one or more genes, for example, RPE65 or LRAT, associated with the visual cycle in a subject, for example in subjects who have already received gene therapy as a method for treating or ameliorating visual disorders associated with endogenous retinoid deficiency in a subject.

Additional suitable dosage forms for the synthetic retinal derivatives of the invention include those formulated for injection. For example, a synthetic retinal derivative for use in a therapeutic regimen of the invention can be provided in an injection grade saline solution, in the form of an injectable liposome solution, or other carriers or vehicles. In certain embodiments, the synthetic retinal derivatives described herein can be formulated for local injection into the eyes. Intraocular and periocular injections are known to those skilled in the art and are described in numerous publications including, for example, Ophthalmic Surgery: Principles of Practice, Ed., G. L. Spaeth, W. B. Sanders Co., Philadelphia, Pa., U.S.A., pages 85-87 (1990). In other embodiments, the synthetic retinal derivatives can be formulated for systemic delivery via subcutaneous injection. In one embodiment, for subcutaneous injection, a 9-cis-retinyl ester may be formulated in a lipid vehicle, such as soybean oil.

A synthetic retinal derivative can also be administered in a therapeutic regimen of the invention in a time release formulation and/or device, for example in a composition which includes a slow release polymer, or via a time-release, delayed release or sustained release delivery system to afford delivery of a synthetic retinal derivative over the course of one or more of the dosing phase time periods. Such systems can avoid repeated administrations of compositions described in this disclosure. Numerous types of drug release delivery systems are known to those of skill in the art, including ophthalmic drug delivery devices designed for positioning in or near the ocular tissues, for example, suitable for placement adjacent the sclera, or in the punctum, or within the vitreous, and capable of delivering one or more synthetic retinoids of the present invention on a time-released, or delayed release or sustained release fashion. The synthetic retinal derivative for use in the therapeutic regimens of the invention can be prepared with a carrier(s) that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

The therapeutic regimens of the present invention produce meaningful improvement or recovery of vision that is long lasting, while reducing chronic toxic side effects can be greatly reduced, and thus in one embodiment, the therapeutic regimens of the present invention may be suitable as a long-term (chronic) therapeutic regimen.

The length of the period of time between the first dosing period and the subsequent dosing period may optionally be based on the persistence or increase in one or more of the subject's visual function parameters, as defined herein. Dosing-dependent effects or improvement in the subject's visual functions may be observed and assessed on an individual basis to allow for customization of the subject's dosing requirements. Alternatively, commencement of any subsequent dosing period may be based on a decrease in one or more of the subject's visual function parameters relative to previous efficacy assessments during first dosing period and any resting period. For instance, the efficacy of the subject's dosing may be assessed at, for example, about 1 month, 4 months, 6 months, 8 months, 11 months following the first dosing period. At any point of the assessment, a subsequent dosing period may commenced based on regression or a return to baseline of one or more of the subject's visual function parameters during any resting period.

Evaluation of Therapeutic Effect

The effectiveness of the therapeutic regimens of the invention in treating or ameliorating visual disorders in a subject associated with an endogenous retinoid deficiency can be evaluated based on several measures of vision function, including those as described below.

Improvements in the subject's visual functions in one or both eyes may be evaluated based on measures of visual field, visual acuity, and retinal sensitivity testing, as well as electroretinograms, dynamic pupillary response, nystagmus, cortical visual function, color vision, visual mobility testing, and patient-reported outcomes of quality of life/ability to perform life tasks. Improvements in the subject's visual functions in one or both eyes during a therapeutic regimen of the invention can be demonstrated by comparing the subject's visual functions of each eye with a baseline measure of the subject's visual functions of each eye prior to the treatment by a therapeutic regimen of the invention or by comparing the subject's visual functions of each eye with a comparable human visual system not receiving the treatment.

It was demonstrated (see Examples 2 and 3 below) that one or more of the visual function parameters listed below improved rapidly in three LCA patients, all of which had genetic mutations in the LRAT gene. These improvements, particularly in visual field and visual acuity, could be sustained for up to 11 months following an initial dosing period of one week. Thus, it has been identified that, for subjects with endogenous retinoid deficiency, a population of dormant photoreceptors are capable of rapidly responding to external manipulation provided by the therapeutic regimen of the invention described herein, i.e., by the administration of a synthetic retinal derivative as disclosed herein. Efficacy is also observed in LCA subjects with mutations in the RPE65 gene (Examples 4 and 5) as well as subjects with RP (Examples 7 and 8).

1. Visual Field

The visual field is an individual's entire scope of vision, including the central and peripheral (side) vision of each eye. Normal human visual field extends to approximately 60 degrees nasally (toward the nose, or inward) in each eye, to 100 degrees temporally (away from the nose, or outwards), and approximately 60 degrees above and 75 below the horizontal meridian.

Subjects having visual disorders as described herein may have various degrees of impairments that can span from non-detectable to significantly contracted visual field.

Thus, in one embodiment of the therapeutic regimens of the invention, the subject's visual field improves, temporally and/or nasally, in the initial dosing period as compared to the baseline of the subject's visual field obtained prior to the initial dosing period. In certain embodiments, the subject's visual field continues to improve during the resting period as compared to the improvement in the subject's visual field during the initial dosing period. In certain embodiments, the improvement in the subject's visual field observed during the initial dosing period is sustained during the resting period.

In various embodiments of the present invention, for example for subjects with LRAT or RPE65 mutation, including without limitation, LCA or arRP patients, the subject's visual field expands by at least 5 degrees or at least 10 degrees nasally, and at least 20 degrees, or at least 30 degrees or at least 40 degrees temporally during the initial dosing period.

Commencement of the subsequent dosing period may begin upon assessment of the improvement of the subject's visual field during the initial dosing period and during the resting period. For example, the subsequent dosing period may commence if the subject's visual field returns to a level prior to the initial dosing period or to a pre-determined level during the initial resting period.

Visual field can be tested by art-recognized techniques and standards, such as Kinetic Perimetry by Goldmann Visual Field testing (GVF) or Static Perimetry by Humphrey Visual Field Analyzer (HFA).

2. Visual Acuity

Visual acuity refers to acuteness or clearness of vision, especially form vision, which is dependent on the sharpness of the retinal focus within the eye and the sensitivity of the interpretative faculty of the brain. Visual acuity is a measure of the spatial resolution of the visual processing system and is usually tested in a manner to optimize and standardize the conditions.

Visual acuity testing is the most common method for assessing a subject's visual function, and the Early Treatment Diabetic Retinopathy Study (ETDRS) method is the gold-standard for measuring treatment effects in clinical trials.

However, this method measures vision under high contrast and standard room lighting conditions. Subjects with LCA typically have the most difficulty with vision under conditions of low luminance. The Smith-Kettlewell Institute Low Luminance (SKILL) Chart was designed to assess vision under conditions of low contrast that simulates low lighting, through a test performed with standard indoor lighting. The SKILL Chart has a high-contrast near-acuity chart on one side (black letter on white), and a low-luminance, low-contrast chart on the other (gray letters on a dark background). The low reflectance of the dark side of the card simulates testing in a dim environment. Repeatability of acuity testing with the SKILL card has been shown to be as good as repeatability of Snellen acuity.

In certain embodiments of the present invention, the degree of improvement in visual acuity over baseline may be dependent on the subject's baseline visual acuity. For patients with very low visual acuity (light perception or hand waving, zero letters), clinically meaningful improvement may be associated with an improvement of 1-5 ETDRS letters. Patients with higher baseline VA (20-50 letters) may have a higher potential improvement from baseline based on their overall retinal health and architecture.

Thus, in one embodiment of the therapeutic regimens of the invention, the subject's visual acuity improves during the initial dosing period as compared to the subject's visual acuity level prior to the treatment during the initial dosing period, i.e, the subject's visual acuity baseline. In certain embodiments, the subject's visual acuity continues to improve during resting period as compared to the improvement in the subject's visual acuity level observed at the end of the initial dosing period. In certain embodiments, the improvement in the subject's visual acuity is sustained during the resting period at about the subject's visual acuity level at the end of the initial dosing period.

3. Retinal Sensitivity

A subject's retinal sensitivity can be measured by determining the absolute intensity threshold, that is, the minimum luminance of a test spot required to produce a visual sensation. Retinal sensitivity is related to the eye's ability to adjust to various levels of darkness and light and to detect contrast.

Full-field stimulus testing (FST) was developed to measure dark-adapted sensitivity using commercial equipment in patients unable to fixate (Roman, A. J. et al., Physiol. Meas. 28(8):N51-N56 (2007)). The test uses a full-field (Ganzfeld) white-flash stimulus presentation available in a commercial ERG dome (Diagnosys) and available software allows for reliable, efficient psycho-physical measures of absolute threshold, expressed in log luminance (log cd/m2). FST has previously been shown to measure rod and cone sensitivity to white, blue, and red stimuli in RPE65-deficient LCA patients who had limited or no ERG responses (Jacobson, S. G. et al., Invest Ophthalmol Vis Sci. 50(5):2368-2375 (2009)). Therefore, FST is a useful test to measure visual function in subjects having visual disorders associated with endogenous retinoid deficiency, including LCA or RP patients, or subjects having LRAT or RPE65 mutation.

Thus, in one embodiment of the therapeutic regimens of the invention, the subject's retinal sensitivity improves during the initial dosing period as compared to the subject's retinal sensitivity baseline prior to the treatment during the initial dosing period. In certain embodiments, the subject's retinal sensitivity continues to improve during the resting period as compared to the improvement in the subject's retinal sensitivity at the end of the initial dosing period. In certain embodiments, the improvement in the subject's retinal sensitivity is sustained during the resting period at about the subject's retinal sensitivity level at the end of the initial dosing period.

4. Electroretinograms (ERG)

ERG testing is a well-accepted standard test and is used routinely to diagnose and monitor progression of most inherited retinal diseases (IRD) including LCA. Physicians specializing in IRD agree that significant, repeatable improvements in ERG responses are indicative of improved visual function.

The three main types of traditional global or full-field ERG that evaluate general retinal response are scotopic, photopic, and flicker testing. A limitation of full-field ERG is that the recording is a massed potential from the whole retina. Unless 20% or more of the retina is affected with a diseased state, ERG recordings are usually normal (e.g., a legally blind person with macular degeneration, enlarged blind spot or other central scotomas may have normal global ERGs). Most LCA and RP subjects have virtually no measurable ERG recordings, yet many of these subjects can still see, some quite well. Recent gene therapy trials for LCA have not reported changes in full-field ERG results, which may be because the methods in these trials treated less than 10% of the retina, so the ERG results would not be expected to change.

5. Dynamic Pupillary Response (Pupillometry)

Pupillary responses (constriction of the pupil in response to a bright light stimulus) may be abnormal in subjects having a visual disorder as described herein. Dynamic pupillometry is a non-invasive method to record the pupillary response and monitor potential changes in response to treatment. Pupillary reflexes improved in LCA subjects with RPE65 deficiency after receiving gene therapy (Maguire, A. M. et al., New Engl J Med. 358:2240-2248 (2008)). This procedure may be performed with an appropriate pupillometer.

Thus, in one embodiment of the therapeutic regimens of the invention, the subject's pupillary response improves during the initial dosing period as compared to the subject's pupillary response baseline level prior to the treatment during the initial dosing period. In certain embodiments, the subject's pupillary response continues to improve during the resting period as compared to the subject's pupillary response level at the end of the initial dosing period. In certain embodiments, the improvement in the subject's pupillary response is sustained during the resting period at about the subject's pupillary response level at the end of the initial dosing period.

6. Nystagmus

Nystagmus is a form of involuntary eye movement that is frequently associated with visual impairment, including LCA. Nystagmus amplitude and frequency is measured non-invasively and can be used to monitor potential changes in response to treatment such as by videotaping the eye movements for qualitative clinical analysis of the subject's oscillation and strabismus. (Maguire, A. M. et al., New Engl J Med. 358:2240-2248 (2008)).

Thus, in one embodiment of the therapeutic regimens of the invention, the subject demonstrates a decrease in the amplitude and/or frequency of nystagmus during the initial dosing period. In another embodiment, the subject demonstrates a continued decrease in the amplitude and/or frequency of nystagmus during the resting period.

7. Cortical Visual Function

The therapeutic effectiveness of the therapeutic regimens of the invention may be monitored using effects of the subject's vision on cortical visual function as measured by functional magnetic resonance imaging (fMRI). Functional scans consist of a contrast sensitivity challenge, movement stimulus challenge, and higher level cognitive challenges. Data are normally displayed as percentage change in MRI signal from baseline. Maps of statistical significance will be displayed on the reconstructed cortical surface from each individual. The pre- and post-treatment scans will be directly compared in terms of the extent and magnitude of activation.

Thus, in one embodiment of the therapeutic regimens of the invention, the subject's cortical vision function improves during the initial dosing period as compared to the subject's cortical vision function baseline level prior to the treatment during the initial dosing period. In certain embodiments, the subject's cortical vision function continues to improve during the resting period as compared to the subject's cortical vision function level at the end of the initial dosing period. In certain embodiments, the improvement in the subject's cortical vision function is sustained during the resting period at about the subject's cortical vision function level at the end of the initial dosing period.

8. Color Vision

A color vision test checks a subject's ability to distinguish between different colors. Ishihara plates are used to detect, classify and estimate the degree of defect in color vision. Color vision testing is also used to evaluate the function of the optic nerve and hereditary retinal disease.

Color vision may be assessed by methods known in the art, including the Ishihara Color Test. The test consists of a number of colored plates, each of which contain a circle of dots appearing randomized in color and size. Within the pattern are dots which form a number visible to those with normal color vision.

Thus, in one embodiment of the therapeutic regimens of the invention, the subject's color vision improves during the initial dosing period as compared to the subject's color vision baseline level prior to the treatment during the initial dosing period. In certain embodiments, the subject's color vision continues to improve during resting period as compared to the subject's color vision level at the end of the initial dosing period. In certain embodiments, the improvement in the subject's color vision is sustained during the resting period at about the subject's color vision level at the end of the initial dosing period.

9. Dark Adaptation

Dark adaptation is defined as the recovery of light sensitivity by the retina in the dark after exposure to a bright light. Methods to measure dark adaptation are known in the art, including those methods defined in U.S. Pat. No. 7,494,222 and U.S. Pat. No. 7,798,646, the contents of which are herein incorporated by reference.

10. Visual Mobility

Visual mobility may be used as a measure of improved retinal function. Improvements in visual mobility can be determined by methods known in the art, including standardized obstacle courses and mazes, including those described in Bainbridge et al. N Engl J Med. 358:2231-9 (2008) and Maguire, A. M. et al., New Engl J Med. 358:2240-2248 (2008). Subjects may be assessed based on the time to navigate the course, or based on the number of times a subject bumps into obstacles or walks off course compared to the total number of obstacles present.

11. Visual Function Questionnaires

There are a number of known Visual Function Questionnaires (VFQ's) which may be used to assess improvement in a subject's visual function. One such questionnaire is the Children's Visual Function Questionnaire (CVFQ) (see, e.g., Birch, E. E. et al., J. AAPOS. 11:473-9 (2007)). This is a vision-specific quality-of-life instrument designed for use with parents of infants and young children.

Another questionnaire is the Low Luminance Questionnaire (LLQ). This is a questionnaire that has been developed specifically to assess visual performance of adults in low lighting conditions, such as night-time or darkened rooms (see, e.g., Owsley, C. et al., Invest Ophthalmol Vis Sci 47:528-535 (2006)). This questionnaire was validated in a population of older subjects similar to the population eligible for the clinical study described below and correlates to rod-mediated parameters of dark adaptation.

The use of the VFQ's assists in identifying subjective improvements in visual function, particularly with respect to activities of daily life following administration of a compound of the invention by the therapeutic regimens described herein.

12. Spectral Domain-Optical Coherence Tomography

Optical coherence tomography (OCT)/autofluorescence (FAF) machines, such as the Heidelberg Spectralis (Heidelberg Engineering, Germany), may be used to conduct ocular tomography scans. The analyses of the scans may provide information as to the overall retinal health, including visualization of the photoreceptor layer, the outer segments, and measurement of retinal thickness and to assess presence or absence of autofluorescence.

The following examples are provided merely as illustrative of various aspects of the invention and shall not be construed to limit the invention in any way.

EXAMPLES

Example 1

Safety Study

A study of an orally-delivered pharmaceutically acceptable composition of the invention was conducted in twenty (20) healthy human volunteers to determine the safety of a composition comprising 9-cis-retinyl acetate ((2E, 4E, 6Z, 8E)-3,7-dimethyl-9-(2,6,6-trimethylcyclohex-1-en-1-yl) nona-2,4,6, 8-tetraen-1-yl acetate) and butylated hydroxyanisole (BHA) dissolved in soybean oil (USP). The concentration of 9-cis-retinyl acetate in the composition was adjusted such that the volume to be administered was convenient. For the dosing range of the study, compositions of 1.25 mg/mL, 5.0 mg/mL and 20 mg/mL 9-cis-retinyl acetate were prepared, containing 0.10% w/w BHA in Soybean oil (USP). Six cohorts of subjects received escalating doses of the Composition orally from 1.25 mg/m2 up to 40 mg/m2. The composition was found to be well tolerated and there were no serious adverse events after 7 days of monitored therapy in a Phase I testing center. The most frequently reported side effects were headache (6 subjects, 12 events), facial flushing (2 subjects, 7 events), and a facial burning sensation (2 subjects, 6 events), which were primarily reported from the 40 mg/m2 dose group and collectively accounted for 25 of the 43 (58%) adverse events (AE) reported. In total, 41 of 43 AEs were of mild intensity. In some subjects, there was a modest and reversible elevation in triglycerides across all doses and a modest and reversible decline in high density lipoproteins (HDL) at the 10-40 mg/m2 doses.

Example 2

Efficacy Study for LCA Subjects

A study was designed to determine the efficacy of the composition of Example 1 orally administered to human subjects having LCA (caused by mutations of either LRAT or RPE65). Subjects received a once-daily loading dose of the composition orally (40 mg/m2) for 7 days. Subjects were treated on an outpatient basis, but they received study treatment in the research clinic under medical supervision for each day of treatment. During the study, subjects were required to limit vigorous physical activity (to avoid laboratory variability) and avoid excessive vitamin A intake in order to reduce the influence of such factors on the assessment of safety variables in this study.

Both eyes of each subject were evaluated separately. Protocol-defined assessments of visual function included: best-corrected visual acuity testing using Early Treatment Diabetic Retinopathy Study (ETDRS) testing followed by low/high contrast Smith-Kettlewell Institute Low Luminance (SKILL) charts; visual field testing using Goldmann perimetry; full-field electroretinogram (ERG); and full-field stimulus threshold testing (FST). Baseline ERGs, ETDRS, and SKILL tests were repeated twice. During and after treatment, visual function tests were conducted on Day 1, 7, 9/10, and 14/15.

It was at first believed that maximal effects of the composition would be achieved by limiting the amount of light reaching the retina and thus avoiding loss of the active chromophore, 9-cis-retinal, by bleaching. Therefore, in the first 2 subjects, an eye patch was worn on the eye with worse vision at all times until Day 7, except when undergoing the protocol-defined vision assessments. Surprisingly and unexpectedly, bleaching was not observed and the improvement in visual function persisted or continued to improve after Day 7. Consequently, after data from the first 2 subjects did not reveal any difference between the patched and unpatched eye, the requirement of an eye patch was removed from the protocol.

The efficacy assessments of this study for three subjects are set forth in Example 3 to 5 below.

Example 3

Efficacy Assessments

Both eyes of each subject were evaluated as described in Example 2. Protocol-defined assessments of vision were performed from the first day of dosing on Day 0 until Day 6. Follow-up visits were conducted until at least Day 13. If a clinical benefit was detected at Day 13, additional, optional follow-up visits were scheduled at biweekly intervals, with biweekly telephone calls between clinic visits, to continue assessing the status and duration of beneficial effects until a return to baseline was noted.

Subject #1 was followed for over 100 days, while Subject #2 was followed for over 75 days.

Early Treatment in Diabetic Retinopathy Study (ETDRS) best-corrected visual acuities were measured for each subject at 1 meter and 4 meters. Smith-Kettlewell Institute Low Luminance (SKILL) acuities, Ishihara color plates, Goldmann visual fields (with V4e and We targets, GVF), ISCEV standard cone and rod electroretinogram (ERG) parameters, including rod, mixed rod/cone, 30 Hz flicker and cone mediated ERGs (Diagnosys, LLC) were also measured. Full-field stimulus testing (FST) (Diagnosys, LLC) according to a published protocol was performed. Finally, in vivo retinal microscopy was performed by optical coherence tomography (OCT) and fundus autofluorescence was ascertained by Spectralis (Heidelberg Engineering). Efficacy was measured by comparing the results of pretreatment objective and subjective visual function testing with results of the same parameters obtained during and after the oral administration of the composition of Example 1.

Vision Characteristics of Subject #1 Before and After Treatment

Figure 2:
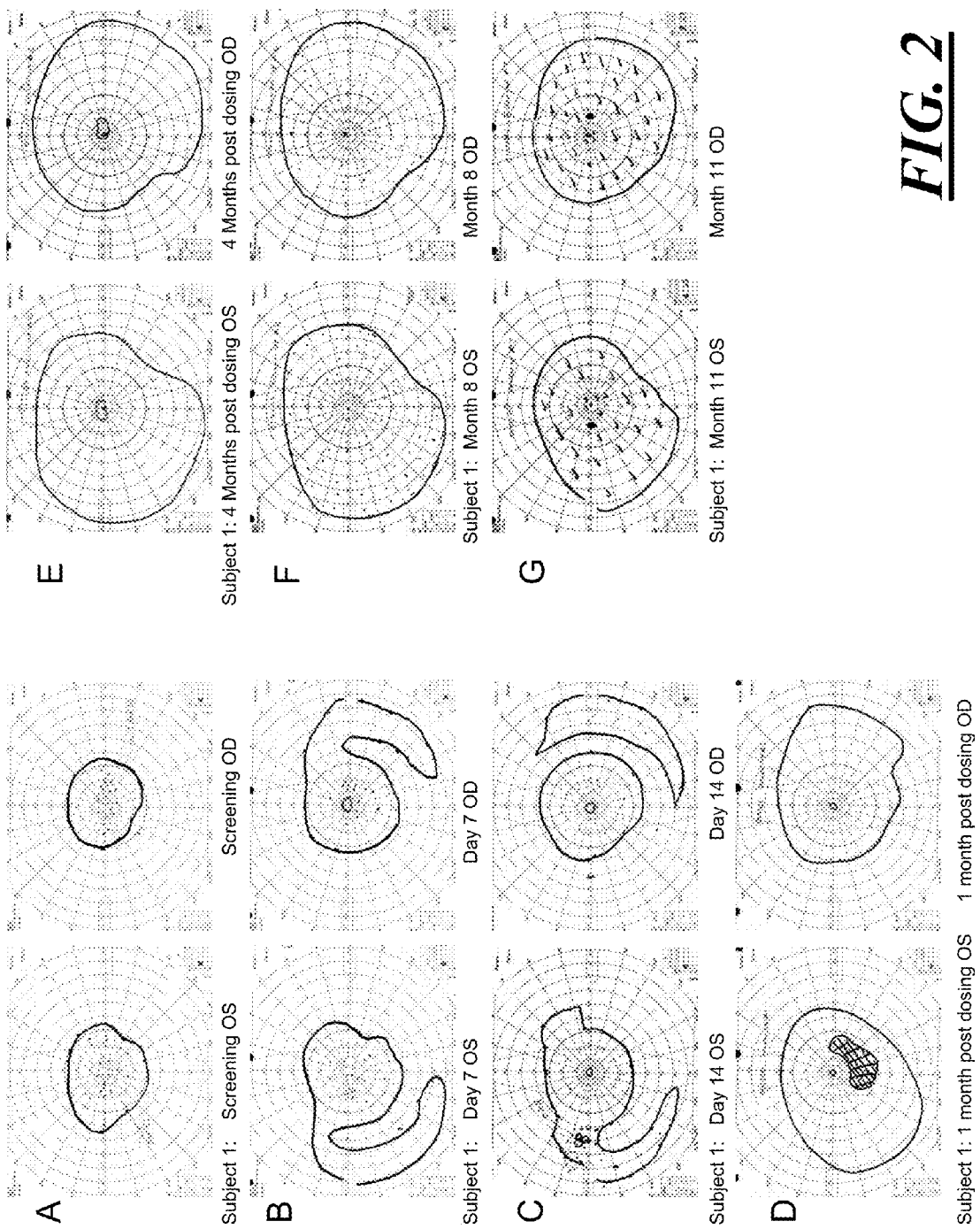
FIG. 2. Seven Goldmann visual fields (GVF) from subject #1 (A-G). Using the V4e target, progressive widening of the visual fields is seen in both eyes from screening (2A) to day 7 (2B), day 14 (2C), one month (2D) and four months (2E) after the initiation of 7 days of oral treatment with the composition of Example 1. Increased sensitivity to the smaller target I4e is also seen (2E).

Subject #1 is a 10-year-old Caucasian female with LCA. At baseline, she was legally blind and presented with lifelong night blindness, visual loss, nystagmus, and severely attenuated ERGs. Her Goldmann Visual Fields (GVFs) had progressively deteriorated. Her Early Treatment in Diabetic Retinopathy Study (ETDRS) visual acuity was 36 letters OD and 26 letters OS (approximately 20/200 and 20/320 Snellen equivalent). There was mild horizontal nystagmus. Ophthalmoscopic examinations were normal except for the "salt and pepper" changes in the retinal pigment epithelium (RPE) of the peripheral retina. Her GVF was constricted in both eyes to 30° with the V4e target and she was unable to see the I4e target (FIG. 2). She had no detectable rod-mediated or rod/cone-mediated ERGs, but some measurable cone-mediated activity (3.5 µV b-wave). Two baseline full-field threshold sensitivity (FST) tests revealed average thresholds of 0.5206 log cd/m2 (OD), whereas optical computed tomography (OCT) documented an essentially normal retinal structure.

Within 12 hours after the first dose of the Composition, the subject developed a moderate headache and experienced 1 episode of vomiting, followed by photophobia. The headache resolved a few hours later and the subject and her family reported improved visual function, especially in a dimly lit environment. These subjective improvements were reported to have persisted at 4 months after cessation of dosing with the composition.

During the study, there were no changes in the ophthalmoscopic exam. GVFs changed significantly and consistently (FIG. 2A-G). On Day 7, a new large temporal crescent was documented in both eyes by using the V4e target that remained on Day 14, when it was documented that she was also able to see the I4e (smaller) target (FIG. 2C). On Day 30, the visual fields had expanded temporally from 30° to 70° and nasally from 30° to 40° (FIG. 2D). The most unexpected change was found 4 months post-dosing, when her GVF size by the V4e target appeared close to the size expected in a normally-sighted child (FIG. 2E). FST sensitivity thresholds improved in the OD to 0.0990 log cd/m2 on Day 2 (24 hours after the first dose) and remained at 0.1496 log cd/m2 on Days 8, 10 and 15 (lower thresholds signify greater retinal sensitivity). ERG measurements, color vision and Smith-Kettlewell Institute Low Luminance (SKILL) chart measurements were unchanged from baseline.

Figure 4A:
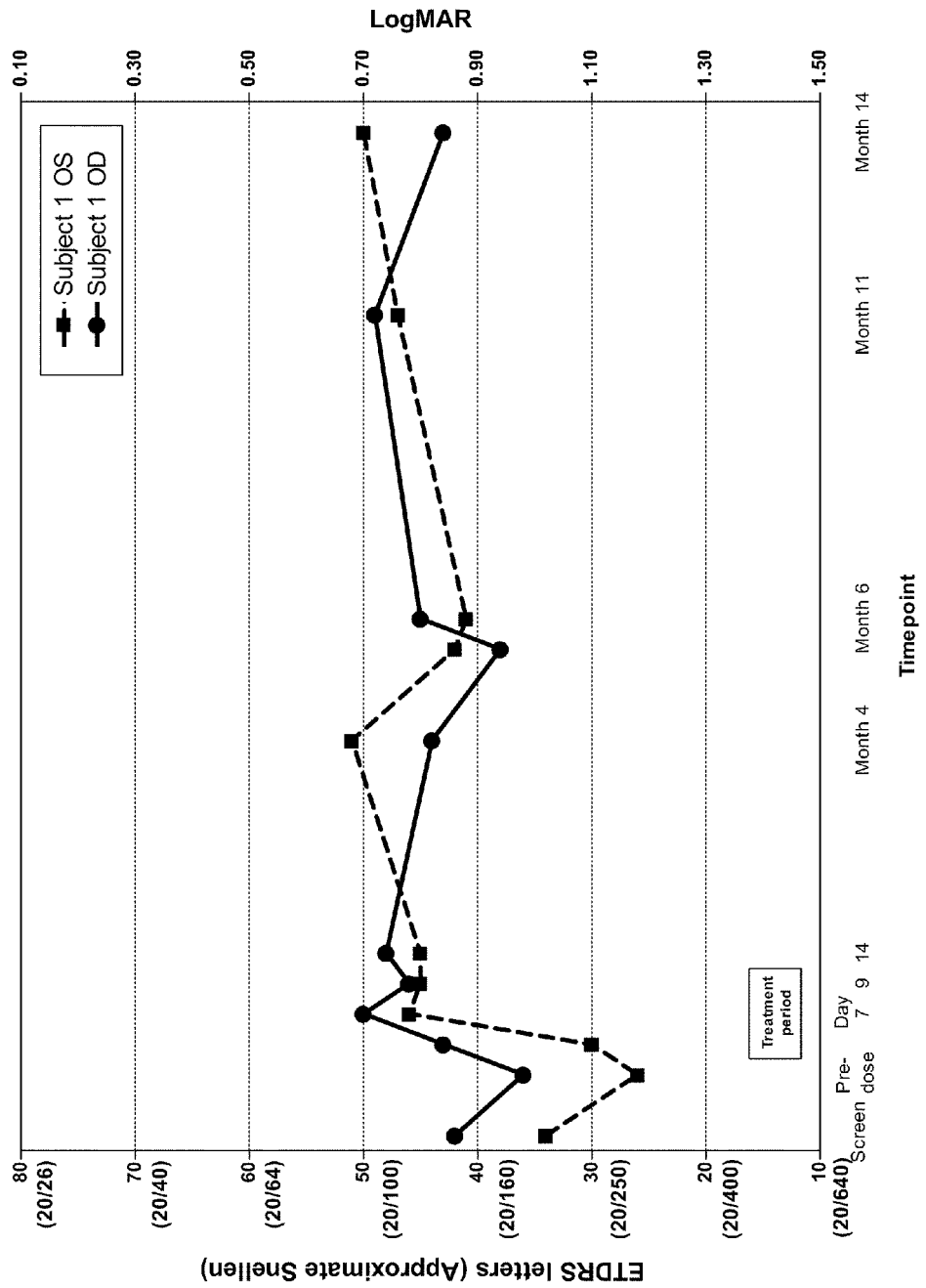
FIGS. 4A and 4B. Improvement in ETDRS/LogMAR/Snellen equivalent visual acuity during and after treatment in the right eye (OD) and left eye (OS) of subject #1 (FIG. 4A) and subject #2 (FIG. 4B). The left eye was patched at all times for the 7 days of treatment except during scheduled visual function tests. The patch was removed on Day 7.

ETDRS acuities improved during treatment, and has been monitored until Month 14 (FIG. 4A). Continued assessments showed that the improvements relative to baseline (screening) have been maintained beyond the end of the treatment period.

Vision Characteristics of Subject #2 Before and After Treatment

Subject #2 is the 12-year-old brother of subject #1, who was also diagnosed with LCA at birth. He has had lifelong night blindness, nystagmus, and is legally blind. ETDRS best-corrected visual acuity was 9 letters OD and 7 letters OS (approximate Snellen 20/800) at baseline. Ophthalmoscopic examination revealed arteriolar narrowing, significant peripheral pigmentary degeneration and a prominent maculopathy with foveal atrophy and RPE disruption. GVFs showed a large central defect with relatively intact peripheral fields. His ERGs were non-detectable. Macular OCT revealed abnormalities in the retinal architecture with deposits between the photoreceptor and outer plexiform layers.

Figure 4B:
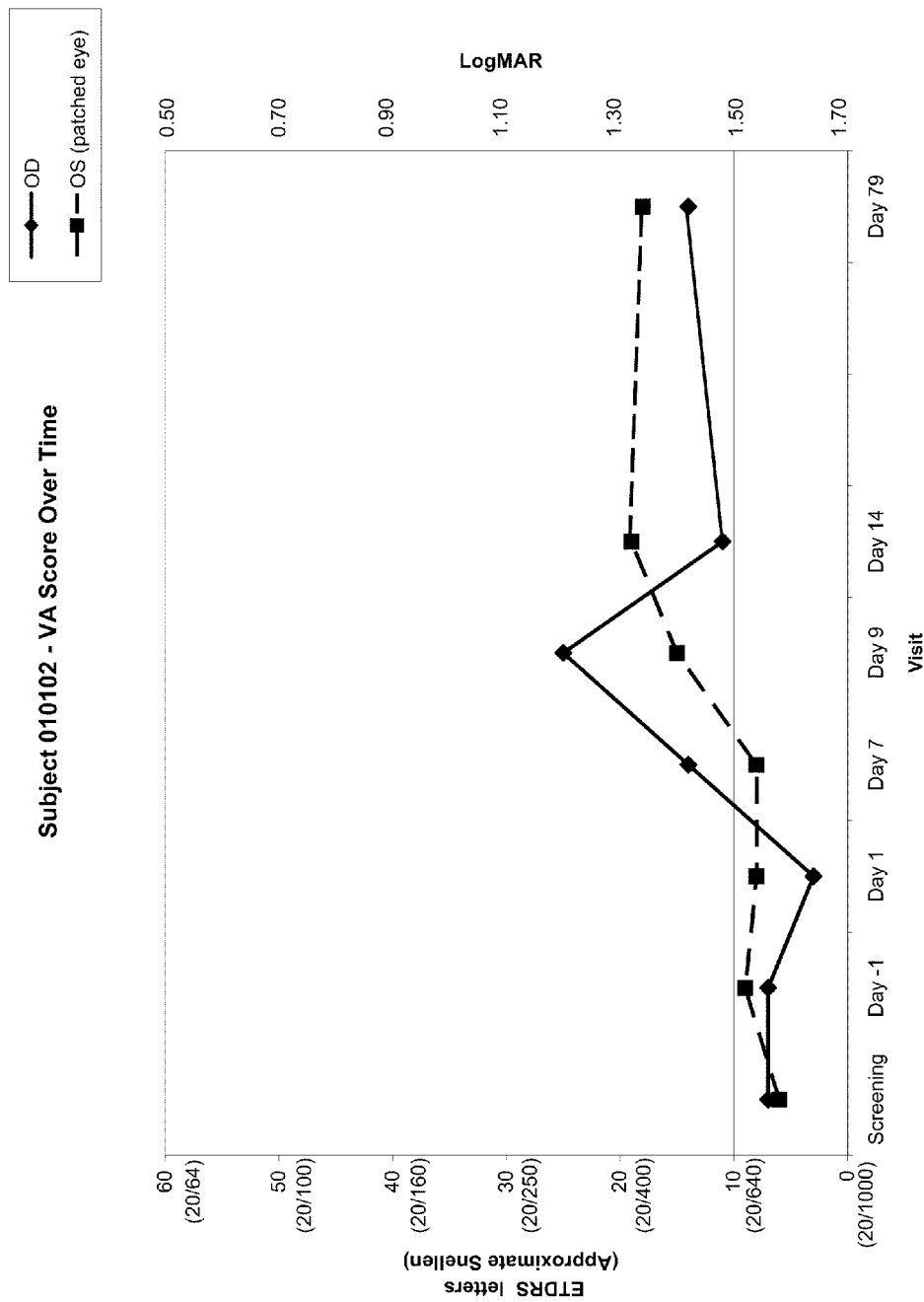

Upon treatment with the Composition of Example 1, this subject did not develop a headache. There was no change in the ophthalmoscopic exam. FIG. 4B shows that the ETDRS best-corrected visual acuities were significantly improved following treatment. This improvement has been maintained during follow-up (79 days). There were no changes in GVF, color vision, SKILL, ERG, or FST findings.

Vision Characteristics of Subject #3 Before and After Treatment

Subject #3 is a 38-year-old woman with LCA unrelated to the first 2 subjects. She had legal blindness, nystagmus, and required assistance to ambulate. She was unable to see any letters on the ETDRS chart. She could see "hand motions" without the ability to count fingers at 1 m. Similarly, her color vision and SKILL visual acuity scores were 0. Her GVF was non-detectable (FIG. 3A) and ERG was significantly attenuated OD (1.2 μv) and not recordable OS. The OCT examination revealed an intact retinal architecture with a visible foveal OS/IS junction, confirming the presence of foveal photoreceptors.

Twelve hours after the first dose of the Compostion, she developed a moderate headache and photophobia. The headache resolved a few hours later and her photophobia decreased over the next 2 days. On Day 2 of treatment, while in the clinic, she reported that she was clearly able to see the outline of a computer monitor, the mirror in the bathroom and a white sheet of paper on a dark desk, none of which she had been able to see prior to the study. There were no changes in the ophthalmoscopic exam. On Day 9, she was able to read the ETDRS chart for the first time, and reached a letter score of 2 OS (approximate Snellen 20/1000). She was also able to reliably see the V4e target centrally on the GVF (FIG. 3B) on Days 3 and 7, but this became less reliable on Days 9 and 14. Retinal sensitivity improved from 1.1966 at screening to 0.9508 log cd/m2 at Day 14 OD and from 2.2763 to 2.0688 log cd/m2 OS. Her other visual function tests were unchanged from baseline.

Summary of Results with Subjects #1, 2 and 3

Three subjects aged 10, 12, and 38 years, all of whom have a genetic mutation in LRAT, were enrolled and treated. All 3 patients had the identical homozygous c.217_218delAT deletion in LRAT that leads to a p. Met73AspfsX47 frameshift and premature truncation of the LRAT protein, which likely represents a null allele. After 7 days of treatment with the oral composition of Example 1, all of the subjects experienced clinically meaningful improvements in one or more visual function parameters, including best-corrected visual acuity, Goldmann visual field, and/or retinal sensitivity as measured by full-field sensitivity threshold testing. Subjects have also reported meaningful improvements in their visual performance related to tasks of daily living. The onset of visual changes was rapid and there was progressive improvement beyond the 7 days of treatment, with some effects persisting for more than 4 months after treatment was completed. Improvements were most pronounced in the youngest subject, but clinically relevant changes were also noted in the one adult subject treated to date. The study treatment has been well-tolerated, with mild to moderate adverse events observed including transient headache, photophobia, and an increase in triglyceride levels.

Discussion

In the above example, 7 days of treatment with the Composition meaningfully restored bilateral visual function in 3 subjects with LCA and LRAT mutations, who had lifelong progressive visual loss due to this severe and blinding retinal condition. Improvement in three visual function parameters, including ETDRS visual acuities, GVF size and retinal sensitivity by FST, have been documented. Improvements became evident in as little as 12 hours following the first oral dose of the Composition and persisted or increased in magnitude in all follow-up visits to date (subject #1 over 14 months, subject #2 over 3 months, and subject #3 over 2 weeks).

ETDRS visual acuity improved in all 3 subjects and the GVF improved in subjects #1 and #3. FST testing documented improved retinal sensitivities in subject #1 and #3. In subject #1 the threshold improved from 0.5206 to 0.0990 and then to 0.1496 log cd/m2. This improvement is likely significant as test-retest variability was measured at 0.3 log cd/m2 by Klein and Birch in similar patients with severe retinal dystrophies. Klein M, et al. Doc Ophthalmol 119:217-24 (2009). The improvement in retinal sensitivity in subject #3 does not reach significance. Subjects' improvements were not limited to clinical testing: all 3 have noted significant gains in their ability to read and perform activities of daily living. Most significantly, subject #1 reported during the study that they no longer need a cane to navigate, sees in dimly lit areas, can read the clock on the wall and is now able to perform her own self-care. Subject #3 was able during the study to read effectively by using vision aids and could see formed objects that she had not been able to see for years, including papers and mirrors.

Following oral administration of the composition, without wishing to be bound by any particular theory, it is believed that the drug is incorporated into lipid droplets in the liver and in the RPE (called retinosomes) from which it is mobilized. Imanishi Y. et al. J Cell Biol 166:447-53 (2004). It is secreted by the liver bound to retinol binding-protein 4 (RBP4) and delivered to peripheral tissues, whereas in the eye it is oxidized to 9-cis-retinal which feeds back into the retinoid cycle (FIG. 1). Moise A. R. et al. Biochemistry 46:4449-58 (2007). Retinols, regardless of their isomeric form, are also stored in adipocytes and mobilized as needed into the circulation. O'Byrne S. M. et al. J Biol Chem 280:35647-57(2005). Thus, the long-term effects of this chromophore analog may derive from the fact that active drug is slowly released from adipocytes in the periphery.

Results observed in this study suggested the existence of dormant photoreceptors that may rapidly respond to oral treatment such that patients at least into the fourth decade of life may benefit. Additionally, the findings in subject #1 suggested that the Composition may be able to restore visual function to large areas of previously unresponsive photoreceptors.has been maintained until Day 114 (FIG. 4A). Continued assessments showed that the improvements relative to baseline (screening) persisted for up to and including 11 months beyond the end of the treatment period.

Example 4

Efficacy Assessment

Subject #5 was a 13-year-old Asian female with LCA due to missense mutations in the RPE65 gene at Leu67Arg/Tyr368Cys. At baseline, her retinal architecture was relatively intact (OCT) and there was a small amount of FAF in her inferior retina. At baseline, she presented with mild progression visual loss, nystagmus, non-detectable rod ERG, and severely decreased cone ERG. Her Goldmann Visual Fields (GVFs) had superior defects. Her Early Treatment in Diabetic Retinopathy Study (ETDRS) visual acuity was 31 letters OD and 34 letters OS (approximately 20/250 Snellen equivalent).

Figure 5:
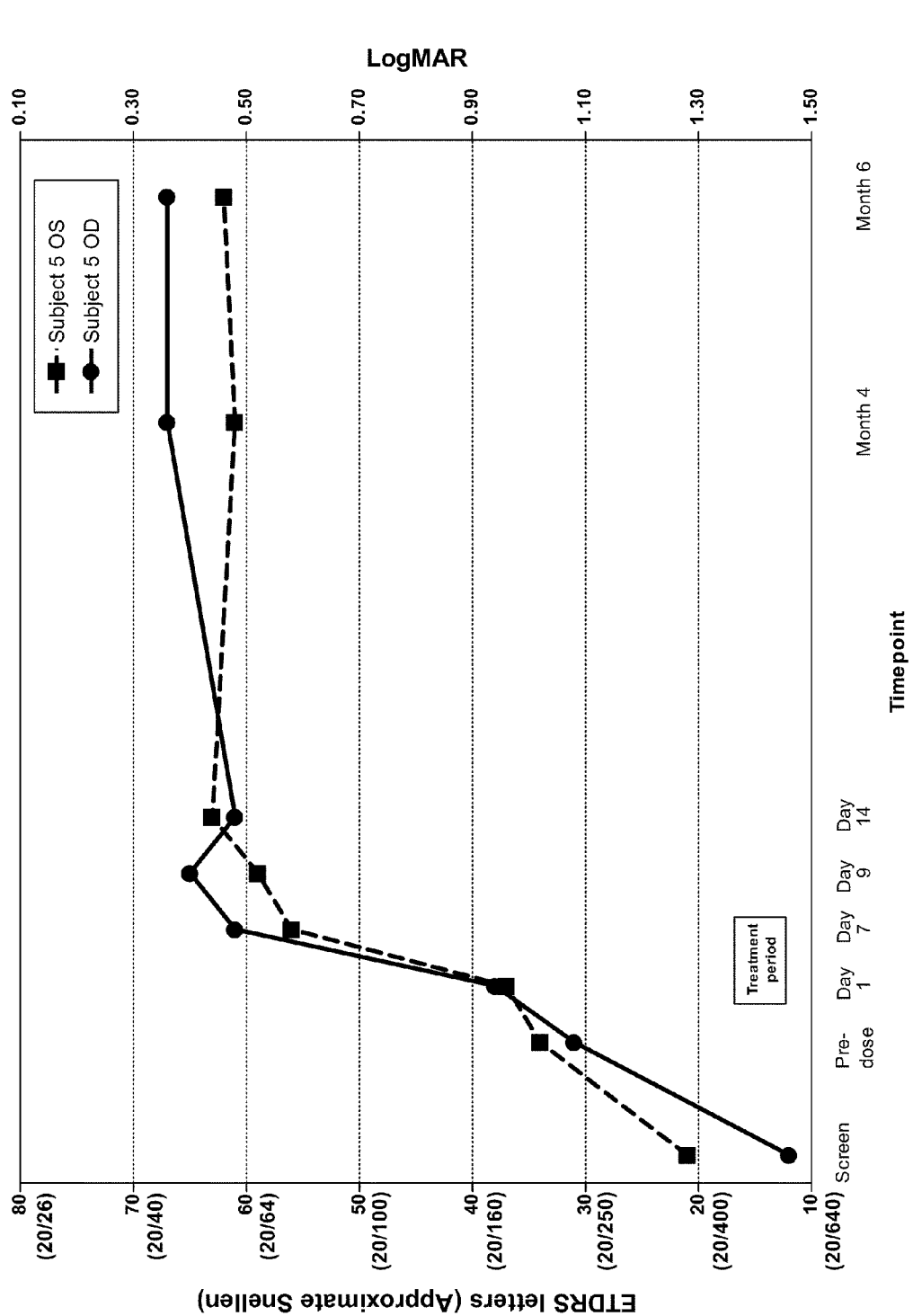
FIG. 5. Improvement in ETDRS/LogMAR/Snellen equivalent visual acuity during an after treatment in the right eye (OD) and left eye (OS) of subject #5 up to six months after dosing.

The subject was treated with 40 mg/m2 of the Composition of Example 1 for 7 days as described in Example 2. On Day 9, her binocular visual acuity was 20/30. The patient was monitored for 6 months post dosing. ETDRS acuities remain improved, at 67 letters OD and 62 letters OS (FIG. 5). GVF improvements of the superior field and central field as observed with IV4e and I4e targets also persisted. No change in ERG was observed.

The subject also reported meaningful improvements in activities of daily living after treatment. She noted the ability to see images on a small screen, see the colors of fireworks, and see stars in the sky. She reported improved vision and mobility in dim light. The observed improvements from baseline have been monitored for 6 months post dosing and have persisted during this time period.

Example 5

Efficacy Assessment

Subject #9 was a 14-year-old Hispanic female with LCA due to missense mutations in the RPE65 gene at Arg91Gln/Leu341Ser. At baseline, retinal degeneration was observed by retinal exam and OCT, with relatively intact foveal architecture (OCT) and FAF showed lipofuscin in the inferior retina. At baseline, she presented with mild nystagmus. Her Early Treatment in Diabetic Retinopathy Study (ETDRS) visual acuity was 41 letters OD and 47 letters OS (approximately 20/200 Snellen equivalent).

The subject was treated as outlined in Example 2, however a low dose, 10 mg/m2 of the Composition of Example 1 for 7 days was used. There were small improvements in GVF, with her VF almost doubling as observed with the I4e target (OD) by Day 14. ETDRS visual acuity improvements were observed, with the highest improvement from baseline of 10 letters (OD) at Day 14. Objective testing of cortical visual function before and after drug treatment was conducted using fMRI, and marked improvements observed, with subjective reporting of the ability to see the images on the fMRI projector post treatment.

The subject has also reported meaningful improvements in activities of daily living. Improvements in color vision, peripheral vision and vision in low lighting (night) were reported. The patient has been monitored 2 months beyond the end of the treatment period and the observed improvements from baseline persisted.

Example 6

Efficacy Assessment

The efficacy of the composition of Example 1 was tested in human subjects having RP (with LRAT or RPE65 mutation). Subjects of a first dose group received a once-daily initial dose of the Composition (40 mg/m2) for 7 days. Subjects of a second dose group received a once-daily initial dose of the Composition (10 mg/m2) for 7 days. Subjects were treated on an outpatient basis, but received study treatment in the research clinic under medical supervision for each day of treatment. During the study, subjects were required to limit vigorous physical activity (to avoid laboratory variability) and avoid excessive vitamin A intake in order to reduce the influence of such factors on the assessment of safety variables in this study.

Both eyes of each subject were evaluated separately. Protocol-defined assessments of visual function included: best-corrected visual acuity testing using Early Treatment Diabetic Retinopathy Study (ETDRS) testing followed by low/high contrast Smith-Kettlewell Institute Low Luminance (SKILL) charts; visual field testing using Goldmann perimetry; full-field electroretinogram (ERG); and full-field stimulus threshold testing (FST). Baseline ERGs, ETDRS, and SKILL tests were repeated twice. During and after treatment, visual function tests were conducted on Day 1, 7, 9/10, and 14/15.

There was no requirement that the subjects wear eye patch on one or both eyes.

The efficacy assessments of this study were conducted according to the procedures as set forth in Examples 2 and 3, as well as assessments of dynamic pupillary response, nystagmus, cortical visual function, visual mobility, and patient-reported outcomes on quality of life.

Subject #10 was a 27-year-old Indian male with RP due to homozygous mutations in the LRAT gene at c.525T>A; p.Ser175Arg. His ETDRS visual acuity at baseline was 71 letters OD and 60 letters OS (approximately 20/40 and 20/62.5 Snellen equivalent) unaided.

The subject was treated with 40 mg/m2 of Composition A for 7 days, as described in Example 6. Small improvements in ETDRS visual acuity were observed, with the highest improvement from baseline of 11.5 letters (OD) at Day 9, and 14.5 letters OS at Month 1.5. Large improvements in GVF OD were detected, and supported by subjective reports of improvements in peripheral vision. Objective testing of cortical visual function before and after drug treatment was tested using fMRI, with marked improvements observed. No changes in cone or rod ERG were seen.

The subject reported meaningful improvements in activities of daily living. Sensitivity to daylight and fluorescent lights was noted. Dark adaptation times were also improved. The patient was monitored for 1.5 months beyond the end of the treatment period, with improvements from baseline persisting.

Summary of Efficacy Data

The following summarizes the results of the efficacy data from the above Examples.

Figure 7:
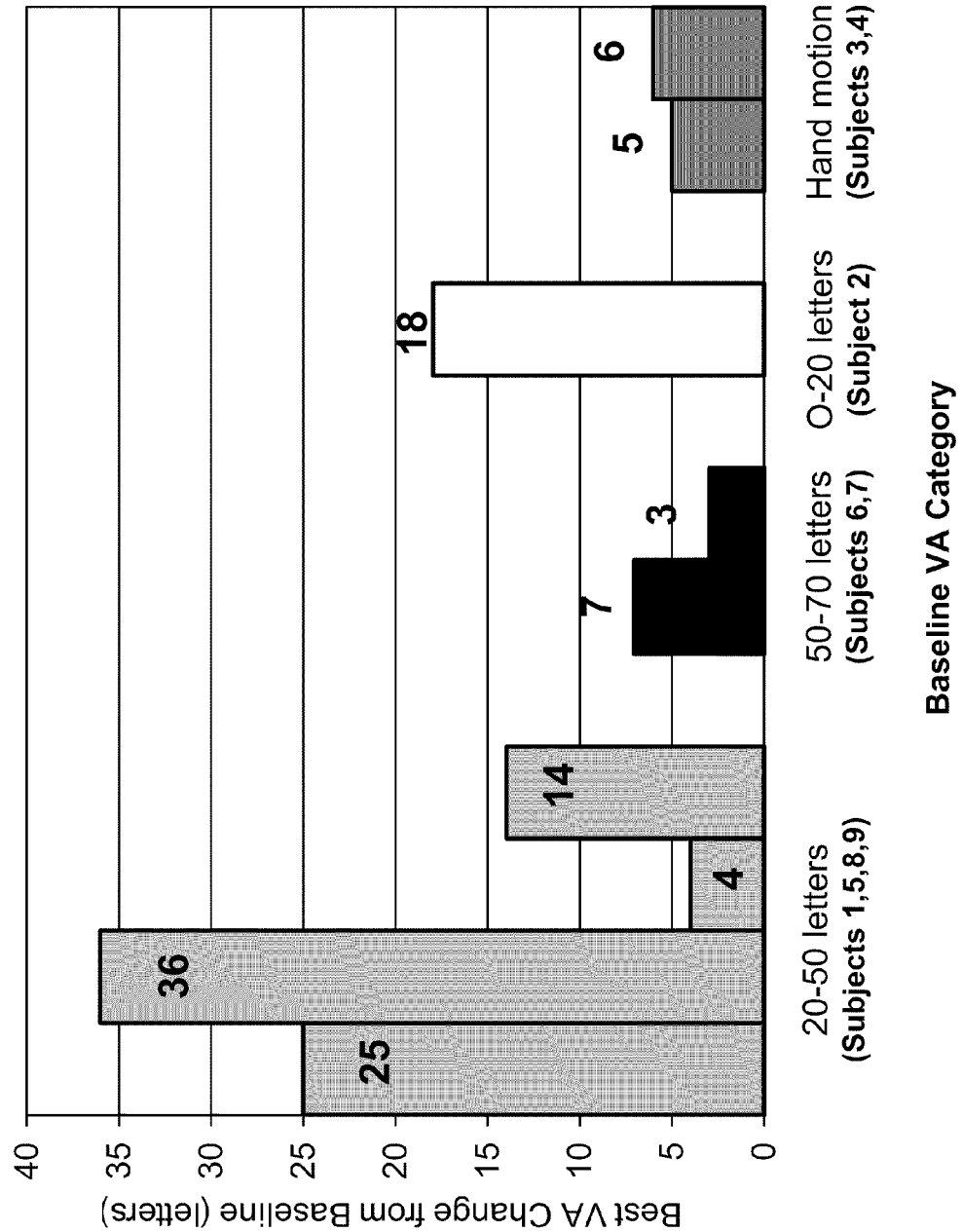
FIG. 7. Overall summary of best change in visual acuity (VA) from baseline (ETDRS letter score) from Day 9 to Month 8 post dosing. Data has been clustered based on Baseline VA category.
Figure 8:
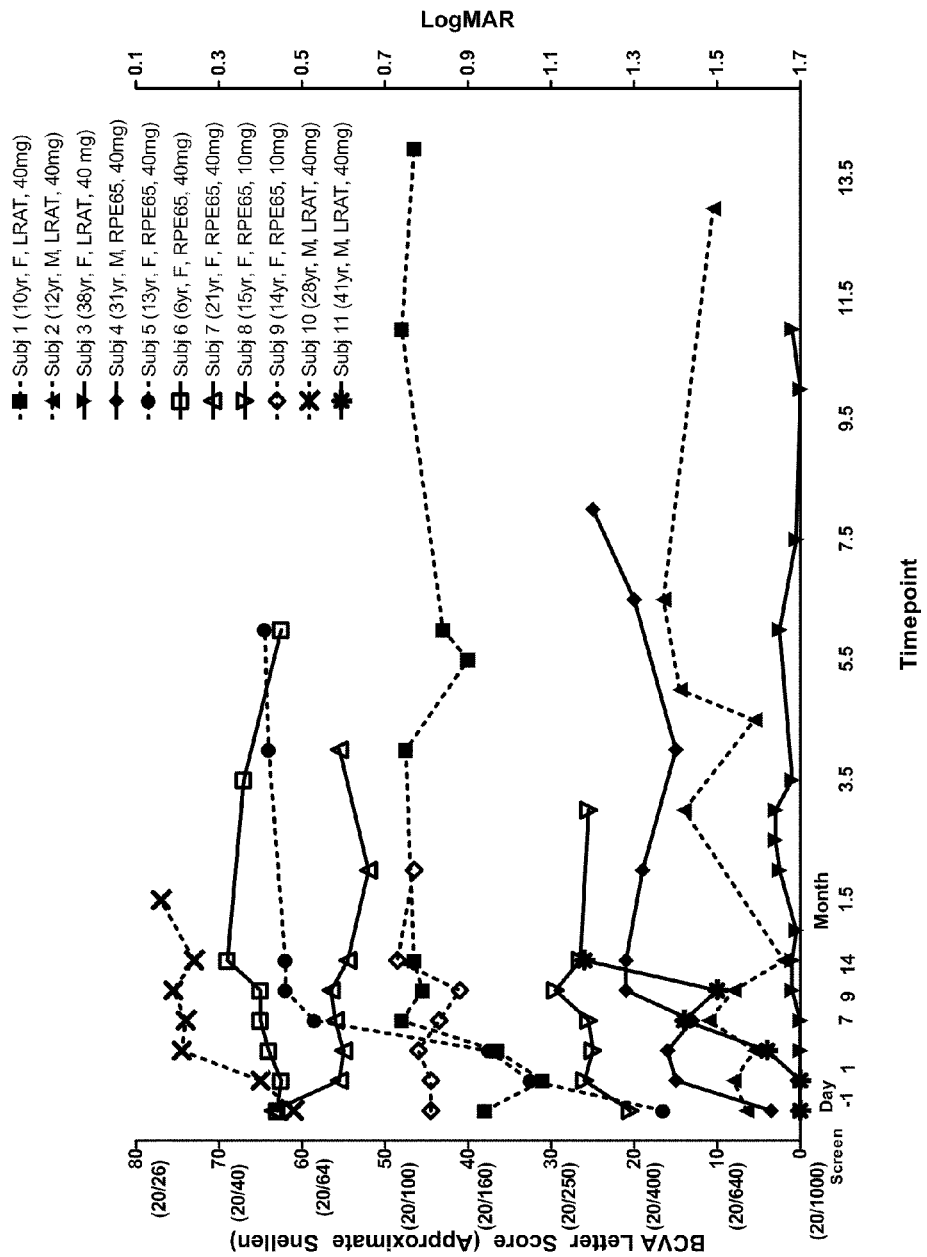
FIG. 8. ETDRS/LogMAR/Snellen equivalent visual acuity (VA) the eleven subjects of FIG. 6 after treatment with either 40 mg/m2 (40 mg) or 10 mg/m2 (10 mg) of the Composition. Data represents the average letter score for both eyes, with the exception of Subjects 4 and 11, both of which demonstrated measurable letter scores for only one eye.

A total of 11 subjects were studied, comprising two mutation types (LRAT and RPE65), two disease types (Leber Congenital Amaurosis (LCA) and Retinitis Pigmentosa (RP)), different age ranges (6 subjects 6-15 years and 5 subjects 21-41 years), and a broad range of baseline visual function (FIG. 6). Four distinct ranges of baseline VA were established: hand motion and light perception, VA in the 0-20 letter range, VA in the 20-50 letter range, and VA in the 50-70 letter range. Largest responses in improvement in VA was observed for patients with a modest level of retinal function (Vas in the 20-40 letter range), all of which were treated with 40 mg/m2 of the Composition (FIG. 7). The best responses, 3 lines of improvement, were seen in the younger patients (10-13 years). Relative improvements in visual acuity over baseline for the 11 subjects were monitored for up to 14 months post dosing, demonstrating persistence of clinically meaningful improvements (FIG. 8).

Figure 9A:
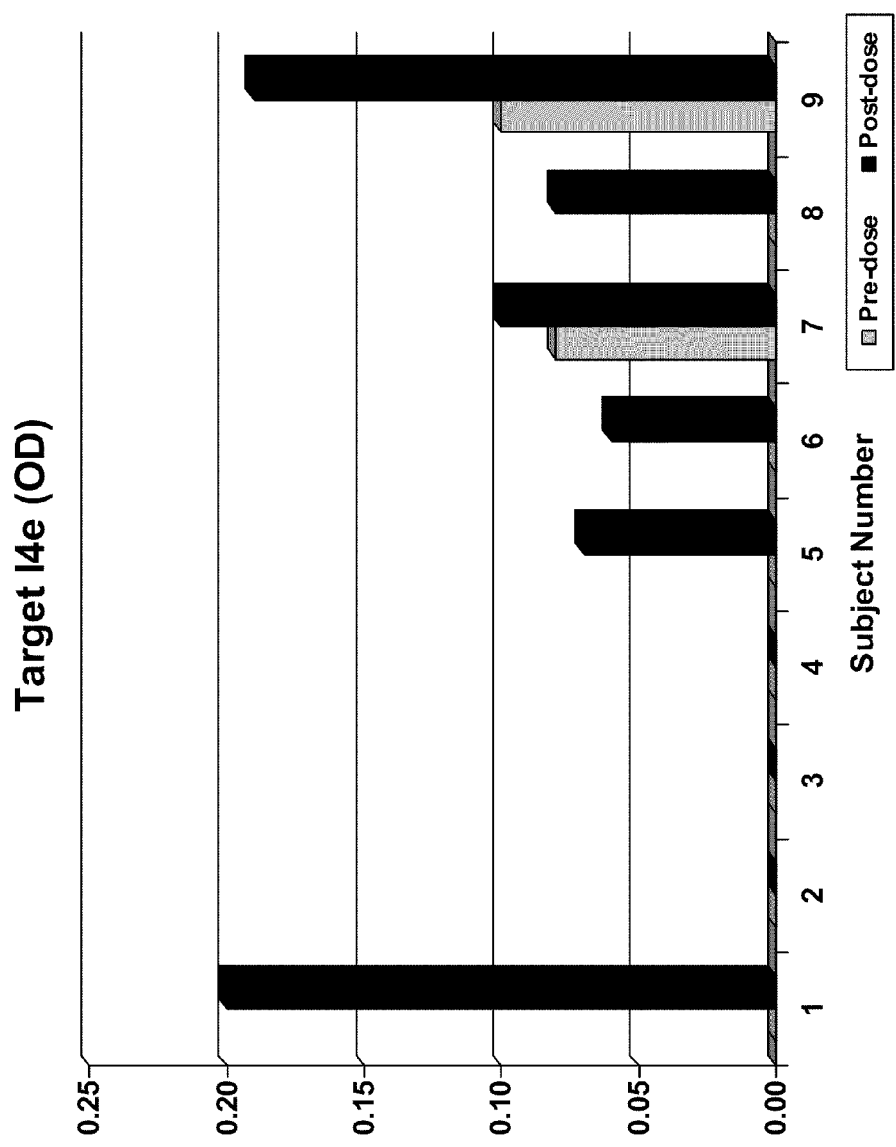
FIG. 9. AMA low vision grid analysis of the Goldmann visual fields (GVF) for Subjects 1-9. Analysis was performed of the GVFs observed with either the small I4e target (FIG. 9A) or the larger V4e target (FIG. 9B) before and at Day 14.
Figure 9B:
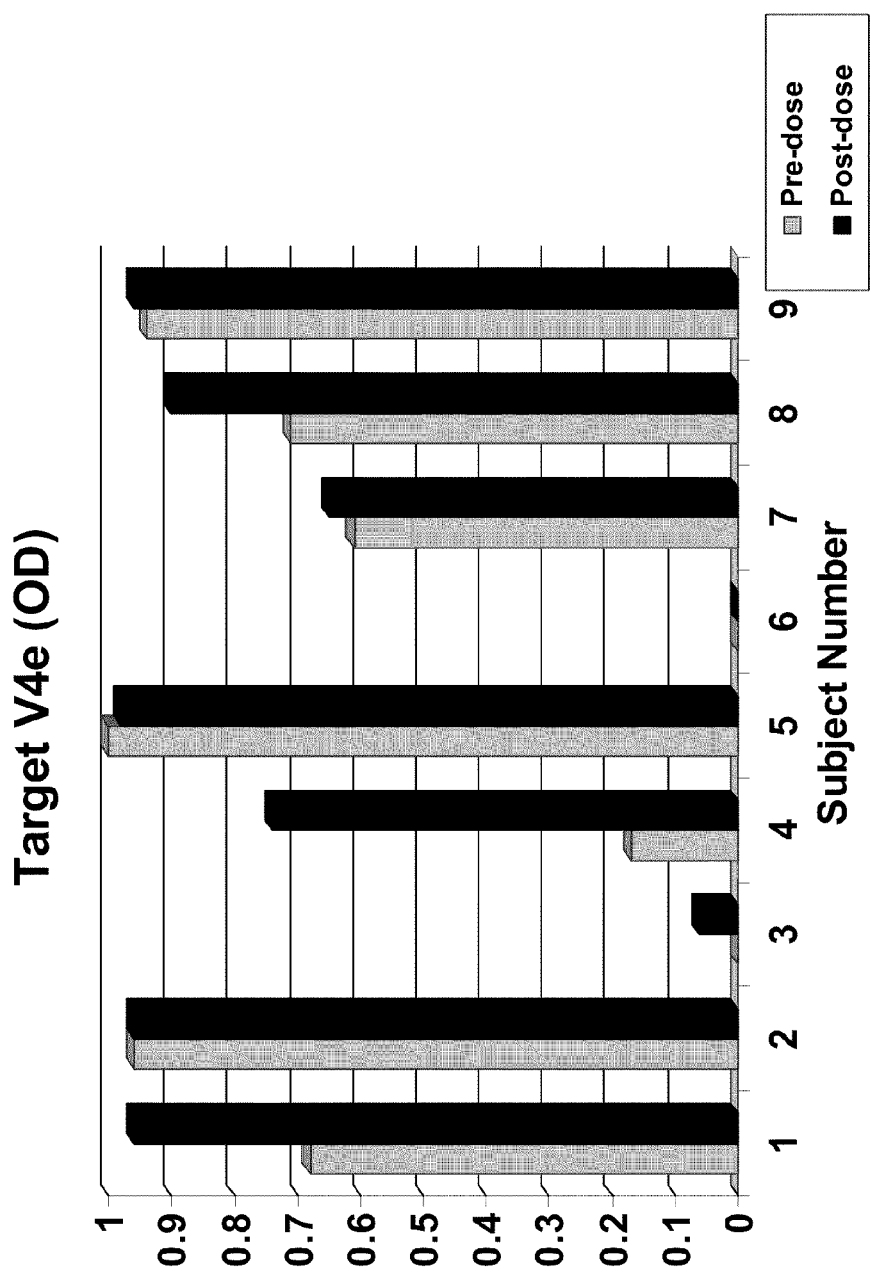

AMA low vision grid analyses of the GVFs from Day 14 for the first 9 patients treated showed that 7 of 9 patients demonstrated marked improvements as detected with either the smaller I4e target (FIG. 9A) or the larger V4e target (FIG. 9B).

Preliminary data obtained from use of the Children's Visual Function Questionnaire (CVFQ) or Low Luminance Questionnaire (LLQ) have been combined with subjective reports on improvements in activities of daily living, and support the rapid improvement in visual function and prolonged therapeutic benefit of treatment with the Composition.

The study treatment was well tolerated. Adverse events related to treatment included transient photophobia and headaches, vomiting, moderate elevations in triglyceride levels, and a trend toward a decrease in HDL levels in all subjects. Effects on lipid metabolism, a recognize class effect for retinoids, was found to peak at Day 7 of dosing (FIG. 10), but returned to baseline within 4 weeks after treatment was completed. Overall, adverse events, including effects on lipid metabolism, were more pronounced in the 40 mg/m2 group relative to the lower dosed 10 mg/m2 group.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A method for treating a human patient suffering from the loss or impairment of vision caused by Leber Congenital Amaurosis (LCA), wherein said patient is deficient in endogenous 11-cis-retinal disorder, comprising the steps of:
  a) administering to the human patient an initial therapeutically effective dose of a synthetic retinal derivative selected from the group consisting of 9-cis-retinyl acetate, 9-cis-retinyl formate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, 9-cis-retinyl propionate, 9-cis-retinyl butyrate, 9-cis-retinyl valerate, 9-cis-retinyl hexanoate, 9-cis-retinyl heptanoate, 9-cis-retinyl octanoate, 9-cis-retinyl nonanoate, 9-cis-retinyl decanoate, 9-cis-retinyl undecanoate, 9-cis-retinyl dodecanoate, 9-cis-retinyl oxalate, 9-cis-retinyl malonate, 9-cis-retinyl glutarate, 9-cis-retinyl adipate, 9-cis-retinyl pimelate, 9-cis-retinyl suberate, 9-cis-retinyl azelate, and 9-cis-retinyl sebacate,
  b) refraining from administering to the human patient an additional therapeutically effective dose of the synthetic retinal derivative for a resting interval, wherein the resting interval is a time period between 1 month and 14 months,
  c) administering to the human patient the additional therapeutically effective dose of the synthetic retinal derivative.

2. The method of claim 1, wherein the initial dose is administered in a single dose.

3. The method of claim 1, wherein the initial dose is administered in a divided dose over a period of from 5 to 14 days.

4. The method of claim 1, wherein the initial dose is administered in a divided dose over a period of 7 to 10 days.

5. The method of claim 1, wherein the initial dose is administered in a divided dose over a period of one week.

6. The method of claim 1, wherein the synthetic retinal derivative is 9-cis-retinyl acetate.

7. The method of claim 6, wherein the initial dose is administered in a divided dose over a period of two weeks.

8. The method of claim 1, wherein the initial dose is in the range of from 70 mg/m$^2$ to 525 mg/m$^2$.

9. The method of claim 1, wherein the initial dose is in the range of from 70 mg/m$^2$ to 490 mg/m$^2$.

10. The method of claim 1, wherein the initial dose is in the range of from 280 mg/m$^2$ to 490 mg/m$^2$.

11. The method of claim 1, wherein the initial dose is in the range of from 70 mg/m$^2$ to 280 mg/m$^2$.

12. The method of claim 5, wherein the initial dose is 280 mg/m$^2$.

13. The method of claim 8, wherein the initial dose of a synthetic retinal derivative is administered orally.

14. The method of claim 8, wherein the initial dose of a synthetic retinal derivative is administered by intraocular injection.

15. The method of claim 1, wherein the resting interval is a time period between 3 months and 14 months.

16. The method of claim 15, wherein the resting interval is a time period between 6 months and 14 months.

17. The method of claim 15, wherein the resting interval is a time period between 9 months and 14 months.

18. The method of claim 15, wherein the resting interval is a time period between 3 and 6 months.

19. The method of claim 15, wherein the resting interval is a time period between 6 and 9 months.

20. The method of claim 15, wherein the resting interval is a time period between 3 and 9 months.

21. The method of claim 15, wherein the resting interval is a time period between 3 months and 1 year.

22. The method of claim 1, wherein the LCA is caused by a mutation in the LRAT gene.

23. The method of claim 1, wherein the LCA is caused by a mutation in the RPE65 gene.

24. A method for treating a human patient suffering from loss or impairment of vision due to inherited mutations in RPE65 or LRAT genes associated with Leber congenital amaurosis, comprising the steps of:
  a) administering to the human patient an initial therapeutically effective dose of 9-cis-retinyl acetate,
  b) refraining from administering to the human patient an additional therapeutically effective dose of the 9-cis-retinyl acetate for a resting interval, wherein the resting interval is a time period between 1 month and 14 months, and
  c) administering to the human patient the additional therapeutically effective dose of the 9-cis-retinyl acetate.

25. The method of claim 24, wherein the initial dose is administered in a divided dose over a period of from 5 to 14 days.

26. The method of claim 24, wherein the initial dose is in the range of from 70 mg/m$^2$ to 525 mg/m$^2$.

27. The method of claim 24, wherein the resting interval is a time period between 3 months and 14 months.

28. The method of claim 1, wherein the resting interval is a time period between 1 month and 2 months.

29. The method of claim 1, wherein the resting interval is a time period between 1 month and 3 months.

30. The method of claim 1, wherein the resting interval is a time period between 1 month and 6 months.

31. The method of claim 1, wherein the resting interval is a time period between 1 month and 9 months.

32. The method of claim 1, wherein the resting interval is a time period between 1 month and 1 year.

33. The method of claim 24, wherein the resting interval is a time period between 1 month and 2 months.

34. The method of claim 24, wherein the resting interval is a time period between 1 month and 3 months.

35. The method of claim 24, wherein the resting interval is a time period between 1 month and 6 months.

36. The method of claim 24, wherein the resting interval is a time period between 1 month and 9 months.

37. The method of claim 24, wherein the resting interval is a time period between 1 month and 1 year.

38. The method of claim 24, wherein the resting interval is a time period between 6 months and 14 months.

39. The method of claim 24, wherein the resting interval is a time period between 9 months and 14 months.

40. The method of claim 24, wherein the resting interval is a time period between 3 months and 6 months.

41. The method of claim 24, wherein the resting interval is a time period between 6 months and 9 months.

42. The method of claim 24, wherein the resting interval is a time period between 3 months and 9 months.

43. The method of claim 24, wherein the resting interval is a time period between 3 months and 1 year.

44. The method of claim 1, wherein the initial dose is in the range of from 49 mg/m$^2$ to 840 mg/m$^2$.

45. The method of claim 44, wherein the initial dose is in the range of from 49 mg/m$^2$ to 280 mg/m$^2$.

46. The method of claim 24, wherein the initial dose is in the range of from 49 mg/m$^2$ to 840 mg/m$^2$.

47. The method of claim 46, wherein the initial dose is in the range of from 49 mg/m$^2$ to 280 mg/m$^2$.

\* \* \* \* \*